US012709635B2

(12) United States Patent
Felber et al.

(10) Patent No.: US 12,709,635 B2
(45) Date of Patent: Aug. 18, 2026

(54) METHODS AND COMPOSITIONS FOR INDUCING AN IMMUNE RESPONSE USING CONSERVED ELEMENT CONSTRUCTS

(71) Applicants: THE UNITED STATES OF AMERICA AS REPRESENTED BY THE SECRETARY, DEPARTMENT OF HEALTH AND HUMAN SERVICES, Bethesda, MD (US); University of Washington, Seattle, WA (US)

(72) Inventors: Barbara K. Felber, Rockville, MD (US); George N. Pavlakis, Rockville, MD (US); James I. Mullins, Seattle, WA (US); Antonio Valentin, Frederick, MD (US); Siriphan Manocheewa, Seattle, WA (US)

(73) Assignees: THE UNITED STATES OF AMERICA AS REPRESENTED BY THE SECRETARY, DEPARTMENT OF HEALTH AND HUMAN SERVICES, Bethesda, MD (US); University of Washington, Seattle, WA (US)

( * ) Notice: Subject to any disclaimer, the term of this patent is extended or adjusted under 35 U.S.C. 154(b) by 695 days.

(21) Appl. No.: 18/171,804

(22) Filed: Feb. 21, 2023

(65) Prior Publication Data

US 2023/0340029 A1 Oct. 26, 2023

Related U.S. Application Data

(63) Continuation of application No. 15/573,701, filed on Nov. 13, 2017, now abandoned, and a continuation-in-part of application No. PCT/US2016/032317, filed on May 13, 2016.

(60) Provisional application No. 62/241,599, filed on Oct. 14, 2015, provisional application No. 62/161,123, filed on May 13, 2015.

(51) Int. Cl.

| | |
|---|---|
| ***A61K 39/21*** | (2006.01) |
| ***A61K 9/00*** | (2006.01) |
| ***A61K 39/12*** | (2006.01) |
| ***A61K 39/39*** | (2006.01) |
| ***C07K 14/005*** | (2006.01) |
| ***C07K 14/16*** | (2006.01) |
| ***C07K 14/535*** | (2006.01) |
| ***C12N 7/00*** | (2006.01) |
| *A61K 39/00* | (2006.01) |

(52) U.S. Cl.

CPC .......... *C07K 14/005* (2013.01); *A61K 9/0009* (2013.01); *A61K 9/0019* (2013.01); *A61K 39/21* (2013.01); *A61K 39/39* (2013.01); *C07K 14/161* (2013.01); *C07K 14/535* (2013.01); *A61K 2039/53* (2013.01); *A61K 2039/54* (2013.01); *A61K 2039/545* (2013.01); *A61K 2039/55522* (2013.01); *A61K 2039/55561* (2013.01); *A61K 2039/572* (2013.01); *A61K 2039/575* (2013.01); *C07K 2319/02* (2013.01); *C12N 2740/16122* (2013.01); *C12N 2740/16134* (2013.01); *C12N 2740/16171* (2013.01); *C12N 2740/16222* (2013.01); *C12N 2740/16234* (2013.01); *C12N 2740/16271* (2013.01)

(58) Field of Classification Search

CPC .......... A61K 2039/53; A61K 2039/545; A61K 39/12; A61K 39/21; C07K 14/161

See application file for complete search history.

(56) References Cited

U.S. PATENT DOCUMENTS

| | | | | |
|---|---|---|---|---|
| 2004/0054137 A1 | | 3/2004 | Thomson et al. | |
| 2006/0205070 A1 | * | 9/2006 | Dundr .................... | A61K 39/12 435/6.14 |

FOREIGN PATENT DOCUMENTS

| | | | |
|---|---|---|---|
| CN | 101469339 | * | 7/2009 |
| CN | 102559724 | * | 7/2012 |
| WO | WO 1993/018791 | | 9/1993 |
| WO | WO9820036 | * | 5/1998 |
| WO | WO 2001/024810 | | 4/2001 |
| WO | WO200124810 | * | 4/2001 |
| WO | WO200190197 | * | 11/2001 |
| WO | 200236806 | | 5/2002 |
| WO | WO2005012502 | * | 2/2005 |
| WO | WO 2007/098257 | | 8/2007 |
| WO | WO2008005929 | * | 1/2008 |
| WO | WO2008033500 | * | 3/2008 |
| WO | WO 2008/063331 | | 5/2008 |
| WO | 2008089144 | | 7/2008 |
| WO | WO2008109059 | * | 9/2008 |
| WO | WO 2008/151633 | | 12/2008 |
| WO | WO 2009/046984 | | 4/2009 |
| WO | WO2010037402 | * | 4/2010 |
| WO | WO2010148335 | * | 12/2010 |

(Continued)

OTHER PUBLICATIONS

International Patent Application No. PCT/US2016032317, "International Search Report and Written Opinion", mailed Oct. 21, 2016, 15 pages.

(Continued)

*Primary Examiner* — Barry A Chestnut
(74) *Attorney, Agent, or Firm* — McDonnell Boehnen Hulbert & Berghoff LLP

(57) ABSTRACT

The invention provides methods and compositions for eliciting broad immune responses to HIV envelope proteins. The methods include use of nucleic acids constructs that encode conserved elements of HIV Env to induce immune responses.

46 Claims, 26 Drawing Sheets

Specification includes a Sequence Listing.

(56) References Cited

FOREIGN PATENT DOCUMENTS

| | | | |
|---|---|---|---|
| WO | WO2011022725 | * | 2/2011 |
| WO | WO2011077093 | * | 6/2011 |
| WO | WO 2011/082422 | | 7/2011 |
| WO | WO2011109511 | * | 9/2011 |
| WO | WO2012055987 | * | 5/2012 |
| WO | WO2012092934 | * | 7/2012 |
| WO | WO2013/131099 | * | 9/2013 |
| WO | WO 2014/027082 | | 2/2014 |
| WO | WO 2014/145355 | | 9/2014 |
| WO | WO2014166500 | * | 10/2014 |

OTHER PUBLICATIONS

Rolland, et al, HIV-1 Conserved-Element Vaccines: Relationship between Sequence Conservation and Replicative Capacity, May 2013, 7 pages.

Kulkami, et al., HIV-1 Conserved Elements p24CE DNA Vaccine Induces Humoral Immune Responses with Broad Epitope Recognition in Macaques, Oct. 2014, 12 pages.

Rolland, et al., HIV-1 Group M Conserved Element Vaccine, Nov. 2007, 5 pages.

Stephenson, et al., Full-Length HIV-1 Immunogens Induce Greater Magnitude and Comparable Breadth of T Lymphocyte Responses to Conserved HIV-1 Regions Compared with Conserved-Region-Only HIV-1 Immunogens in Rhesus Monkeys, Nov. 2012, 7 pages.

Examination Report issued in European Application No. 23185862.2, dated Apr. 2, 2026, 11 pages.

* cited by examiner

```
                    CE1            CE2                   CE3
HIVp24CE
  HIV p24CE1        ISPRTLNAWVKV   VIPMFSALSEGATPQDLN    VGGHQAAMQMLKDTINEEAAEWDR
  HIV p24CE2        L...........   .....T............    ............E...........
SIVp27CE
  SIV p27CE1        L..........L   .V.G.Q.....C..Y.I.    ..D......IIR.I......D..L
  SIV p27CE2        L..........L   .V.G.Q.....CA.Y.I.    ..E......IIR.I......D..L
  CON Sequences:
  SIVmac            L..........L   .V.G.Q.....C..Y.I.    ..D......IIR.I......D..L
  SIVsmm            L..........L   .V.G.Q.....C..Y.I.    ..E......IIREI......D..L

                    CE4                  CE5                    CE6              CE7
HIVp24CE
  HIV p24CE1        PRGSDIAGTTSTLQEQIGW  KRWIILGLNKIVRMYSPTSI   YVDRFYKTLRAEQA   LEEMMTACQGVGGPGH
  HIV p24CE2        .................A.  .................V..   .....F........   ..............S.
SIVp27CE
  SIV p27CE1        .S.........SVD...Q.  R...Q...Q.C....N..N.   .......S.....T   ....L..........Q
  SIV p27CE2        ............VE...Q.  R...Q...Q.C....N.VN.   .......S.....T   ....L..........Q
  SIVmac            .S.........SVD...Q.  R...Q...Q.C....N..N.   .......S.....T   ....L..........Q
  SIVsmm            ............VE...Q.  R...Q...Q.C....N..N.   .......S.....T   ....L..........Q
```

Figure 1

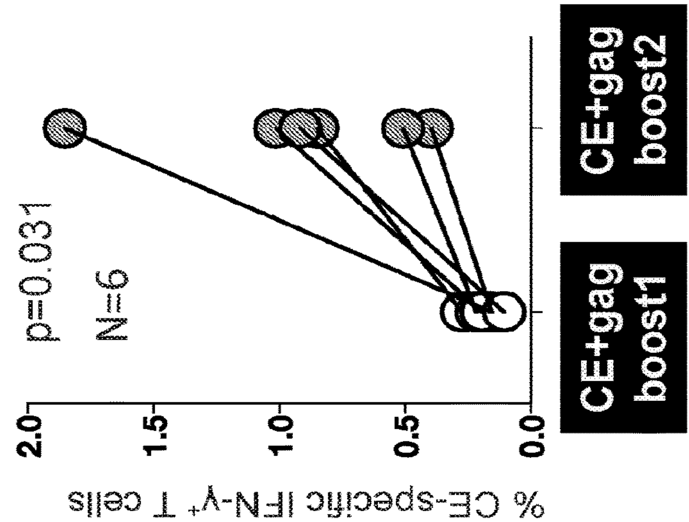
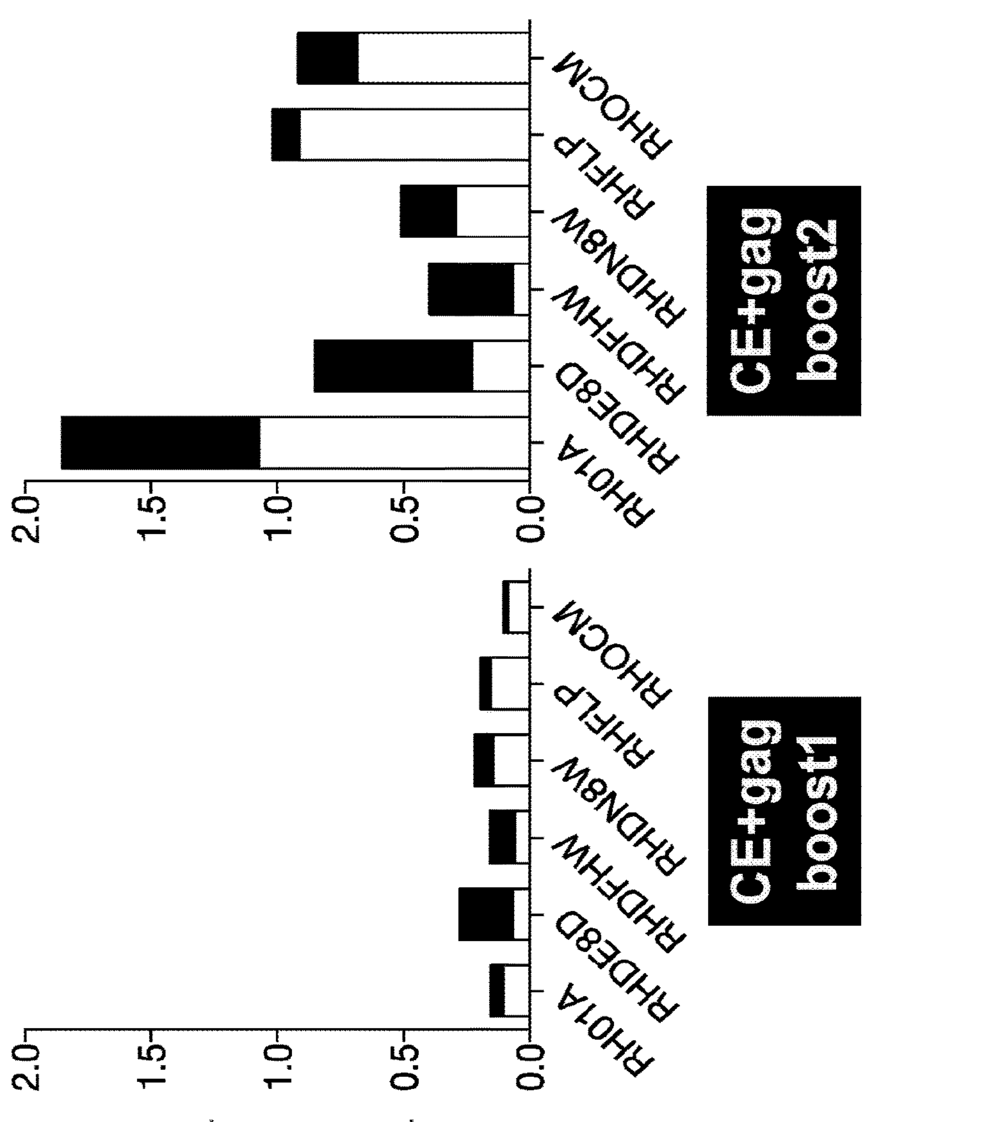
Figure 5

| DNA Boost Regimen of CE-primed macaques | Animal | Response to individual CE | | | | | | | Positive CE/animal | |
|---|---|---|---|---|---|---|---|---|---|---|
| | | CE1 | CE2 | CE3 | CE4 | CE5 | CE6 | CE7 | # | Range |
| None (N=14) | T129 | | | + | | | | | 1 | 1 to 4 |
| | T136 | | | + | | + | + | | 3 | |
| | T137 | | | | | + | + | | 2 | |
| | T143 | | | | + | + | | | 2 | |
| | T144 | | + | + | | + | + | | 4 | |
| | T148 | + | | | | | | | 1 | |
| | T150 | | | | | + | | + | 2 | |
| | T152 | | | + | + | + | | | 3 | |
| | L986* | | | | | + | + | | 2 | |
| | R108* | | | | | + | + | | 2 | |
| | R677* | | | + | | | | | 1 | |
| | R682* | | | + | | + | + | | 3 | |
| | R683* | | | + | | + | | | 2 | |
| | R684* | | + | | | + | | | 2 | |
| gag (N=6) | L986* | | | | | + | + | | 2 | 1 to 3 |
| | R108* | | | | | + | + | | 2 | |
| | R677* | | | + | | | | | 1 | |
| | R682* | | | + | | + | + | | 3 | |
| | R683* | | | + | | + | | | 2 | |
| | R684* | | + | + | | + | | | 3 | |
| CE&gag co-delivery (N=6) | 01A | + | + | + | | + | + | + | 6 | 2 to 6 |
| | DE8D | | | + | | + | | | 2 | |
| | DFHW | + | + | + | | + | | | 4 | |
| | DN8W | + | | + | | + | + | | 4 | |
| | FLP | | + | + | + | + | | | 4 | |
| | OCM | | + | + | | + | + | + | 5 | |

Figure 7
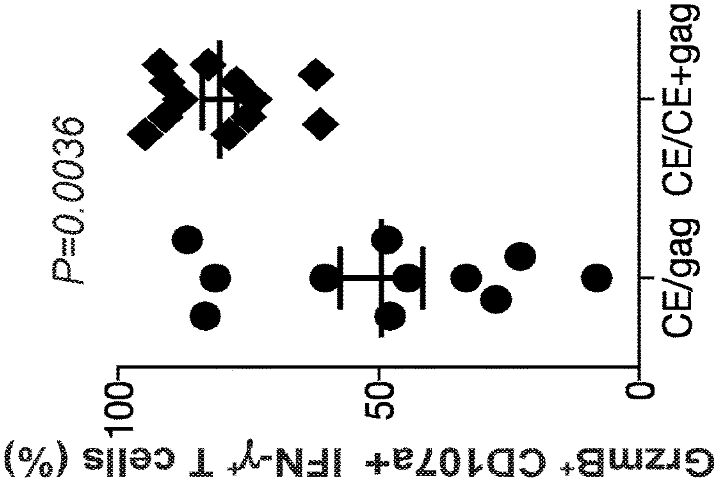
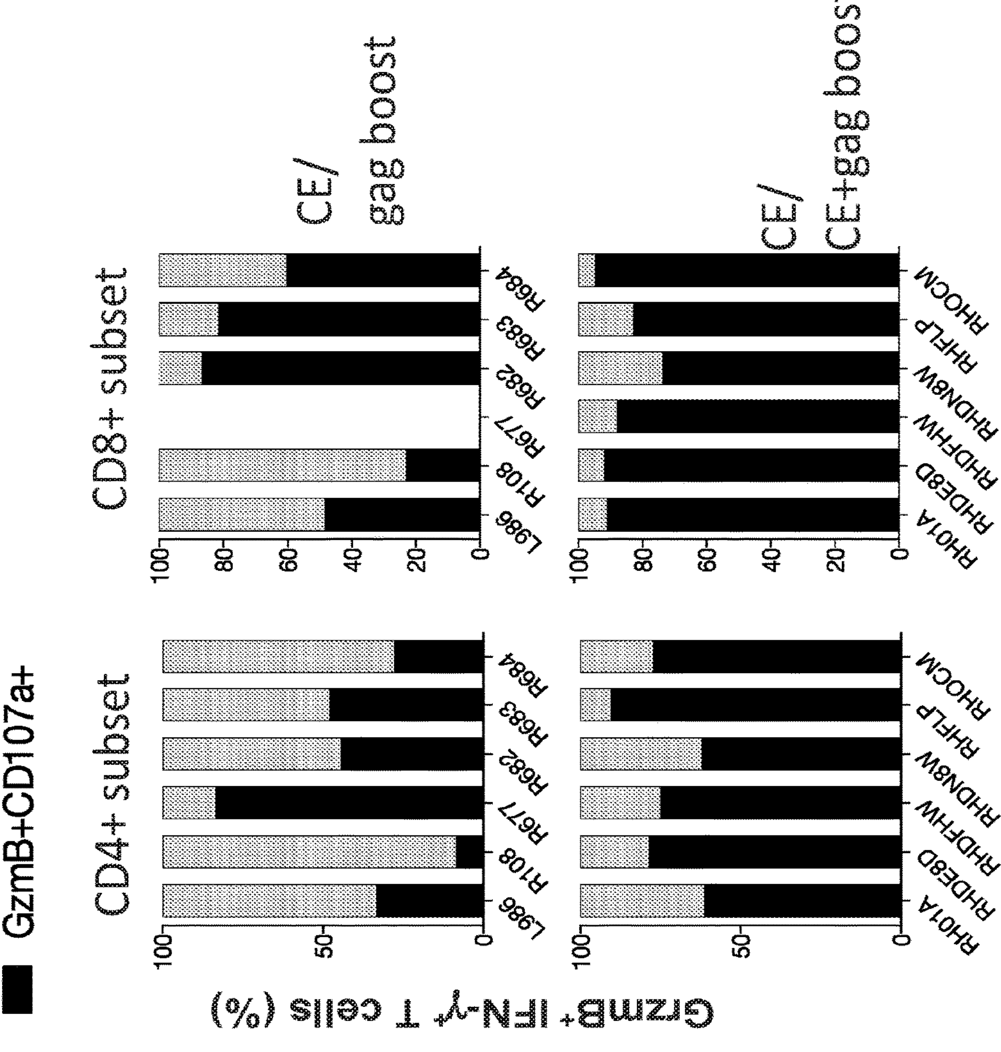

Schematic of the p24CE1/2 plasmid DNA (plasmid code 306H)

Schematic of the p55$^{gag}$ plasmid DNA (plasmid code 114H)

Vaccination of Naïve Macaques (N=4) with HIV Env-CE DNA
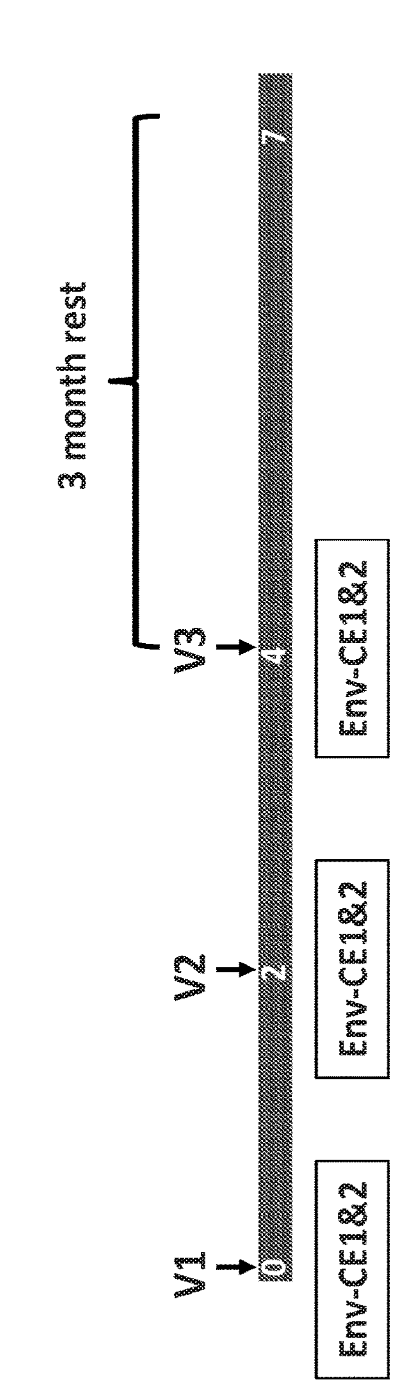
Vaccine: mixture of HIV Env1&2 DNA adjuvanted with macaque IL-12 DNA and delivered intramuscular route followed by *in vivo* electroporation
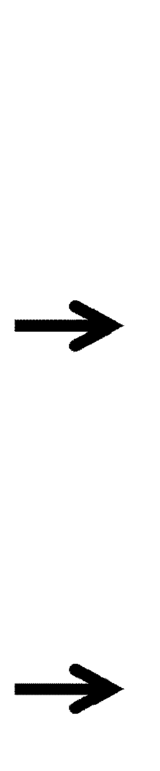
Analysis of CE-specific immune responses in blood at 2 weeks after V2 and V3 and after a rest period of 3 months
Figure 11

Env-CE DNA Vaccine Induces Memory T Cell Responses

Methods: PBMC were incubated with peptide pools spanning all 12 CE and % CE-specific IFN-γ producing CD4 and CD8 central memory (CM; $CD28^{+}CD95^{+}$) and effector memory (EM; CD28-$CD95^{+}$) T cells were determined following peptide stimulation

Env-CE DNA Vaccination Induces CE-specific Responses with a Significant Fraction of CD8⁺ T Cells (Granzyme B⁺ and CD107a⁺)

Methods: PBMC were incubated with peptide pools spanning all 12 CE. % IFN-γ producing CE-specific CD4 and CD8 T cells harboring Granzyme B⁺ and expressing CD107a⁺ was determined following peptide stimulation

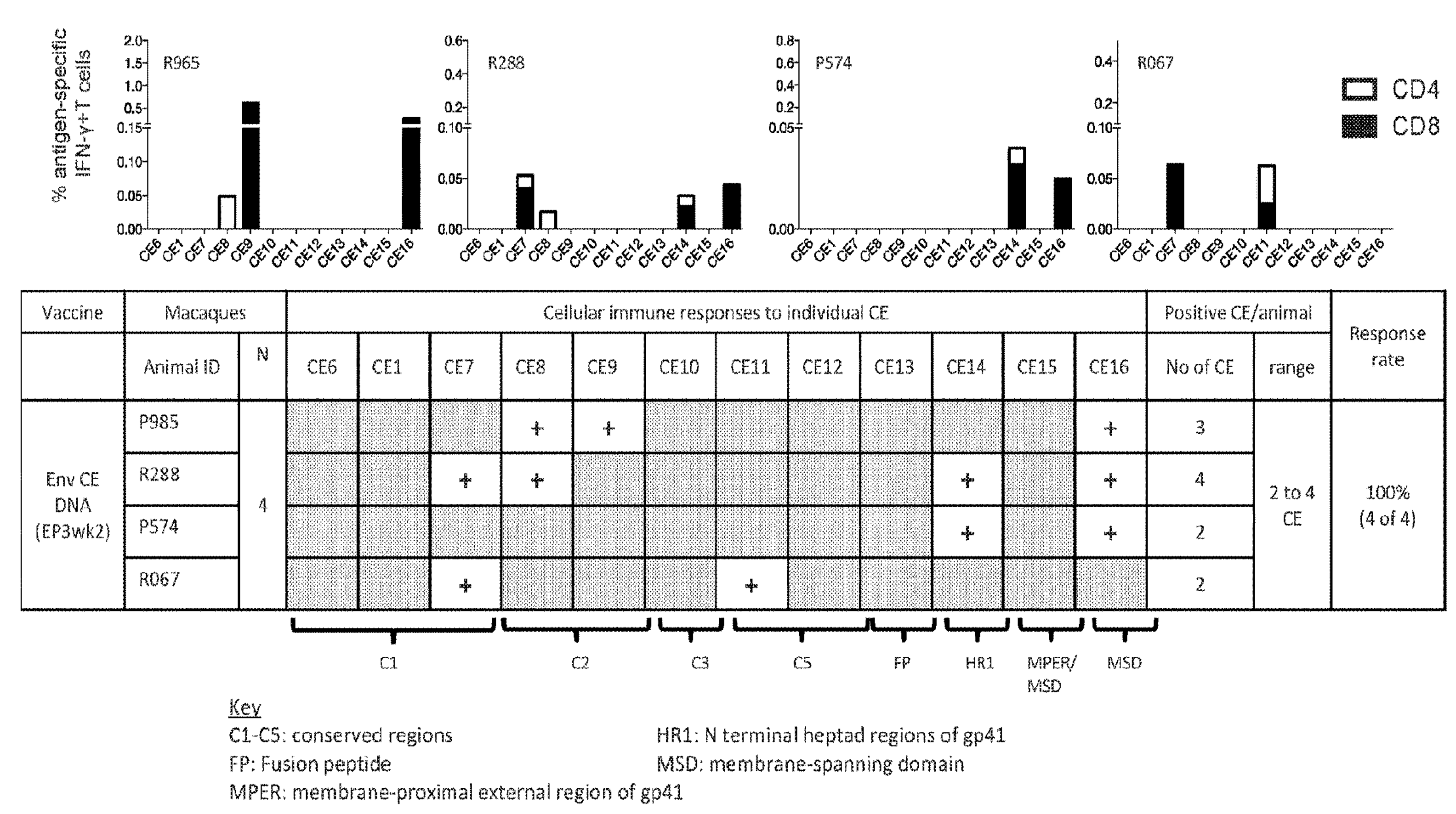

| Vaccine | Macaques | | Cellular immune responses to individual CE | | | | | | | | | | | | Positive CE/animal | | Response rate |
|---|---|---|---|---|---|---|---|---|---|---|---|---|---|---|---|---|---|
| | Animal ID | N | CE6 | CE1 | CE7 | CE8 | CE9 | CE10 | CE11 | CE12 | CE13 | CE14 | CE15 | CE16 | No of CE | range | |
| Env CE DNA (EP3wk2) | P985 | 4 | | | | + | + | | | | | | | + | 3 | 2 to 4 CE | 100% (4 of 4) |
| | R288 | | | | + | + | | | | | | + | | + | 4 | | |
| | P574 | | | | | | | | | | | + | | + | 2 | | |
| | R067 | | | | + | | | | + | | | | | | 2 | | |

Methods: PBMC were incubated with individual peptide pools spanning the 12 CE and % CE-specific CD4 and CD8 cells producing IFN-γ were determined following peptide stimulation Result: Recognition of 2-4 CE per animal. Six of the CE are immunogenic in the 4 animals analyzed (CE6, CE1, CE10, CE12, CE13, CE15 did not develop cellular responses)

Figure 15

| Vaccine | Macaques: Animal ID | N | CE6 | CD1 | CE7 | CE8 | CE9 | CE10 | CE11 | CE12 | CE13 | CE14 | CE15 | CE16 | Positive CE/animal: No of CE | range | Response rate |
|---|---|---|---|---|---|---|---|---|---|---|---|---|---|---|---|---|---|
| Env DNA | P909 | 9 | | | | | | | | | | + | | | 1 | 0 to 2 CE | 55% (5 of 9) |
| | P914 | | | | | | | | | | | | | | 1 | | |
| | P917 | | | | | | | | | | | | | | 0 | | |
| | P919 | | | | | | | | | | | | | | 0 | | |
| | P923 | | | | | | | | | | | | | | 0 | | |
| | P929 | | | | | | | | | | | + | | | 1 | | |
| | P934 | | | | | | | | | | | + | | | 1 | | |
| | P937 | | | | | | | | | | | + | | | 1 | | |
| | P941 | | | | | | + | + | | | | | | | 2 | | |

Prime boost vaccination using
HIV Env-CE as prime and Env DNA as boost

The boost was a mixture of env DNA composed of clade B Bal and 6101 and clade C 1086 env DNA covering all of the 24 CE sequences present in HIV Env CE1 and CE2 proteins.
The intact Env molecule produced (gp145) lacks the immunodominant loop in the extracellular portion of gp41.

Env-CE Primed Responses are Boosted upon Vaccination with Intact Env

Comparison of Responses to Individual CE before and after the boost with pDNA plasmids expressing intact Env

| | | | Cellular immune responses to individual CE | | | | | | | | | | | | Positive CE/animal |
|---|---|---|---|---|---|---|---|---|---|---|---|---|---|---|---|
| CE # | | | CE1 | CE6 | CE7 | CE8 | CE9 | CE10 | CE11 | CE12 | CE13 | CE14 | CE15 | CE16 | No of CE |
| AA/CE | | | 14 | 11 | 21 | 15 | 23 | 21 | 12 | 12 | 14 | 43 | 20 | 14 | |
| Animal ID# | L985 | prime | | | | + | + | | | | | | | + | 3 |
| | | boost1 | | | | + | + | | | | | +* | | + | 4 |
| | | boost2 | | | | + | + | | | | | +* | | + | 4 |
| | R288 | prime | | | + | + | | | | | | + | | + | 4 |
| | | boost1 | | | + | + | | | | | | + | | + | 4 |
| | | boost2 | | | + | + | | | | | | + | | + | 4 |
| | P574 | prime | | | | | | | | | | + | | + | 2 |
| | | boost1 | | | | | | | +* | | | + | | + | 3 |
| | | boost2 | | | +* | | | | +* | | +* | + | | + | 5 |
| | R067 | prime | | | + | | | | + | | | | | | 2 |
| | | boost1 | | | + | | | | + | | | +* | | | 3 |
| | | boost2 | | | + | +* | | | + | | | +* | | | 4 |

Few new responses were detected after the boost (*), which could be recall responses present at levels below threshold after DNA vaccination or *de novo* responses induced by intact env vaccine boost

Figure 19

Env-CE DNA Vaccine induces Antibody that Can Recognize gp120 Env by ELISA (HIV-1 IIIB)

Methods: Proteins from cells transfected with HIV env-CE1 DNA or HIV env-CE2 DNA were separated on denaturing gels and transferred onto membranes. Individual strips of membranes were incubated with plasma (1:100 dilution) from the vaccinated macaques and visualized using standard western blot methodology.

Antibodies Induced by the HIV Env-CE Vaccine Recognize Intact HIV Env Proteins from HIV clade B and clade C Methods: gp145 protein from transfected cells was separated on denaturing acrylamide gels and transferred onto membranes. Membranes were then incubated with plasma from macaques primed using env-CE DNA and boosted with intact env DNA.

Initial and Alternative HIV p24 Gag CE

| CE1_147-158 | CE2_168-185 | CE3_191-214 | CE4_231-249 | CE5_262-282 | CE6_296-309 | CE7_343-359 |
|---|---|---|---|---|---|---|
| ISPRTLNAWVKV (SEQ ID NO:26) | VIPMFSALSEGATPQDLN (SEQ ID NO:27) | VGGHQAAMQMLKDTINEEAAEWDR (SEQ ID NO:28) | PRGSDIAGTTSTLQEQIGW (SEQ ID NO:29) | KRWIILGLNKIVRMYSPTSI (SEQ ID NO:30) | YVDRFYKTLRAEQA (SEQ ID NO:31) | LEEMMTACQGVGGPGHK (SEQ ID NO:32) |
| LSPRTLNAWVKV (SEQ ID NO:33) | VIPMFTALSEGATPQDLN (SEQ ID NO:34) | VGGHQAAMQMLKETINEEAAEWDR (SEQ ID NO:35) | PRGSDIAGTTSTLQEQIAW (SEQ ID NO:36) | KRWIILGLNKIVRMYSPVSI (SEQ ID NO:37) | YVDRFFKTLRAEQA (SEQ ID NO:38) | LEEMMTACQGVGGPSHK (SEQ ID NO:39) |

| CE8_143-185 | CE9_160-189 | CE10_231-253 | CE11_281-309 | CE12_324-338 | CE13_343-367 |
|---|---|---|---|---|---|
| QPISPRTLNAWVKV (SEQ ID NO:57) | EEKAFSPEVIPMFSALSEGATPQDLNTMLN (SEQ ID NO:59) | PRGSDIAGTTSTLQEQIGWMT (SEQ ID NO:61) | SILDIRQGPKEPFRDYVDRF (SEQ ID NO:63) | QNSNPDCKTILKALG (SEQ ID NO:65) | LEEMMTACQGVGGPGHKARILAEAM (SEQ ID NO:67) |
| QALSPRTLNAWVKV (SEQ ID NO:58) | EEKGFNPEVIPMFTALSEGATPQDLNMMLN (SEQ ID NO:60) | PRGSDIAGTTSTLQEQIAWMT (SEQ ID NO:62) | SILDIKQGPKEPFRDYVDRF (SEQ ID NO:64) | QNANPDCKTILKALG (SEQ ID NO:66) | LEEMMTACQGVGGPSHKARVLAEAM (SEQ ID NO:68) |

Initial CE are indicated in clear boxes with amino acid positions within the Gag protein indicated (using HXB2 as reference)
Alternate CE are indicated in shaded boxes
Toggle sites are shaded
All AA residues are within the p24 protein except the last 4 AA, which are from the p2 protein Notes:

- CE8 may replace CE1: Captures additional epitope
- CE9 may replace CE2: Captures favorable epitopes at N- and C-terminal ends
- CE10 may replace CE4: Potential increase in immunogenicity by extending C-terminus
- CE11 may be included due to strong conservation and structurally vulnerable sites.
- CE12 captures structurally vulnerable sites
- CE13 may be able to replace CE7: Captures additional epitope and extends into p2 protein

Figure 23

Initial and Alternative HIV p24 Env CE

N-terminus

CE6_36-46
WVTVYYGVPVW (SEQ ID NO:1)

CE1_66-79
HNVWATHACVPTDP (SEQ ID NO:2)
HNIWATHACVPTDP (SEQ ID NO:3)

CE7_109-129
ISLWDQSLKPCVKLTPLCVTL (SEQ ID NO:4)
ISLWDESLKPCVKLTPLCVTL (SEQ ID NO:5)

CE8_212-224
FEPIPIHYCTPAGFA (SEQ ID NO:6)
FDPIPIHYCAPAGYA (SEQ ID NO:7)

CE9_245-267
VQCTHGIRPVVSTQLLLNGSLAE (SEQ ID NO:8)
VQCTHGIKPVVSTQLLLNGSLAE (SEQ ID NO:9)

CE10_365-385
SGGDPEIVMHSFNCGGEFFYC (SEQ ID NO:10)
AGGDLEITTHSFNCRGEFFYC (SEQ ID NO:11)

CE17_214-228
PIPIHYCAPAGFAILKC (SEQ ID NO:70)
PIPIHYCTPAGYAILKC (SEQ ID NO:71)

CE18_241-267
NVSTVQCTHGIRPVVSTQLLLNGSLAE (SEQ ID NO:72)
NVSSVQCTHGIKPVVSTQLLLNGSLAE (SEQ ID NO:73)

CE19_366-385
GGDPEIVMHTFNCGGEFFYC (SEQ ID NO:74)
GGDLEITTHSFNCRGEFFYC (SEQ ID NO:75)

CE20_412-423
CRIKQIINMWQ (SEQ ID NO:76)
CKIRQIVNRWQ (SEQ ID NO:77)

CE11_477-485
DNWRSELYKYKVV (SEQ ID NO:12)
NNWRSELYKYKVV (SEQ ID NO:13)

CE12_501-512
ARRRVVQREKRA (SEQ ID NO:14)
AKRRVVEREKRA (SEQ ID NO:15)

CE13_521-534
GFLGTAGSTMGAAS (SEQ ID NO:16)
GFLGAAGSTMGAAS (SEQ ID NO:17)

CE14_537-579
LTVQARLLLSGIVQQQNNLLRAIEAQQHLLQLTVWGIKQLQAR (SEQ ID NO:18)
LTVQARQLLSGIVQQQSNLLKAIEAQQHMLQLTVWGIKQLQTR (SEQ ID NO:19)

CE15_672-699
WLWYIKIFIMIVGGLVGLRI (SEQ ID NO:20)
WLWYIRIFIMIVGGLIGLRI (SEQ ID NO:21)

CE16_707-719
RVRKGYSPLSLQT (SEQ ID NO:20)
RVRQGYSPLSFQT (SEQ ID NO:21)

CE21_472-485
GGDMRDNWRSELYKYKVV (SEQ ID NO:78)
GGNMKDNWRSELYKYKVV (SEQ ID NO:79)

CE22_537-582
LTVQARLLLSGIVQQQNNLLRAIEAQQHLLQLTVWGIKQLQARVLA (SEQ ID NO:80)
LTVQARQLLSGIVQQQSNLLKAIEAQQHMLQLTVWGIKQLQTRVLA (SEQ ID NO:81)

CE23_602-617
DQQLLGIWGCSGKLIC (SEQ ID NO:82)
DQQLLGLWGCSGKLIC (SEQ ID NO:83)

CE23_602-617
WLWYIKIFIMIVGGLVGLRI (SEQ ID NO:84)
WLWYIRIFIMIVGGLIGLRI (SEQ ID NO:85)

C-terminus

CE are listed from the N-terminal to C-terminal ends of the gp160 Env protein. Slashes indicate that distances between CE are truncated. Initial CE are indicated in clear boxes with AA positions within the Env protein indicated (using HXB2 as reference)
Alternate CE are indicated in shaded boxes
Toggle sites are shaded

- CE17 may replace CE8
- CE18 may replace CE9: Captures additional epitope at N-terminus
- CE19 may replace CE10: Removes toggle site at N-terminus, adds internal toggle site
- CE20 captures a favorable epitope and a structurally vulnerable site
- CE21 may replace CE11: captures an additional epitope and a structurally vulnerable site
- CE22 may replace CE14: captures an additional epitope
- CE23 captures additional epitopes
- CE24 may replace CE15: removes a toggle site but retains epitopes

Figure 24

SEQUENCE LISTING

```
Sequence total quantity: 89
SEQ ID NO: 1            moltype = AA  length = 11
FEATURE                 Location/Qualifiers
REGION                  1..11
                        note = synthetic peptide construct
source                  1..11
                        mol_type = protein
                        organism = synthetic construct
SEQUENCE: 1
WVTVYYGVPV W                                                          11

SEQ ID NO: 2            moltype = AA  length = 14
FEATURE                 Location/Qualifiers
REGION                  1..14
                        note = synthetic peptide construct
source                  1..14
                        mol_type = protein
                        organism = synthetic construct
SEQUENCE: 2
HNVWATHACV PTDP                                                       14

SEQ ID NO: 3            moltype = AA  length = 14
FEATURE                 Location/Qualifiers
REGION                  1..14
                        note = synthetic peptide construct
source                  1..14
                        mol_type = protein
                        organism = synthetic construct
SEQUENCE: 3
HNIWATHACV PTDP                                                       14

SEQ ID NO: 4            moltype = AA  length = 21
FEATURE                 Location/Qualifiers
REGION                  1..21
                        note = synthetic peptide construct
source                  1..21
                        mol_type = protein
                        organism = synthetic construct
SEQUENCE: 4
ISLWDQSLKP CVKLTPLCVT L                                               21

SEQ ID NO: 5            moltype = AA  length = 21
FEATURE                 Location/Qualifiers
REGION                  1..21
                        note = synthetic peptide construct
source                  1..21
                        mol_type = protein
                        organism = synthetic construct
SEQUENCE: 5
ISLWDESLKP CVKLTPLCVT L                                               21

SEQ ID NO: 6            moltype = AA  length = 15
FEATURE                 Location/Qualifiers
REGION                  1..15
                        note = synthetic peptide construct
source                  1..15
                        mol_type = protein
                        organism = synthetic construct
SEQUENCE: 6
FEPIPIHYCT PAGFA                                                      15
```

```
SEQ ID NO: 7            moltype = AA  length = 15
FEATURE                 Location/Qualifiers
REGION                  1..15
                        note = synthetic peptide construct
source                  1..15
                        mol_type = protein
                        organism = synthetic construct
SEQUENCE: 7
FDPIPIHYCA PAGYA                                                    15

SEQ ID NO: 8            moltype = AA  length = 23
FEATURE                 Location/Qualifiers
REGION                  1..23
                        note = synthetic peptide construct
source                  1..23
                        mol_type = protein
                        organism = synthetic construct
SEQUENCE: 8
VQCTHGIRPV VSTQLLLNGS LAE                                           23

SEQ ID NO: 9            moltype = AA  length = 23
FEATURE                 Location/Qualifiers
REGION                  1..23
                        note = synthetic peptide construct
source                  1..23
                        mol_type = protein
                        organism = synthetic construct
SEQUENCE: 9
VQCTHGIKPV VSTQLLLNGS LAE                                           23

SEQ ID NO: 10           moltype = AA  length = 21
FEATURE                 Location/Qualifiers
REGION                  1..21
                        note = synthetic peptide construct
source                  1..21
                        mol_type = protein
                        organism = synthetic construct
SEQUENCE: 10
SGGDPEIVMH SFNCGGEFFY C                                             21

SEQ ID NO: 11           moltype = AA  length = 21
FEATURE                 Location/Qualifiers
REGION                  1..21
                        note = synthetic peptide construct
source                  1..21
                        mol_type = protein
                        organism = synthetic construct
SEQUENCE: 11
AGGDLEITTH SFNCRGEFFY C                                             21

SEQ ID NO: 12           moltype = AA  length = 13
FEATURE                 Location/Qualifiers
REGION                  1..13
                        note = synthetic peptide construct
source                  1..13
                        mol_type = protein
                        organism = synthetic construct
SEQUENCE: 12
DNWRSELYKY KVV                                                      13

SEQ ID NO: 13           moltype = AA  length = 13
FEATURE                 Location/Qualifiers
REGION                  1..13
                        note = synthetic peptide construct
source                  1..13
                        mol_type = protein
                        organism = synthetic construct
SEQUENCE: 13
NNWRSELYKY KVV                                                      13

SEQ ID NO: 14           moltype = AA  length = 12
FEATURE                 Location/Qualifiers
REGION                  1..12
                        note = synthetic peptide construct
source                  1..12
                        mol_type = protein
                        organism = synthetic construct
SEQUENCE: 14
ARRRVVQREK RA                                                       12
```

```
SEQ ID NO: 15          moltype = AA  length = 12
FEATURE                Location/Qualifiers
REGION                 1..12
                       note = synthetic peptide construct
source                 1..12
                       mol_type = protein
                       organism = synthetic construct
SEQUENCE: 15
AKRRVVEREK RA                                                      12

SEQ ID NO: 16          moltype = AA  length = 14
FEATURE                Location/Qualifiers
REGION                 1..14
                       note = synthetic peptide construct
source                 1..14
                       mol_type = protein
                       organism = synthetic construct
SEQUENCE: 16
GFLGTAGSTM GAAS                                                    14

SEQ ID NO: 17          moltype = AA  length = 14
FEATURE                Location/Qualifiers
REGION                 1..14
                       note = synthetic peptide construct
source                 1..14
                       mol_type = protein
                       organism = synthetic construct
SEQUENCE: 17
GFLGAAGSTM GAAS                                                    14

SEQ ID NO: 18          moltype = AA  length = 43
FEATURE                Location/Qualifiers
REGION                 1..43
                       note = synthetic peptide construct
source                 1..43
                       mol_type = protein
                       organism = synthetic construct
SEQUENCE: 18
LTVQARLLLS GIVQQQNNLL RAIEAQQHLL QLTVWGIKQL QAR                    43

SEQ ID NO: 19          moltype = AA  length = 43
FEATURE                Location/Qualifiers
REGION                 1..43
                       note = synthetic peptide construct
source                 1..43
                       mol_type = protein
                       organism = synthetic construct
SEQUENCE: 19
LTVQARQLLS GIVQQQSNLL KAIEAQQHML QLTVWGIKQL QTR                    43

SEQ ID NO: 20          moltype = AA  length = 20
FEATURE                Location/Qualifiers
REGION                 1..20
                       note = synthetic peptide construct
source                 1..20
                       mol_type = protein
                       organism = synthetic construct
SEQUENCE: 20
WLWYIKIFIM IVGGLVGLRI                                              20

SEQ ID NO: 21          moltype = AA  length = 20
FEATURE                Location/Qualifiers
REGION                 1..20
                       note = synthetic peptide construct
source                 1..20
                       mol_type = protein
                       organism = synthetic construct
SEQUENCE: 21
WLWYIRIFIM IVGGLIGLRI                                              20

SEQ ID NO: 22          moltype = AA  length = 13
FEATURE                Location/Qualifiers
REGION                 1..13
                       note = synthetic peptide construct
source                 1..13
                       mol_type = protein
                       organism = synthetic construct
SEQUENCE: 22
```

```
RVRKGYSPLS LQT                                                   13

SEQ ID NO: 23           moltype = AA  length = 13
FEATURE                 Location/Qualifiers
REGION                  1..13
                        note = synthetic peptide construct
source                  1..13
                        mol_type = protein
                        organism = synthetic construct
SEQUENCE: 23
RVRQGYSPLS FQT                                                   13

SEQ ID NO: 24           moltype = AA  length = 253
FEATURE                 Location/Qualifiers
REGION                  1..253
                        note = synthetic peptide construct
source                  1..253
                        mol_type = protein
                        organism = synthetic construct
SEQUENCE: 24
WVTVYYGVPV WAAVHNVWAT HACVPTDPAA EISLWDQSLK PCVKLTPLCV TLGAKFEPIP  60
IHYCTPAGFA GAKVQCTHGI RPVVSTQLLL NGSLAEAADS GGDPEIVMHS FNCGGEFFYC  120
GAKDNWRSEL YKYKVVAAKA RRRVVQREKR AGAVGFLGTA GSTMGAASVA VLTVQARLLL  180
SGIVQQQNNL LRAIEAQQHL LQLTVWGIKQ LQARAADWLW YIKIFIMIVG GLVGLRIAAF  240
RVRKGYSPLS LQT                                                   253

SEQ ID NO: 25           moltype = AA  length = 253
FEATURE                 Location/Qualifiers
REGION                  1..253
                        note = synthetic peptide construct
source                  1..253
                        mol_type = protein
                        organism = synthetic construct
SEQUENCE: 25
WVTVYYGVPV WAAVHNIWAT HACVPTDPAA EISLWDESLK PCVKLTPLCV TLGAKFDPIP  60
IHYCAPAGYA GAKVQCTHGI KPVVSTQLLL NGSLAEAADA GGDLEITTHS FNCRGEFFYC  120
GAKNNWRSEL YKYKVVAAKA KRRVVEREKR AGAVGFLGAA GSTMGAASVA VLTVQARQLL  180
SGIVQQQSNL LKAIEAQQHM LQLTVWGIKQ LQTRAADWLW YIRIFIMIVG GLIGLRIAAF  240
RVRQGYSPLS FQT                                                   253

SEQ ID NO: 26           moltype = AA  length = 12
FEATURE                 Location/Qualifiers
REGION                  1..12
                        note = synthetic peptide construct
source                  1..12
                        mol_type = protein
                        organism = synthetic construct
SEQUENCE: 26
ISPRTLNAWV KV                                                    12

SEQ ID NO: 27           moltype = AA  length = 18
FEATURE                 Location/Qualifiers
REGION                  1..18
                        note = synthetic peptide construct
source                  1..18
                        mol_type = protein
                        organism = synthetic construct
SEQUENCE: 27
VIPMFSALSE GATPQDLN                                              18

SEQ ID NO: 28           moltype = AA  length = 24
FEATURE                 Location/Qualifiers
REGION                  1..24
                        note = synthetic peptide construct
source                  1..24
                        mol_type = protein
                        organism = synthetic construct
SEQUENCE: 28
VGGHQAAMQM LKDTINEEAA EWDR                                       24

SEQ ID NO: 29           moltype = AA  length = 19
FEATURE                 Location/Qualifiers
REGION                  1..19
                        note = synthetic peptide construct
source                  1..19
                        mol_type = protein
                        organism = synthetic construct
SEQUENCE: 29
PRGSDIAGTT STLQEQIGW                                             19
```

```
SEQ ID NO: 30           moltype = AA  length = 20
FEATURE                 Location/Qualifiers
REGION                  1..20
                        note = synthetic peptide construct
source                  1..20
                        mol_type = protein
                        organism = synthetic construct
SEQUENCE: 30
KRWIILGLNK IVRMYSPTSI                                            20

SEQ ID NO: 31           moltype = AA  length = 14
FEATURE                 Location/Qualifiers
REGION                  1..14
                        note = synthetic peptide construct
source                  1..14
                        mol_type = protein
                        organism = synthetic construct
SEQUENCE: 31
YVDRFYKTLR AEQA                                                  14

SEQ ID NO: 32           moltype = AA  length = 17
FEATURE                 Location/Qualifiers
REGION                  1..17
                        note = synthetic peptide construct
source                  1..17
                        mol_type = protein
                        organism = synthetic construct
SEQUENCE: 32
LEEMMTACQG VGGPGHK                                               17

SEQ ID NO: 33           moltype = AA  length = 12
FEATURE                 Location/Qualifiers
REGION                  1..12
                        note = synthetic peptide construct
source                  1..12
                        mol_type = protein
                        organism = synthetic construct
SEQUENCE: 33
LSPRTLNAWV KV                                                    12

SEQ ID NO: 34           moltype = AA  length = 18
FEATURE                 Location/Qualifiers
REGION                  1..18
                        note = synthetic peptide construct
source                  1..18
                        mol_type = protein
                        organism = synthetic construct
SEQUENCE: 34
VIPMFTALSE GATPQDLN                                              18

SEQ ID NO: 35           moltype = AA  length = 24
FEATURE                 Location/Qualifiers
REGION                  1..24
                        note = synthetic peptide construct
source                  1..24
                        mol_type = protein
                        organism = synthetic construct
SEQUENCE: 35
VGGHQAAMQM LKETINEEAA EWDR                                       24

SEQ ID NO: 36           moltype = AA  length = 19
FEATURE                 Location/Qualifiers
REGION                  1..19
                        note = synthetic peptide construct
source                  1..19
                        mol_type = protein
                        organism = synthetic construct
SEQUENCE: 36
PRGSDIAGTT STLQEQIAW                                             19

SEQ ID NO: 37           moltype = AA  length = 20
FEATURE                 Location/Qualifiers
REGION                  1..20
                        note = synthetic peptide construct
source                  1..20
                        mol_type = protein
                        organism = synthetic construct
SEQUENCE: 37
```

```
KRWIILGLNK IVRMYSPVSI                                        20

SEQ ID NO: 38          moltype = AA  length = 14
FEATURE                Location/Qualifiers
REGION                 1..14
                       note = synthetic peptide construct
source                 1..14
                       mol_type = protein
                       organism = synthetic construct
SEQUENCE: 38
YVDRFFKTLR AEQA                                              14

SEQ ID NO: 39          moltype = AA  length = 17
FEATURE                Location/Qualifiers
REGION                 1..17
                       note = synthetic peptide construct
source                 1..17
                       mol_type = protein
                       organism = synthetic construct
SEQUENCE: 39
LEEMMTACQG VGGPSHK                                           17

SEQ ID NO: 40          moltype = AA  length = 140
FEATURE                Location/Qualifiers
REGION                 1..140
                       note = synthetic peptide construct
source                 1..140
                       mol_type = protein
                       organism = synthetic construct
SEQUENCE: 40
VIPMFSALSE GATPQDLNAA VGGHQAAMQM LKDTINEEAA EWDRAAAEPR GSDIAGTTST  60
LQEQIGWAAA KRWIILGLNK IVRMYSPTSI AAKYVDRFYK TLRAEQAAGL EEMMTACQGV  120
GGPGHKAAIS PRTLNAWVKV                                        140

SEQ ID NO: 41          moltype = AA  length = 140
FEATURE                Location/Qualifiers
REGION                 1..140
                       note = synthetic peptide construct
source                 1..140
                       mol_type = protein
                       organism = synthetic construct
SEQUENCE: 41
VIPMFTALSE GATPQDLNAA VGGHQAAMQM LKETINEEAA EWDRAAAEPR GSDIAGTTST  60
LQEQIAWAAA KRWIILGLNK IVRMYSPVSI AAKYVDRFFK TLRAEQAAGL EEMMTACQGV  120
GGPSHKAALS PRTLNAWVKV                                        140

SEQ ID NO: 42          moltype = AA  length = 157
FEATURE                Location/Qualifiers
REGION                 1..157
                       note = synthetic peptide construct
source                 1..157
                       mol_type = protein
                       organism = synthetic construct
SEQUENCE: 42
MWLQSLLLLG TVACSISVIP MFSALSEGAT PQDLNAAVGG HQAAMQMLKD TINEEAAEWD  60
RAAAEPRGSD IAGTTSTLQE QIGWAAAKRW IILGLNKIVR MYSPTSIAAK YVDRFYKTLR  120
AEQAAGLEEM MTACQGVGGP GHKAAISPRT LNAWVKV                      157

SEQ ID NO: 43          moltype = AA  length = 157
FEATURE                Location/Qualifiers
REGION                 1..157
                       note = synthetic peptide construct
source                 1..157
                       mol_type = protein
                       organism = synthetic construct
SEQUENCE: 43
MWLQSLLLLG TVACSISVIP MFTALSEGAT PQDLNAAVGG HQAAMQMLKE TINEEAAEWD  60
RAAAEPRGSD IAGTTSTLQE QIAWAAAKRW IILGLNKIVR MYSPVSIAAK YVDRFFKTLR  120
AEQAAGLEEM MTACQGVGGP SHKAALSPRT LNAWVKV                      157

SEQ ID NO: 44          moltype = AA  length = 564
FEATURE                Location/Qualifiers
REGION                 1..564
                       note = synthetic peptide construct
source                 1..564
                       mol_type = protein
                       organism = synthetic construct
SEQUENCE: 44
MAPRSARRPL LLLLLLLLG LMHCASAAMF MVKNGNGTAC IMANFSAAFS VNYDTKSGPK  60
```

```
NMTLDLPSDA TVVLNRSSCG KENTSDPSLV IAFGRGHTLT LNFTRNATRY SVQLMSFVYN  120
LSDTHLFPNA SSKEIKTVES ITDIRADIDK KYRCVSGTQV HMNNVTVTLH DATIQAYLSN  180
SSFSRGETRC EQDRPSPTTA PPAPPSPSPS PVPKSPSVDK YNVSGTNGTC LLASMGLQLN  240
LTYERKDNTT VTRLLNINPN KTSASGSCGA HLVTLELHSE GTTVLLFQFG MNASSSRFFL  300
QGIQLNTILP DARDPAFKAA NGSLRALQAT VGNSYKCNAE EHVRVTKAFS VNIFKVWVQA  360
FKVEGGQFGS VEECLLDENS LEDIVIPMFS ALSEGATPQD LNAAVGGHQA AMQMLKDTIN  420
EEAAEWDRAA AEPRGSDIAG TTSTLQEQIG WAAAKRWIIL GLNKIVRMYS PTSIAAKYVD  480
RFYKTLRAEQ AAGLEEMMTA CQGVGGPGHK AAISPRTLNA WVKVGSEFTL IPIAVGGALA  540
GLVLIVLIAY LVGRKRSHAG YQTI                                         564

SEQ ID NO: 45          moltype = AA  length = 564
FEATURE                Location/Qualifiers
REGION                 1..564
                       note = synthetic peptide construct
source                 1..564
                       mol_type = protein
                       organism = synthetic construct
SEQUENCE: 45
MAPRSARRPL LLLLLLLLLG LMHCASAAMF MVKNGNGTAC IMANFSAAFS VNYDTKSGPK  60
NMTLDLPSDA TVVLNRSSCG KENTSDPSLV IAFGRGHTLT LNFTRNATRY SVQLMSFVYN  120
LSDTHLFPNA SSKEIKTVES ITDIRADIDK KYRCVSGTQV HMNNVTVTLH DATIQAYLSN  180
SSFSRGETRC EQDRPSPTTA PPAPPSPSPS PVPKSPSVDK YNVSGTNGTC LLASMGLQLN  240
LTYERKDNTT VTRLLNINPN KTSASGSCGA HLVTLELHSE GTTVLLFQFG MNASSSRFFL  300
QGIQLNTILP DARDPAFKAA NGSLRALQAT VGNSYKCNAE EHVRVTKAFS VNIFKVWVQA  360
FKVEGGQFGS VEECLLDENS LEDIVIPMFT ALSEGATPQD LNAAVGGHQA AMQMLKETIN  420
EEAAEWDRAA AEPRGSDIAG TTSTLQEQIA WAAAKRWIIL GLNKIVRMYS PVSIAAKYVD  480
RFFKTLRAEQ AAGLEEMMTA CQGVGGPSHK AALSPRTLNA WVKVGSEFTL IPIAVGGALA  540
GLVLIVLIAY LVGRKRSHAG YQTI                                         564

SEQ ID NO: 46          moltype = AA  length = 157
FEATURE                Location/Qualifiers
REGION                 1..157
                       note = synthetic peptide construct
source                 1..157
                       mol_type = protein
                       organism = synthetic construct
SEQUENCE: 46
MWLQSLLLLG TVACSISVIP MFTALSEGAT PQDLNAAVGG HQAAMQMLKE TINEEAAEWD  60
RAAAEPRGSD IAGTTSTLQE QIAWAAAKRW IILGLNKIVR MYSPVSIAAK YVDRFFKTLR  120
AEQAAGLEEM MTACQGVGGP SHKAALSPRT LNAWVKV                            157

SEQ ID NO: 47          moltype = AA  length = 249
FEATURE                Location/Qualifiers
REGION                 1..249
                       note = synthetic peptide construct
source                 1..249
                       mol_type = protein
                       organism = synthetic construct
SEQUENCE: 47
MWKPMPSPSN MKASAALLCL LLTAAAFSPQ GLAQPVGINT STTCCYRFIN KKIPKQRLES  60
YRRTTSSHCP REAVIFKTKL DKEICADPTQ KWVQDFMKHL DKKTQTPKLV IPMFSALSEG  120
ATPQDLNAAV GGHQAAMQML KDTINEEAAE WDRAAAEPRG SDIAGTTSTL QEQIGWAAAK  180
RWIILGLNKI VRMYSPTSIA AKYVDRFYKT LRAEQAAGLE EMMTACQGVG GPGHKAAISP  240
RTLNAWVKV                                                          249

SEQ ID NO: 48          moltype = AA  length = 249
FEATURE                Location/Qualifiers
REGION                 1..249
                       note = synthetic peptide construct
source                 1..249
                       mol_type = protein
                       organism = synthetic construct
SEQUENCE: 48
MWKPMPSPSN MKASAALLCL LLTAAAFSPQ GLAQPVGINT STTCCYRFIN KKIPKQRLES  60
YRRTTSSHCP REAVIFKTKL DKEICADPTQ KWVQDFMKHL DKKTQTPKLV IPMFTALSEG  120
ATPQDLNAAV GGHQAAMQML KETINEEAAE WDRAAAEPRG SDIAGTTSTL QEQIAWAAAK  180
RWIILGLNKI VRMYSPVSIA AKYVDRFFKT LRAEQAAGLE EMMTACQGVG GPSHKAALSP  240
RTLNAWVKV                                                          249

SEQ ID NO: 49          moltype = AA  length = 165
FEATURE                Location/Qualifiers
REGION                 1..165
                       note = synthetic peptide construct
source                 1..165
                       mol_type = protein
                       organism = synthetic construct
SEQUENCE: 49
MWLQSLLLLG TVACSISQGQ MVHQAISPRT LNAWVKVLAK EEKAFSPEVI PMFSALSEGA  60
TPQDLNAAKV GGHQAAMQML KETINEEAAE WDRAAAEPRG SDIAGTTSTL QEQIGWAAAK  120
```

```
RWIILGLNKI VRMYSPTSIA AKYVDRFYKT LRAEQADYKD DDDKL              165

SEQ ID NO: 50          moltype = AA  length = 20
FEATURE                Location/Qualifiers
REGION                 1..20
                       note = synthetic peptide construct
source                 1..20
                       mol_type = protein
                       organism = synthetic construct
SEQUENCE: 50
QGQMVHQAIS PRTLNAWVKV                                          20

SEQ ID NO: 51          moltype = AA  length = 26
FEATURE                Location/Qualifiers
REGION                 1..26
                       note = synthetic peptide construct
source                 1..26
                       mol_type = protein
                       organism = synthetic construct
SEQUENCE: 51
EEKAFSPEVI PMFSALSEGA TPQDLN                                   26

SEQ ID NO: 52          moltype = AA  length = 156
FEATURE                Location/Qualifiers
REGION                 1..156
                       note = synthetic peptide construct
source                 1..156
                       mol_type = protein
                       organism = synthetic construct
SEQUENCE: 52
MWLQSLLLLG TVACSISQGQ MVHQALSPRT LNAWVKVLAK EEKGFNPEVI PMFTALSEGA  60
TPQDLNAAKV GGHQAAMQML KDTINEEAAE WDRAAAEPRG SDIAGTTSTL QEQIAWAAAK  120
RWIILGLNKI VRMYSPVSIA AKYVDRFFKT LRAEQA                        156

SEQ ID NO: 53          moltype = AA  length = 155
FEATURE                Location/Qualifiers
REGION                 1..155
                       note = synthetic peptide construct
source                 1..155
                       mol_type = protein
                       organism = synthetic construct
SEQUENCE: 53
MWLQSLLLLG TVACSISEEK GFNPEVIPMF TALSEGATPQ DLNAAKVGGH QAAMQMLKDT  60
INEEAAEWDR AAAEPRGSDI AGTTSTLQEQ IAWAAAKRWI ILGLNKIVRM YSPVSIAAKY  120
VDRFFKTLRA EQAALQGQMV HQALSPRTLN AWVKV                         155

SEQ ID NO: 54          moltype = AA  length = 155
FEATURE                Location/Qualifiers
REGION                 1..155
                       note = synthetic peptide construct
source                 1..155
                       mol_type = protein
                       organism = synthetic construct
SEQUENCE: 54
MWLQSLLLLG TVACSISEEK AFSPEVIPMF SALSEGATPQ DLNAAKVGGH QAAMQMLKET  60
INEEAAEWDR AAAEPRGSDI AGTTSTLQEQ IGWAAAKRWI ILGLNKIVRM YSPTSIAAKY  120
VDRFYKTLRA EQAALQGQMV HQAISPRTLN AWVKV                         155

SEQ ID NO: 55          moltype = AA  length = 20
FEATURE                Location/Qualifiers
REGION                 1..20
                       note = synthetic peptide construct
source                 1..20
                       mol_type = protein
                       organism = synthetic construct
SEQUENCE: 55
QGQMVHQALS PRTLNAWVKV                                          20

SEQ ID NO: 56          moltype = AA  length = 26
FEATURE                Location/Qualifiers
REGION                 1..26
                       note = synthetic peptide construct
source                 1..26
                       mol_type = protein
                       organism = synthetic construct
SEQUENCE: 56
EEKGFNPEVI PMFTALSEGA TPQDLN                                   26

SEQ ID NO: 57          moltype = AA  length = 14
```

```
FEATURE                 Location/Qualifiers
REGION                  1..14
                        note = synthetic peptide construct
source                  1..14
                        mol_type = protein
                        organism = synthetic construct
SEQUENCE: 57
QPISPRTLNA WVKV                                                          14

SEQ ID NO: 58           moltype = AA  length = 14
FEATURE                 Location/Qualifiers
REGION                  1..14
                        note = synthetic peptide construct
source                  1..14
                        mol_type = protein
                        organism = synthetic construct
SEQUENCE: 58
QALSPRTLNA WVKV                                                          14

SEQ ID NO: 59           moltype = AA  length = 30
FEATURE                 Location/Qualifiers
REGION                  1..30
                        note = synthetic peptide construct
source                  1..30
                        mol_type = protein
                        organism = synthetic construct
SEQUENCE: 59
EEKAFSPEVI PMFSALSEGA TPQDLNTMLN                                         30

SEQ ID NO: 60           moltype = AA  length = 30
FEATURE                 Location/Qualifiers
REGION                  1..30
                        note = synthetic peptide construct
source                  1..30
                        mol_type = protein
                        organism = synthetic construct
SEQUENCE: 60
EEKGFNPEVI PMFTALSEGA TPQDLNMMLN                                         30

SEQ ID NO: 61           moltype = AA  length = 21
FEATURE                 Location/Qualifiers
REGION                  1..21
                        note = synthetic peptide construct
source                  1..21
                        mol_type = protein
                        organism = synthetic construct
SEQUENCE: 61
PRGSDIAGTT STLQEQIGWM T                                                  21

SEQ ID NO: 62           moltype = AA  length = 21
FEATURE                 Location/Qualifiers
REGION                  1..21
                        note = synthetic peptide construct
source                  1..21
                        mol_type = protein
                        organism = synthetic construct
SEQUENCE: 62
PRGSDIAGTT STLQEQIAWM T                                                  21

SEQ ID NO: 63           moltype = AA  length = 20
FEATURE                 Location/Qualifiers
REGION                  1..20
                        note = synthetic peptide construct
source                  1..20
                        mol_type = protein
                        organism = synthetic construct
SEQUENCE: 63
SILDIRQGPK EPFRDYVDRF                                                    20

SEQ ID NO: 64           moltype = AA  length = 20
FEATURE                 Location/Qualifiers
REGION                  1..20
                        note = synthetic peptide construct
source                  1..20
                        mol_type = protein
                        organism = synthetic construct
SEQUENCE: 64
SILDIKQGPK EPFRDYVDRF                                                    20
```

```
SEQ ID NO: 65           moltype = AA  length = 15
FEATURE                 Location/Qualifiers
REGION                  1..15
                        note = synthetic peptide construct
source                  1..15
                        mol_type = protein
                        organism = synthetic construct
SEQUENCE: 65
QNSNPDCKTI LKALG                                                  15

SEQ ID NO: 66           moltype = AA  length = 15
FEATURE                 Location/Qualifiers
REGION                  1..15
                        note = synthetic peptide construct
source                  1..15
                        mol_type = protein
                        organism = synthetic construct
SEQUENCE: 66
QNANPDCKTI LKALG                                                  15

SEQ ID NO: 67           moltype = AA  length = 25
FEATURE                 Location/Qualifiers
REGION                  1..25
                        note = synthetic peptide construct
source                  1..25
                        mol_type = protein
                        organism = synthetic construct
SEQUENCE: 67
LEEMMTACQG VGGPGHKARI LAEAM                                       25

SEQ ID NO: 68           moltype = AA  length = 25
FEATURE                 Location/Qualifiers
REGION                  1..25
                        note = synthetic peptide construct
source                  1..25
                        mol_type = protein
                        organism = synthetic construct
SEQUENCE: 68
LEEMMTACQG VGGPSHKARV LAEAM                                       25

SEQ ID NO: 69           moltype = AA  length = 401
FEATURE                 Location/Qualifiers
REGION                  1..401
                        note = synthetic peptide construct
source                  1..401
                        mol_type = protein
                        organism = synthetic construct
SEQUENCE: 69
MRVTEIRKSY QHWWRWGIML LGILMICNAE EKLWVTVYYG VPVWKEATTT LFCASDRKAY  60
DTEVHNVWAT HACVPTDPNP QEVELKNVTE NFNMWKNNMV EQMHEDIISL WDQSLKPCVK  120
LTPLCVTLNC TDLRNATNGN DTNTTSSSRG MVGGGEMKNC SFNITTNIRG KVQKEYALFY  180
KLDIAPIDNN SNNRYRLISC GAKFEPIPIH YCTPAGFAGA KVQCTHGIRP VVSTQLLLNG  240
SLAEAADSGG DPEIVMHSFN CGGEFFYCGA KDNWRSELYK YKVVAAKARR RVVQREKRAG  300
AVGFLGTAGS TMGAASVAVL TVQARLLLSG IVQQQNNLLR AIEAQQHLLQ LTVWGIKQLQ  360
ARAADWLWYI KIFIMIVGGL VGLRIAAFRV RKGYSPLSLQ T                     401

SEQ ID NO: 70           moltype = AA  length = 17
FEATURE                 Location/Qualifiers
REGION                  1..17
                        note = synthetic peptide construct
source                  1..17
                        mol_type = protein
                        organism = synthetic construct
SEQUENCE: 70
PIPIHYCAPA GFAILKC                                                17

SEQ ID NO: 71           moltype = AA  length = 17
FEATURE                 Location/Qualifiers
REGION                  1..17
                        note = synthetic peptide construct
source                  1..17
                        mol_type = protein
                        organism = synthetic construct
SEQUENCE: 71
PIPIHYCTPA GYAILKC                                                17

SEQ ID NO: 72           moltype = AA  length = 27
FEATURE                 Location/Qualifiers
REGION                  1..27
```

```
                        note = synthetic peptide construct
source                  1..27
                        mol_type = protein
                        organism = synthetic construct
SEQUENCE: 72
NVSTVQCTHG IRPVVSTQLL LNGSLAE                                        27

SEQ ID NO: 73           moltype = AA  length = 27
FEATURE                 Location/Qualifiers
REGION                  1..27
                        note = synthetic peptide construct
source                  1..27
                        mol_type = protein
                        organism = synthetic construct
SEQUENCE: 73
NVSSVQCTHG IKPVVSTQLL LNGSLAE                                        27

SEQ ID NO: 74           moltype = AA  length = 20
FEATURE                 Location/Qualifiers
REGION                  1..20
                        note = synthetic peptide construct
source                  1..20
                        mol_type = protein
                        organism = synthetic construct
SEQUENCE: 74
GGDPEIVMHT FNCGGEFFYC                                                20

SEQ ID NO: 75           moltype = AA  length = 20
FEATURE                 Location/Qualifiers
REGION                  1..20
                        note = synthetic peptide construct
source                  1..20
                        mol_type = protein
                        organism = synthetic construct
SEQUENCE: 75
GGDLEITTHS FNCRGEFFYC                                                20

SEQ ID NO: 76           moltype = AA  length = 11
FEATURE                 Location/Qualifiers
REGION                  1..11
                        note = synthetic peptide construct
source                  1..11
                        mol_type = protein
                        organism = synthetic construct
SEQUENCE: 76
CRIKQIINMW Q                                                         11

SEQ ID NO: 77           moltype = AA  length = 11
FEATURE                 Location/Qualifiers
REGION                  1..11
                        note = synthetic peptide construct
source                  1..11
                        mol_type = protein
                        organism = synthetic construct
SEQUENCE: 77
CKIRQIVNRW Q                                                         11

SEQ ID NO: 78           moltype = AA  length = 18
FEATURE                 Location/Qualifiers
REGION                  1..18
                        note = synthetic peptide construct
source                  1..18
                        mol_type = protein
                        organism = synthetic construct
SEQUENCE: 78
GGDMRDNWRS ELYKYKVV                                                  18

SEQ ID NO: 79           moltype = AA  length = 18
FEATURE                 Location/Qualifiers
REGION                  1..18
                        note = synthetic peptide construct
source                  1..18
                        mol_type = protein
                        organism = synthetic construct
SEQUENCE: 79
GGNMKDNWRS ELYKYKVV                                                  18

SEQ ID NO: 80           moltype = AA  length = 46
FEATURE                 Location/Qualifiers
```

```
REGION                 1..46
                       note = synthetic peptide construct
source                 1..46
                       mol_type = protein
                       organism = synthetic construct
SEQUENCE: 80
LTVQARLLLS GIVQQQNNLL RAIEAQQHLL QLTVWGIKQL QARVLA                 46

SEQ ID NO: 81          moltype = AA  length = 46
FEATURE                Location/Qualifiers
REGION                 1..46
                       note = synthetic peptide construct
source                 1..46
                       mol_type = protein
                       organism = synthetic construct
SEQUENCE: 81
LTVQARQLLS GIVQQQSNLL KAIEAQQHML QLTVWGIKQL QTRVLA                 46

SEQ ID NO: 82          moltype = AA  length = 16
FEATURE                Location/Qualifiers
REGION                 1..16
                       note = synthetic peptide construct
source                 1..16
                       mol_type = protein
                       organism = synthetic construct
SEQUENCE: 82
DQQLLGIWGC SGKLIC                                                  16

SEQ ID NO: 83          moltype = AA  length = 16
FEATURE                Location/Qualifiers
REGION                 1..16
                       note = synthetic peptide construct
source                 1..16
                       mol_type = protein
                       organism = synthetic construct
SEQUENCE: 83
DQQLLGLWGC SGKLIC                                                  16

SEQ ID NO: 84          moltype = AA  length = 20
FEATURE                Location/Qualifiers
REGION                 1..20
                       note = synthetic peptide construct
source                 1..20
                       mol_type = protein
                       organism = synthetic construct
SEQUENCE: 84
WLWYIKIFIM IVGGLVGLRI                                              20

SEQ ID NO: 85          moltype = AA  length = 20
FEATURE                Location/Qualifiers
REGION                 1..20
                       note = synthetic peptide construct
source                 1..20
                       mol_type = protein
                       organism = synthetic construct
SEQUENCE: 85
WLWYIRIFIM IVGGLIGLRI                                              20

SEQ ID NO: 86          moltype = AA  length = 4
FEATURE                Location/Qualifiers
REGION                 1..4
                       note = synthetic peptide construct
source                 1..4
                       mol_type = protein
                       organism = synthetic construct
SEQUENCE: 86
AAAE                                                               4

SEQ ID NO: 87          moltype = AA  length = 4
FEATURE                Location/Qualifiers
REGION                 1..4
                       note = synthetic peptide construct
source                 1..4
                       mol_type = protein
                       organism = synthetic construct
SEQUENCE: 87
AAAA                                                               4

SEQ ID NO: 88          moltype = AA  length = 5
```

-continued

```
FEATURE                Location/Qualifiers
REGION                 1..5
                       note = synthetic peptide construct
source                 1..5
                       mol_type = protein
                       organism = synthetic construct
SEQUENCE: 88
AAAAL                                                                   5

SEQ ID NO: 89          moltype = DNA  length = 1209
FEATURE                Location/Qualifiers
misc_feature           1..1209
                       note = synthetic nucleotide sequence Env-CE1_V1V2 BaL
source                 1..1209
                       mol_type = other DNA
                       organism = synthetic construct
SEQUENCE: 89
atgcgggtga cggagatccg gaagtcgtat cagcactggt ggcggtgggg catcatgctc  60
cttgggatac tgatgatctg caacgccgag gagaagctgt gggtcacggt gtactacggg  120
gtcccggtct ggaaggaggc caccacgacc ctgttctgcg cgagcgaccg caaggcctac  180
gacaccgagg tgcacaacgt gtgggctacg cacgcgtgcg tgccaacgga ccctaacccg  240
caggaggtgg aactgaagaa cgtgaccgag aacttcaaca tgtggaagaa caacatggtg  300
gagcagatgc acgaggacat catctccctg tgggaccagt cgctgaagcc gtgcgtcaag  360
ctgacgccgc tctgcgtcac gctgaactgc accgacctgc gcaacgccac gaacggcaac  420
gacaccaaca ccactagtag ctcgcgcggc atggtgggcg gcggcgagat gaagaactgc  480
agcttcaaca tcacgaccaa catccgcggc aaggtgcaga aggagtacgc cctgttctac  540
aagctggaca tcgcccctat cgacaacaac agcaacaacc gctaccggct gatcagctgc  600
ggcgctaagt tcgagccgat ccctatccac tactgcacgc cagctggatt cgcgggagcg  660
aaggtgcagt gcacgcacgg catccgacct gtggtctcga cgcagctgct cctgaacgga  720
agcctggcag aggcagctga cagcggcggg gacccggaga tcgtcatgca ctccttcaac  780
tgcgggggcg agttcttcta ctgcggagcc aaggacaact ggcggtctga gctgtacaag  840
tacaaggtcg tggctgcgaa ggcgcgacgg agggtggtcc agcgcgagaa gcgagccggt  900
gcagtgggct tccttgggac ggccggctcg acgatgggag cggcatcggt cgcggtgctg  960
acggtccagg cgaggctgct gctcagcggg atcgtccagc agcagaacaa cctgctccgg  1020
gcgatcgagg cgcagcagca cctgctccag ttaacggtct ggggcatcaa gcagctgcag  1080
gctcgagccg cggactggct ctggtacatc aagatcttca tcatgatcgt gggcggactg  1140
gtcggcctgc gaatcgctgc attccgcgtc cggaaggggt actcgcctct cagcctccaa  1200
acgtgataa                                                        1209
```

METHODS AND COMPOSITIONS FOR INDUCING AN IMMUNE RESPONSE USING CONSERVED ELEMENT CONSTRUCTS

CROSS-REFERENCE TO RELATING APPLICATIONS

This application is a continuation of U.S. application Ser. No. 15/573,701, filed on Nov. 13, 2017, which is a U.S. National Stage Application of International Application No.: PCT/US2016/032317, filed on May 13, 2016, which claims priority to and benefit of U.S. Provisional Application No. 62/161,123, filed May 13, 2015 and U.S. Provisional Application No. 62/241,599, filed on Oct. 14, 2015, the disclosures of each of which are explicitly incorporated by reference herein in their entirety.

REFERENCE TO AN ELECTRONIC SEQUENCE LISTING

The instant application contains a Sequence Listing that has been submitted electronically and which is hereby incorporated by reference in its entirety. The Sequence Listing was created on Feb. 17, 2023, is named "22-0965-WO-US-CON.xml" and is 118,168 bytes in size.

BACKGROUND OF THE INVENTION

Sequence diversity and immunodominance are major obstacles in the design of an effective vaccine against HIV. A vaccine that can induce cross-clade specific immune responses is sought. One approach to achieving robust cross-clade immune responses is the use of conserved element (CE) vaccines (see, e.g., WO 2012/062873 and WO 2013/131099) that can serve as a "universal" vaccine in that it is able to induce immune responses to most or all circulating strains of a virus. It was additionally determined that improved immune responses to highly conserved regions were obtained using a prime-boost vaccine regimen that included CE prime followed by boost with a vector expressing the full-length immunogen. This method led to the induction of immune responses with altered breadth and greatly improved cytotoxic responses (see, e.g., Kulkarni, et al., PLoS One; 9:e86254, 2014; Kulkarni, et al., PLos One 9:e111085, 2014; U.S. Patent Application Publication No. 20150056237, WO 2012/062873 and WO 2013/131099). The present invention addresses the need for an improved protocol for inducing an immune response using a conserved element vaccine and substantially full-length antigen. Further, the invention provides surprisingly effective HIV Env conserved element immunological composition that generates a robust immune response to the conserved regions of HIV Env proteins.

BRIEF SUMMARY OF SOME EMBODIMENTS OF THE DISCLOSURE

In one aspect, the present disclosure provides an improvement to methods for inducing an immune response using a nucleic acid CE immunogenic composition, which comprises one or more nucleic acids encoding one or more CE polypeptides, where the method comprises administering one or more CE nucleic acid constructs to a patient as a prime follow by co-administration of the CE nucleic acid immunogen(s) with an immunogenic composition comprising a nucleic acid construct encoding a substantially full-length form of the antigen from which the CEs are derived. Boosting by co-administering the CE immunogenic composition(s) and full-length, or substantially full-length, antigen improves immune responses, e.g., by further enhancing the levels of cytotoxic T cells, focusing the immune response to the highly conserved epitopes, compared to boosting with only full-length antigen.

Thus, the disclosure provides an improved prime-boost immunization regimen employing CE immunogens in combination with full-length immunogens that result in superior breadth, magnitude and quality of immune responses. This is accomplished with a priming administration of a CE immunogenic compositions(s) focusing the immune responses to highly conserved epitopes of the virus or immunogen of interest. The boosting step is accomplished by co-administration of a vaccine expressing CEs together with full-length molecule. Although this method may find use for inducing immune responses to an HIV antigen, such as Gag or Env, the method is not limited to HIV but can be employed to improve the induction of immune responses to any subdominant epitopes (cellular and or humoral) to increase breadth, magnitude and quality of the immune responses.

In a further aspect, the present disclosure provides immunogenic conserved element (CE) vaccine compositions and methods of using such compositions to induce an immune response to HIV envelope polypeptides. An immunogenic composition of the invention can induce immune responses to most or all circulating strains of HIV. This disclosure includes a description of 12 regions of the HIV envelope, which are highly conserved throughout the known universe of HIV M Group sequences. The invention provides CE polypeptides that comprise multiple CEs from the conserved regions of HIV. In typical embodiments, two CE polypeptides that differ from one another by only a few amino acids are administered in order to elicit an immune response across most strains of HIV.

In some embodiments, an immunogenic composition of the invention comprises multiple CE sequences, each having an amino acid sequence of SEQ ID NOS:1-23. In illustrative embodiments, the conserved element regions employed in the immunogens are 11, 14, 21, 15, 23, 21, 13, 12, 14, 43, 20, and 13 amino acids in length. In typical embodiments, each CE segment of the immunogen is separated by linkers that facilitate processing of the protein.

In some embodiments, an immunogenic composition of the invention comprises multiple CE sequences that include CE from each of the conserved regions of HIV Env, where each CE has a sequence shown in FIG. 24.

In some embodiments, the invention provides immunogenic compositions comprising multiple HIV Gag CE elements (e.g., FIG. 23 or Gag CE elements listed under Table 2) and methods of using such immunogenic compositions to induce an immune response to Gag. The HIV Gag CE element immunogenic compositions may be administered with HIV Env immunogenic compositions as described herein. In such embodiments, the CE constructs (HIV Gag and Env CE constructs) may be administered concurrently or sequentially.

In some embodiments, an immunogenic polypeptide comprising Env conserved elements in accordance with the invention further comprises variable region sequences, e.g., a V1V2 variable region sequence.

The conserved element immunogens are typically administered as nucleic acid vaccines in which DNA comprising one ore more polynucleotide sequences encoding one or more polypeptides comprising the CEs is administered to a subject.

In some embodiments, DNA vectors are engineered to express the CE immunogens (conserved element polypeptides comprising multiple conserved elements, such as Env-CE1 and Env-CE2 as shown in FIG. 10 and as further described herein) only, to express secreted Env-CE proteins having the N-terminal Env signal peptide or an N-terminal GM-CSF signal peptide, to express the CE polypeptide(s) as a core fusion to the monocyte chemoattractant protein 3 (MCP3) chemokine to stabilize the protein expression and enhance secretion of the proteins, to express the CE polypeptide(s) as a fusion to lysosomal associated membrane protein 1 (LAMP-1) to direct the proteins to the lysosomal compartment including access to the MHC class II pathway, or to target the protein to the degradation pathway using a sequence such as a β-catenin degradation signal.

Illustrative embodiments of the disclosure, include, but are not limited to, the following:

Embodiment 1: A method of inducing an immune response to a protein of interest, the method comprising: priming an immune response to the protein of interest, wherein priming comprises administering at least one nucleic acid construct encoding a conserved element polypeptide, wherein the conserved elements are from the protein of interest and the polypeptide comprises at least three conserved elements, each from 8 to 50 amino acids in length where the conserved elements are joined by non-naturally occurring linkers, with the proviso that a nucleic acid construct encoding the full-length protein, or a substantially full-length region thereof, is not administered in the priming step; boosting the immune response to the protein of interest, wherein bosting comprises co-administering (i) a nucleic acid construct encoding the full-length protein, or substantially full-length protein and (ii) the nucleic acid construct encoding the conserved element polypeptide.

Embodiment 2: The method of Embodiment 1, wherein the boosting step comprises administering the nucleic acid of (i) and the nucleic acid of (ii) at the same time.

Embodiment 3: The method of Embodiment 1 or 2, wherein the nucleic acid constructs are administered intramuscularly by in vivo electroporation.

Embodiment 4: The method of any one of Embodiments 1 to 3, wherein the priming and boosting steps further comprise administering a second conserved element nucleic acid construct that encodes a second conserved element polypeptide that comprises at least one variant of a conserved element contained in the first conserved element polypeptide, wherein the variant in the second polypeptide differs from the variant in the first polypeptide by 1, 2, 3, 4, or 5 amino acids.

Embodiment 5: The method of Embodiment 4, the first and second conserved element nucleic acid constructs are administered sequentially.

Embodiment 6: The method of Embodiment 4, the first and second conserved element nucleic acid constructs are administered concurrently.

Embodiment 7: The method of any one of Embodiments 1 to 6, wherein the protein of interest is HIV-1 Gag and the conserved elements are from HIV-1 p24gag.

Embodiment 8: The method of Embodiment 7, wherein one conserved element polypeptide comprises at least 7 conserved elements from different regions of p24gag; and each of the conserved elements has a conserved element sequence shown in Table 2.

Embodiment 9: The method of Embodiment 8, wherein one conserved element polypeptide comprises conserved elements that each have a sequence set forth in SEQ ID NOS:26, 27, 28, 29, 30, 31, and 32; and a second conserved element polypeptide comprises conserved elements that each have a sequence set forth in SEQ ID NOS: 33, 34, 35, 36, 37, 38, and 39.

Embodiment 10: The method of Embodiment 9, wherein one Gag conserved element polypeptide comprises the amino acid sequence of SEQ ID NO:40 and the second Gag conserved element polypeptide comprises the amino acid sequence of SEQ ID NO:41.

Embodiment 11: The method of Embodiment 9 or 10, wherein the conserved element polypeptides encoded by the first and second nucleic acid Gag conserved element nucleic acid constructs are each fused to a GM-CSF signal peptide.

Embodiment 12: The method of any one of Embodiments 1 to 6, wherein the protein of interest is an HIV-1 Env sequence.

Embodiment 13: The method of Embodiment 12, wherein one conserved element polypeptide comprises at least 12 conserved elements from different conserved regions of Env of HIV-1 Group M and each of the conserved elements has a conserved element sequence shown in Table 1.

Embodiment 14: The method of Embodiment 13, wherein one conserved element polypeptide comprises conserved elements that each have a sequence set forth in SEQ ID NOS:1, 2, 4, 6, 8, 10, 12, 14, 16, 18, 20, and 22; and a second conserved element polypeptide comprises conserved elements that each have a sequence set forth in SEQ ID NOS:1, 3, 5, 7, 9, 11, 13, 15, 17, 19, 21, and 23.

Embodiment 15: The method of Embodiment 14, wherein one Env conserved element polypeptide comprises the amino acid sequence of SEQ ID NO:24 and the second Env conserved element polypeptide comprises the amino acid sequence of SEQ ID NO:25.

Embodiment 16: The method of Embodiment 14 or 15, wherein the conserved element polypeptides encoded by the first and second nucleic acid Env conserved element nucleic acid constructs are each fused to a GM-CSF signal peptide.

Embodiment 17: The method of any one of Embodiments 4 to 16, wherein the first and second nucleic acid conserved element nucleic acid constructs are contained in the same vector.

Embodiment 18: The method of any one of Embodiments 4 to 16, wherein the first and second nucleic acid constructs are contained in different vectors.

Embodiment 19: The method of any one of Embodiments 1 to 18, wherein boosting is performed at least two weeks after the priming step.

Embodiment 20: The method of any one of Embodiments 1 to 19, wherein the priming step comprises two administrations of the one or more conserved element polypeptides, each separated by at least 2 weeks; and the boosting step comprises two co-administrations, each separated by at least 2 weeks.

Embodiment 21: A method of inducing an immune response to HIV Gag in a patient, the method comprising: priming an immune response to HIV Gag, wherein priming comprises administering to the patient a CE-encoding expression vector that comprises a nucleic acid sequence encoding SEQ ID NO:40 fused at the N-terminus to a human GM-CSF signal peptide and a nucleic acid sequence encoding SEQ ID NO:41 fused at the N-terminus to a human GM-CSF signal peptide;

and boosting an immune response to HIV Gag, wherein boosting comprises co-delivering the CE-encoding expression vector with an expression vector that encodes full-length HIV-1 p55Gag, or substantially full-length Gag.

Embodiment 22: The method of Embodiment 21, wherein the boosting step is performed about two months after the priming step.

Embodiment 23: The method of Embodiment 21 or 22, wherein the method comprises two priming steps, each separated by about two months; and two boosting steps, each separated by about two months. In some embodiments, the priming steps are separated by at least one month and/or the boosting steps are separated by at least one month. In some embodiments, the priming steps are separated by about three months and/or the boosting steps are separated by about three month.

Embodiment 24: A method of inducing an immune response to a protein of interest, wherein the protein of interest is HIV Gag or HIV Env, the method comprising: priming an immune response to the protein of interest, wherein priming comprises administering at least one nucleic acid construct encoding a conserved element polypeptide, wherein the conserved elements are from the protein of interest and the polypeptide comprises at least three conserved elements, each from 8 to 50 amino acids in length where the conserved elements are joined by non-naturally occurring linkers, with the proviso that a nucleic acid construct encoding the full-length protein, or a substantially full-length region thereof, is not administered in the priming step; boosting the immune response to the protein of interest, wherein bosting comprises co-administering (i) a nucleic acid construct encoding the full-length protein, or substantially full-length protein and (ii) the nucleic acid construct encoding the conserved element polypeptide.

Embodiment 25: The method of Embodiment 24, wherein the boosting step comprises administering the nucleic acid of (i) and the nucleic acid of (ii) at the same time.

Embodiment 26: The method of Embodiment 24 or 25, wherein the nucleic acid constructs are administered intramuscularly by in vivo electroporation.

Embodiment 27: The method of any one of Embodiments 24 to 26, wherein the priming and boosting steps further comprise administering a second conserved element nucleic acid construct that encodes a second conserved element polypeptide that comprises at least one variant of a conserved element contained in the first conserved element polypeptide, wherein the variant in the second polypeptide differs from the variant in the first polypeptide by 1, 2, 3, 4, or 5 amino acids.

Embodiment 28: The method of Embodiment 27, the first and second conserved element nucleic acid constructs are administered sequentially.

Embodiment 29: The method of Embodiment 27, the first and second conserved element nucleic acid constructs are administered concurrently.

Embodiment 30: The method of any one of Embodiments 24 to 29, wherein the first and second nucleic acid conserved element nucleic acid constructs are contained in the same vector.

Embodiment 31: The method of any one of Embodiments 24 to 29, wherein the first and second nucleic acid constructs are contained in different vectors.

Embodiment 32: The method of any one of Embodiments 24 to 31, wherein boosting is performed at least two weeks after the priming step.

Embodiment 33: The method of any one of Embodiments 24 to 32, wherein the priming step comprises two administrations of the one or more conserved element polypeptides, each separated by at least 2 weeks; and the boosting step comprises two co-administrations, each separated by at least 2 weeks.

Embodiment 34: A method of inducing an immune response to HIV Gag in a patient, the method comprising: priming an immune response to HIV Gag, wherein priming comprises administering to the patient a CE-encoding expression vector that comprises a nucleic acid sequence encoding p24GagCE1 as set forth in Table 2 fused at the N-terminus to a human GM-CSF signal peptide and a nucleic acid sequence encoding p24GagCE2 as set forth in Table 2 fused at the N-terminus to a human GM-CSF signal peptide; and boosting an immune response to HIV Gag, wherein boosting comprises co-delivering the CE-encoding expression vector with an expression vector that encodes full-length HIV-1 p55gag, or substantially full-length HIV-1 p55gag.

Embodiment 35: The method of Embodiment 34 wherein the boosting step is performed about two months after the priming step.

Embodiment 36: The method of Embodiment 34 or 35, wherein the method comprising two priming steps, each separated by about two months; and two boostep steps, each separated by about two months. In some embodiments, the priming steps are separated by at least one month and/or the boosting steps are separated by at least one month. In some embodiments, the priming steps are separated by about three months and/or the boosting steps are separated by about three month.

Embodiment 37: A nucleic acid encoding an immunogenic HIV Env conserved element polypeptide, wherein the HIV Env conserved element polypeptide comprises at least five conserved elements selected from SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22; and the conserved elements are separated by linkers of 1 to 5 amino acids in length.

Embodiment 38: The nucleic acid of Embodiment 37, wherein the HIV Env conserved element polypeptide comprises at least six, seven, eight, nine, ten, or eleven conserved elements selected from SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22

Embodiment 39: The nucleic acid of Embodiment 37, wherein the HIV Env conserved element polypeptide comprises the conserved elements of SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22.

Embodiment 40: The nucleic acid of Embodiment 37, 38, or 39, wherein the HIV Env conserved element polypeptide further comprises a V1V2 variable region sequence.

Embodiment 41: The nucleic acid of Embodiment 37, wherein the HIV Env conserved element polypeptide comprises SEQ ID NO:24.

Embodiment 42: A nucleic acid encoding an immunogenic HIV Env conserved element polypeptide, wherein the HIV Env conserved element polypeptide comprises at least five conserved elements selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23; and the conserved elements are separated by linkers of 1 to 5 amino acids in length.

Embodiment 43: The nucleic acid of Embodiment 42, wherein the HIv Env conserved element polypeptide comprises at least six, seven, eight, nine, ten, or eleven conserved elements selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 44: The nucleic acid of Embodiment 42, wherein the HIV Env conserved element polypeptide comprises the conserved elements of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 45: The nucleic acid of Embodiment 42, 43, or 44, further comprising a V1V2 variable region sequence.

Embodiment 44: The nucleic acid of Embodiment 42, wherein the HIV Env conserved element polypeptide comprises SEQ ID NO:25.

Embodiment 45: The nucleic acid of any one of Embodiments 42 to 44, wherein the HIV Env conserved element polypeptide comprises a signal peptide.

Embodiment 46: The nucleic acid of Embodiment 45, wherein the signal peptide is the signal peptide of GM-CSF.

Embodiment 47: An immunogenic HIV Env conserved element polypeptide comprising at least five conserved elements selected from SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22, wherein the conserved elements are separated by linkers of 1 to 5 amino acids in length.

Embodiment 48: The immunogenic HIV Env conserved element polypeptide of Embodiment 47, wherein the polypeptide comprises at least six, seven, eight, nine, ten, or eleven conserved elements selected from SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22

Embodiment 49: The immunogenic HIV Env conserved element polypeptide of Embodiment 47, wherein the polypeptide comprises the conserved elements of SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22.

Embodiment 50: The immunogenic HIV Env conserved element polypeptide of Embodiment 47, 48, or 49, wherein the polypeptide further comprises a V1V2 variable region sequence.

Embodiment 51: The immunogenic HIV Env conserved element polypeptide of Embodiment 47, wherein the polypeptide comprises SEQ ID NO:24.

Embodiment 52: An immunogenic HIV Env conserved element polypeptide comprising at least five conserved elements selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23; wherein the conserved elements are separated by linkers of 1 to 5 amino acids in length.

Embodiment 53: The immunogenic HIV Env conserved element polypeptide of Embodiment 52, wherein the polypeptide comprises at least six, seven, eight, nine, ten, or eleven conserved elements selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 54: The immunogenic HIV Env conserved element polypeptide of Embodiment 52, wherein the polypeptide comprises the conserved elements of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 55: The immunogenic HIV Env conserved element polypeptide of Embodiment 52, 53, or 54, wherein the polypeptide further comprises a V1V2 variable region sequence.

Embodiment 56: The immunogenic HIV Env conserved element polypeptide of Embodiment 52, wherein the polypeptide comprises SEQ ID NO:25.

Embodiment 57: A composition comprising: a first nucleic acid encoding a first immunogenic HIV Env conserved element polypeptide that comprises at least five conserved elements selected from SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22, wherein the conserved elements are separated by linkers of 1 to 5 amino acids in length; and a second nucleic acid encoding a second immunogenic HIV Env conserved element polypeptide comprises at least five conserved elements selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23, wherein the conserved elements are separated by linkers of 1 to 5 amino acids in length.

Embodiment 58: The composition of Embodiment 57, wherein the first immunogenic HIV Env conserved element polypeptide comprises at least six, seven, eight, nine, ten, or eleven conserved elements selected from SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22; and the second immunogenic HIV Env conserved element polypeptide comprises at least six, seven, eight, nine, ten, or eleven conserved elements selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 59: The composition of Embodiment 57, wherein the first immunogenic HIV Env conserved element polypeptide comprises the conserved elements of SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22.

Embodiment 60: The composition of Embodiment 57, wherein the second immunogenic HIV Env conserved element polypeptide comprises the conserved elements of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 61: The composition of Embodiment 57, wherein the first immunogenic HIV Env conserved element polypeptide comprises the conserved elements of SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22; and the second immunogenic HIV Env conserved element polypeptide comprises the conserved elements of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 62: The compositions of any one of Embodiments 57 to 61, wherein the first immunogenic HIV Env conserved element polypeptide or the second immunogenic HIV Env conserved element polypeptide; or both the first immunogenic HIV Env conserved element polypeptide and the second immunogenic HIV Env conserved element polypeptide further comprise a V1V2 variable region sequence.

Embodiment 63: The composition of Embodiment 57, wherein the first immunogenic HIV Env conserved element comprises the amino acid sequence of SEQ ID NO:24 and the second immunogenic HIV Env conserved element polypeptide comprises the amino acid sequence of SEQ ID NO:25.

Embodiment 64: The composition of any one of Embodiments 57 to 63, wherein the first nucleic acid and second nucleic acid are contained in separate expression vectors.

Embodiment 65: The composition of any one of Embodiments 57 to 63, wherein the first nucleic acid and second nucleic acid are contained in the same expression vector.

Embodiment 66: A composition comprising: a first immunogenic HIV Env conserved element polypeptide comprising at least five conserved elements selected from SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22, wherein the conserved elements are separated by linkers of 1 to 5 amino acids in length; and a second immunogenic HIV Env conserved element polypeptide comprises at least five conserved elements selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23, wherein the conserved elements are separated by linkers of 1 to 5 amino acids in length.

Embodiment 67: The composition of Embodiment 66, wherein the first immunogenic HIV Env conserved element polypeptide comprises at least six, seven, eight, nine, ten, or eleven conserved elements selected from SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22; and the second immunogenic HIV Env conserved element polypeptide comprises at least six, seven, eight, nine, ten, or eleven conserved elements selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 68: The composition of Embodiment 67, wherein the first immunogenic HIV Env conserved element polypeptide comprises the conserved elements of SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22.

Embodiment 69: The composition of Embodiment 67, wherein the second immunogenic HIV Env conserved element polypeptide comprises the conserved elements of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 70: The composition of Embodiment 67, wherein the first immunogenic HIV Env conserved element polypeptide comprises the conserved elements of SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22; and the second immunogenic HIV Env conserved element polypeptide comprises the conserved elements of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 71: The composition of any one of Embodiments 67 to 70, wherein the first immunogenic HIV Env conserved element polypeptide or the second immunogenic HIV Env conserved element polypeptide; or both the first immunogenic HIV Env conserved element polypeptide and the second immunogenic HIV Env conserved element polypeptide further comprise a V1V2 variable region sequence.

Embodiment 72: The composition of Embodiment 67, wherein the first immunogenic HIV Env conserved element comprises the amino acid sequence of SEQ ID NO:24 and the second immunogenic HIV Env conserved element polypeptide comprises the amino acid sequence of SEQ ID NO:25.

Embodiment 73: A method of inducing an immune response to HIV Env, the method comprising administering a nucleic acid of any one of Embodiments 37 to 46 to a subject or an HIV Env conserved element polypeptide of any one of Embodiment 47 to 56 to the subject; or administering a compositions of any one of Embodiments 57 to 72.

Embodiment 74: A method of inducing an immune response to HIV Env, the method comprising administering: a first nucleic acid encoding a first immunogenic HIV Env conserved element polypeptide that comprises at least five conserved elements selected from SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22, wherein the conserved elements are separated by linkers of 1 to 5 amino acids in length; and a second nucleic acid encoding a second immunogenic HIV Env conserved element polypeptide comprises at least five conserved elements selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23, wherein the conserved elements are separated by linkers of 1 to 5 amino acids in length.

Embodiment 75: The method of Embodiment 74, wherein: the first immunogenic HIV Env conserved element polypeptide comprises at least six, seven, eight, nine, ten, or eleven conserved elements selected from SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22; and the second immunogenic HIV Env conserved element polypeptide comprises at least six, seven, eight, nine, ten, or eleven conserved elements selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 76: The method of Embodiment 74, wherein the first immunogenic HIV Env conserved element polypeptide comprises the conserved elements of SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22.

Embodiment 77 The method of Embodiment 74, wherein the second immunogenic HIV Env conserved element polypeptide comprises the conserved elements of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 78: The method of Embodiment 74, wherein: the first immunogenic HIV Env conserved element polypeptide comprises the conserved elements of SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22; and the second immunogenic HIV Env conserved element polypeptide comprises the conserved elements of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 79. The method of any one of Embodiments 74 to 78, wherein the first immunogenic HIV Env conserved element polypeptide or the second immunogenic HIV Env conserved element polypeptide; or both the first immunogenic HIV Env conserved element polypeptide and the second immunogenic HIV Env conserved element polypeptide further comprise a V1V2 variable region sequence.

Embodiment 80: The method of Embodiment 74, wherein the first immunogenic HIV Env conserved element comprises the amino acid sequence of SEQ ID NO:24 and the second immunogenic HIV Env conserved element polypeptide comprises the amino acid sequence of SEQ ID NO:25.

Embodiment 81: The method of any one of Embodiments 74 to 80, wherein the first nucleic acid and second nucleic acid are contained in separate expression vectors.

Embodiment 82: The method of any one of Embodiments 74 to 80, wherein the first nucleic acid and second nucleic acid are contained in the same expression vector.

Embodiment 83: The method of any one of Embodiments 74 to 80, wherein the first and the second nucleic acids are administered sequentially.

Embodiment 84: The method of any one of Embodiments 74 to 80, wherein the first and second nucleic acids are administered concurrently.

Embodiment 85: The method of any one of Embodiments 74 to 84, wherein a nucleic acid encoding a full-length Env polypeptide, or substantially full-length Env polypeptide, is administered after the first and the second nucleic acid encoding the first and the second HIV conserved element polypeptides; or a full-length Env polypeptide, or substantially full-length Env polypeptide, is administered after the first and the second nucleic acid encoding the first and the second HIV conserved element polypeptides.

Embodiment 86: The method of any one of Embodiments 74 to 85, wherein the nucleic acid constructs are administered intramuscularly by in vivo electroporation.

Embodiment 87: A method of inducing an immune response to HIV Env, the method comprising administering: a first immunogenic HIV Env conserved element polypeptide that comprises at least five conserved elements selected from SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22, wherein the conserved elements are separated by linkers of 1 to 5 amino acids in length; and a second immunogenic HIV Env conserved element polypeptide comprises at least five conserved elements selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23, wherein the conserved elements are separated by linkers of 1 to 5 amino acids in length.

Embodiment 88: The method of Embodiment 87, wherein the first immunogenic HIV Env conserved element polypeptide comprises at least six, seven, eight, nine, ten, or eleven conserved elements selected from SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22; and the second immunogenic HIV Env conserved element polypeptide comprises at least six, seven, eight, nine, ten, or eleven conserved elements selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 89: The method of Embodiment 87, wherein the first immunogenic HIV Env conserved element polypeptide comprises the conserved elements of SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22.

Embodiment 90: The method of Embodiment 87, wherein the second immunogenic HIV Env conserved element polypeptide comprises the conserved elements of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 91: The method of Embodiment 87, wherein the first immunogenic HIV Env conserved element polypeptide comprises the conserved elements of SEQ ID NO:1, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22; and the second immunogenic HIV Env conserved element polypeptide comprises the conserved elements of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23.

Embodiment 92: The method of any one of Embodiments 87 to 91, wherein the first immunogenic HIV Env conserved element polypeptide or the second immunogenic HIV Env conserved element polypeptide; or both the first immunogenic HIV Env conserved element polypeptide and the second immunogenic HIV Env conserved element polypeptide further comprise a V1V2 variable region sequence.

Embodiment 93: The method of Embodiment 87, wherein the first immunogenic HIV Env conserved element comprises the amino acid sequence of SEQ ID NO:24 and the second immunogenic HIV Env conserved element polypeptide comprises the amino acid sequence of SEQ ID NO:25.

Embodiment 94: The method of Embodiments 87 to 93, wherein the first and the second immunogenic HIV Env conserved element polypeptides are administered sequentially.

Embodiment 95: The method of Embodiments 87 to 93, wherein the first and the second immunogenic HIV Env conserved element polypeptides are administered concurrently.

Embodiment 96: The method of any one of Embodiments 87 to 95, wherein a full-length Env polypeptide, or substantially full-length Env polypeptide, is administered after the first and the second HIV conserved element polypeptides; or a full-length Env polypeptide, or substantially full-length Env polypeptide, is administered after the first and the second nucleic acid encoding the first and the second HIV conserved element polypeptides.

Embodiment 97: An HIV Gag CE polypeptide comprising: (a) SEQ ID NO:27, SEQ ID NO:29, SEQ ID NO:31, SEQ ID NO:33, SEQ ID NO:35, and/or SEQ ID NO:37; or (b) SEQ ID NO:28, SEQ ID NO:30, SEQ ID NO:32, SEQ ID NO:34, SEQ ID NO:36, and/or SEQ ID NO:38.

Embodiment 98: An HIV Gag CE polypeptide comprising: P24CE8-1, p24CE9-1, p24CE3-1, p24CE10-1, p24CE5-1, p24CE11-1, p24CE6-1, p24CE12-1, p24CE13-1 as shown in FIG. 23; or P24CE8-1, p24CE9-2, p24CE3-2, p24CE10-21, p24CE5-2, p24CE11-2, p24CE6-2, p24CE12-2, p24CE13-2 as shown in FIG. 23.

Embodiment 99: The method of any one of Embodiments 87 to 96, further comprising administering an immunogenic composition to induce an immune response to HIV Gag, wherein the immunogenic composition is an HIV Gag CE polypeptide comprising p24 CE1, CE2, CE3, CE4, CE5, CE6, and CE7 as shown in FIG. 23; or an HIV Gag CE polypeptide of claim 41 or 42.

Embodiment 100: The method of any one of Embodiments 87 to 96, further comprising administering an immunogenic composition to induce an immune response to HIV Gag, wherein the method comprises administering an HIV Gag CE polypeptide comprising P24CE8-1, p24CE9-1, p24CE3-1, p24CE10-1, p24CE5-1, p24CE11-1, p24CE6-1, p24CE12-1, p24CE13-1 as shown in FIGS. 23 and P24CE8-1, p24CE9-2, p24CE3-2, p24CE10-21, p24CE5-2, p24CE11-2, p24CE6-2, p24CE12-2, p24CE13-2 as shown in FIG. 23.

Embodiment 101: A nucleic acid construct encoding an HIV Gag CE polypeptide of Embodiment 97 or 98.

Embodiment 102: The method of Embodiment 99 or 100, wherein the HIV Gag CE polypeptide is administered as a nucleic acid.

BRIEF DESCRIPTION OF THE DRAWINGS

FIG. 1: Derivation of SIV p27 CE and conservation relative to HIV-1 and SIV strains from multiple species. All sequences were compared to HIV-1 p24CE1, with a "." indicating homology. Toggle positions that distinguish SIV p27CE1 and p27CE2 are shown with red type. Amino acid differences that distinguished the SIV and HIV-1 CE but were conserved in other SIV strains are shown in light blue type. A protocol of including only one toggle site per CE was adhered to except for CE4, in which 2 additional amino acids were substituted since those amino acid variants were always found together in the database. No toggled amino acid was included for SIV p27 CE1, CE6 or CE7 due to the extreme conservation observed in those segments among available SIV sequences. The sequences were aligned to the consensus of those obtained from the Los Alamos HIV database. Blanks indicate that sequences corresponding to CE region were available. Two representative sequences are shown: SIVmac (species of origin: macaque), N=495; SIVsmm (sooty mangabey), N=272. Additional sequences were considered for the definition of CE including SIVver (vervet), N=3; SIVlst (l'Hoest), N=4; SIVmnd (mandrill), N=3; SIVgsn (greater spot-nosed), N=2; SIVdrl (drill), N=2; SIVden (Dent's Mona); N=1; SIVmus (mustached), N=1; SIVmon (mona) N=1; SIVdeb (De Brazza's), N=2; SIVsyk (Sykes), N=1; SIVtal (talapoin), N=2; SIVsun (sun-tailed), N=1.

FIG. 5: Increase of CE-primed T cell Responses by Co-delivery of CE&gag DNA as Booster Vaccination. The % of CE-specific IFN-γ+ T cells was measured by flow cytometry after the 1st and 2nd co-delivery booster vaccination. CE-specific responses were measured by intracellular cytokine staining after stimulation of PBMC with a CE-specific peptide pool covering all 7 CE (mixture of 15-mer overlapping by 11 AA and 10-mer overlapping by 9 AA). The statistical analysis using paired t test is shown.

FIG. 7: CE&gag DNA Co-delivery as Boost Increases the Levels of Cytotoxic CE-specific T cells. The T cells (CD4 and CD8 subsets) were analyzed for their granzyme B (GzmB) content and their ability to degranulate (CD107a) by flow cytometry. Statistical analysis of GzmB+ CD107a+ IFN-γ+ T cells of the 2 vaccine regimens are shown.

FIG. 11 provides an illustrative protocol for the vaccination of macaques with HIV Env-CE DNA. CE-specific immune responses in blood were evaluated at 2 weeks after V2 (second administration of vaccine) and V3 (third administration of vaccine) and after a rest period of 3 months.

FIG. 15 shows the results of mapping of CE-specific responses. This demonstrated recognition of six of the twelve CEs in four animals. PBMC were incubated with individual peptide pools spanning the 12 CE's and the % of CE-specific CD4 and CD8 cells producing IFN-γ was determined following peptide stimulation. Each animal recognized 2-4 CE. CE6, CE1, CE10, CE12, CE13, and CE15 did not show cellular responses in these animals in this experiment.

FIG. 19 shows a comparison of responses to individual CE before and after boosting with DNA plasmids expressing intact Env. The analysis shows that upon boost, 7 of the 12 segments (58%) of the HIV Env-CE are immunogenic.

FIG. 13 shows the results of a western immunoblot analysis of humoral immune responses. Proteins from cells transfected with HIV env-CE1 DNA or HIV env-CE2 DNA were separated on denaturing gels and transferred onto membranes. Individual strips of membranes were incubated with plasma (1:100 dilution) from the vaccinated macaques and visualized using standard western blot methodology. The results show that all four macaques immunized with HIV env-CE DNA developed antibody responses to the immunogens. Env-CE2 was better recognized, likely because higher levels of this protein were effectively loaded because the protein is slightly more stable than Env-CE1. The antibodies recognizing the CE immunogen are boosted in animals L985, R288 and to a lesser extent, in P574 and RO67.

FIG. 23 shows HIV Gag p24CE sequences. The term "initial" CE in FIG. 15 refers to HIV Gagp24 CE sequences described in U.S. Patent Application Publication No. 20150056237. "Alternate" CE sequences are described herein.

FIG. 24 shows additional HIV Env CE sequences.

DETAILED DESCRIPTION OF THE INVENTION

Terminology

Figure 2:
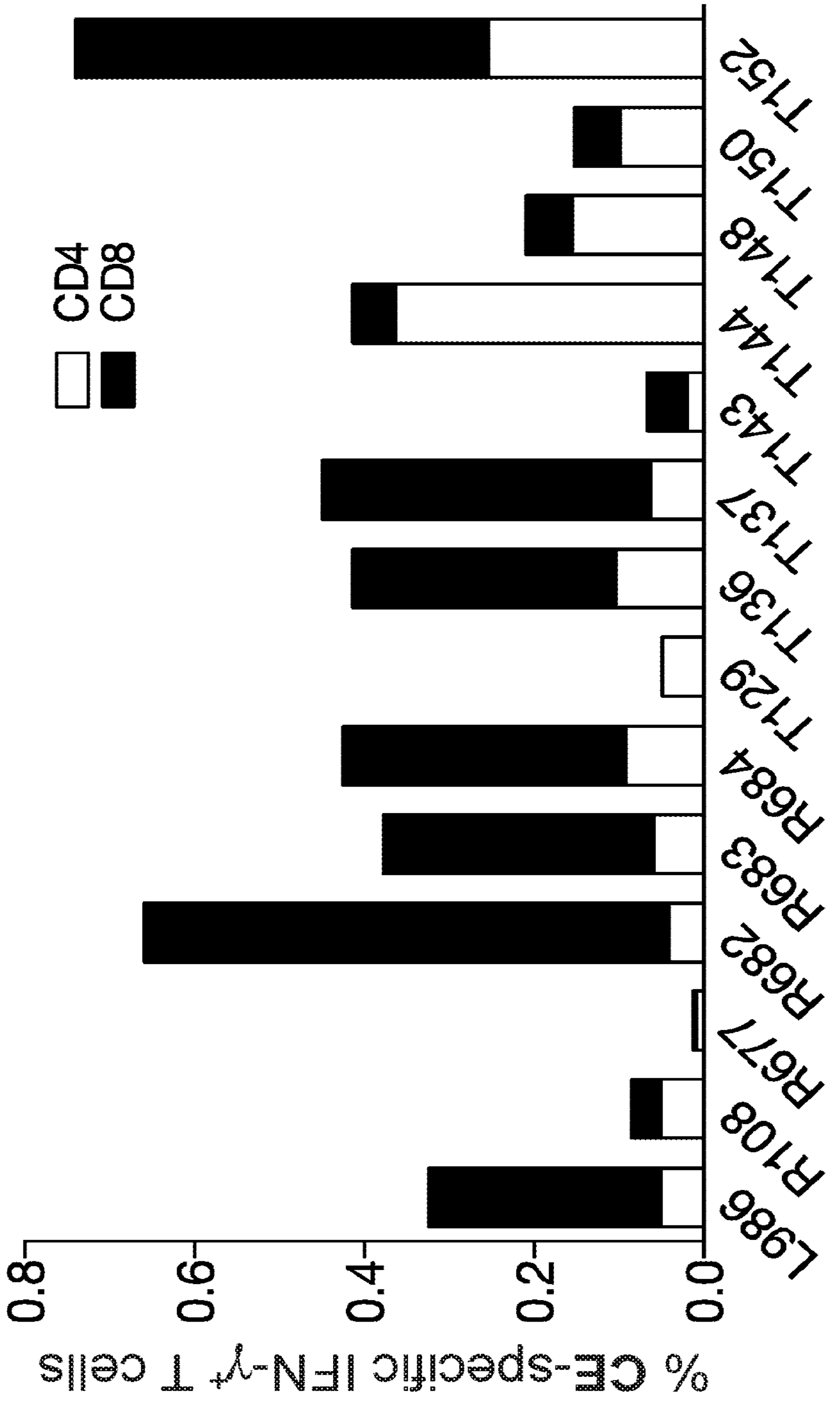
FIG. 2: CE-specific T cell responses in p27CE pDNA vaccinated macaques. Animals (N=14) were vaccinated with a mixture of p27CE1 and p27CE2 pDNA. The CE-specific T cell responses were measured by intracellular flow cytometry in blood at 2 weeks after the 2nd vaccination. PBMC were stimulated with a pool of peptides spanning the CE (15-mer overlapping by 11 AA and 10-mer overlapping by 9 AA). Macaques T129 through T152 were also vaccinated with HIV Env CE pDNA vaccine at the same time when the gag CE pDNA vaccine was administered. No difference in the induced cellular responses was found compared to animals (L986 through R684) which only received the gag CE pDNA vaccine, demonstrating lack of interference of gag and env CE induced immune responses.

A "conserved region" as used herein refers to a protein sequence that is conserved across a protein that has high sequence diversity in nature, e.g., a viral protein such as HIV Env or HIV Gag. A "conserved region" need not have 100% sequence identity across the diversity of naturally occurring sequence of the protein, but the amino acid sequence variability in the naturally occurring conserved region sequences is low, typically 10% or less. A "conserved element" in the context of the present invention is a segment of a conserved region that is at least 8 amino acids, or greater, in length. In some embodiments, a "conserved element" is greater than 8 amino acids in length, e.g., 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 or more amino acids in length. Typically, a conserved element is less than 50 amino acids in length. A "conserved element" need not be 100% conserved across the diversity of HIV sequences, e.g., HIV Gag sequences or HIV Env sequences. The sequence variability in the naturally occurring conserved element sequence is low, however, typically 10% or less.

In the context of this invention, a "conserved element pair" as it relates to a conserved element immunogenic composition, e.g., conserved elements of HIV Gag or HIV Env, refers to two versions of a conserved element sequence that have amino acid changes relative to one another such that the two sequence together cover at least 90% of naturally occurring sequences. For example, an HIV Env "conserved element pair" refers to two versions of a conserved element sequence that have amino acid changes relative to one another such that the two sequence together cover at least 90% of naturally occurring HIV Env variants belonging to the HIV-1 M group.

A "variable region" element in the context of HIV Env is a sequence from a variable region of HIV Env, e.g., the V1V2 region, that may also be included in an immunogenic HIV Env CE polypeptide of the invention if recognition of this region is associated with lower viral loads in published studies or if amino acid substitutions in that region are known to decrease viral replication fitness, or if recognition of the region has been associated with vaccine efficacy, or if amino acid substitutions in that region are associated with changes in predicted protein stability.

A "nucleic acid vaccine" as used herein includes both naked DNA vaccines, e.g., plasmid vaccine, and viral vector-based nucleic acid vaccines that are comprised by a viral vector and/or delivered as viral particles.

The term "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Unless otherwise indicated, a particular nucleic acid sequence also implicitly encompasses conservatively modified variants thereof (e.g., degenerate codon substitutions) and complementary sequences, as well as the sequence explicitly indicated. Degenerate codon substitutions can be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term "nucleic acid" is used interchangeably with gene, cDNA, oligonucleotide, and polynucleotide. A "nucleic acid" encompasses RNA as well as DNA.

The terms "identical" or percent "identity," in the context of two or more nucleic acids or polypeptide sequences, refer to two or more sequences or subsequences that are the same or have a specified percentage of amino acid residues or nucleotides that are the same (e.g., about 80%, 85%, 90%, 91%, 92%, 93%, 94%, 95%, 96%, 97%, 98%, 99%, or higher, identity over a specified region (e.g., a polypeptide sequence comprising collinear conserved elements), when compared and aligned for maximum correspondence over a comparison window or designated region) as measured using a BLAST or BLAST 2.0 sequence comparison algorithms with default parameters (see, e.g., NCBI web site or the like), or by manual alignment and visual inspection. In the present invention, in the context of comparison of a particular conserved element sequence with a variant of that sequence, identity is defined over the length of the conserved element reference sequence. In some embodiments, percent identity of one conserved element to a corresponding variant conserved element is determined by visual inspection.

The term "operably linked" refers to a functional linkage between a first nucleic acid sequence and a second nucleic acid sequence, such that the first and second nucleic acid sequences are transcribed into a single nucleic acid sequence. Operably linked nucleic acid sequences need not be physically adjacent to each other. The term "operably linked" also refers to a functional linkage between a nucleic acid expression control sequence (such as a promoter, or array of transcription factor binding sites) and a transcribable nucleic acid sequence, wherein the expression control sequence directs transcription of the nucleic acid corresponding to the transcribable sequence.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

The terms "mammal" or "mammalian" refer to any animal within the taxonomic classification mammalia. A "mammal" can refer to a human or a non-human primate. A "mammal" can also refer to a domestic animal, including for example, canine, feline, rodentia, including lagomorpha, murine, rattus, Cricetinae (hamsters), etc. A mammal can refer to an agricultural animal, including for example, bovine, ovine, porcine, equine, etc.

The terms "treating" and "treatment" refer to delaying the onset of, retarding or reversing the progress of, or alleviating or preventing either the disease or condition to which the term applies, or one or more symptoms of such disease or condition.

An "immunogen" refers to a molecule, typically a protein molecule in the current invention, containing one or more epitopes (either linear, conformational or both) that will stimulate a host's immune system to make a humoral and/or cellular antigen-specific response. Normally, an epitope will comprise between about 7 and 15 amino acids, such as, 9, 10, 12 or 15 amino acids. The term "immunogen" includes isolated immunogens as well as inactivated organisms, such as viruses.

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, "about" means ±10% of the indicated range, value, sequence, or structure, unless otherwise indicated. It should be understood that the terms "a" and "an" as used herein refer to "one or more" of the enumerated components unless otherwise indicated or dictated by its context. The use of the alternative (e.g., "or") should be understood to mean either one, both, or any combination thereof of the alternatives unless otherwise indicated.

Aspects of the Disclosure

The invention is based, in part, on the discovery that administration of one or more polypeptides comprising conserved elements, separated by non-naturally occurring linkers and collinearly arranged, from an immunogen of interest, e.g., a viral antigen such as HIV Gag or HIV Env, can provide an enhanced immune response when one or more conserved element nucleic acid constructs is administered to a subject as a prime followed by co-administration to the subject of a nucleic acid construct encoding a full-length antigen, or substantially a full-length antigen, with the conserved element construct(s) as a boost. In typical embodiments, the prime and/or boost components of an immunization protocol in accordance with the invention are administered as nucleic acids that encode the polypeptides. In some embodiments, prime and/or boost immunization components are administered as polypeptides.

The immunogen can be any protein for which it is desired to induce an immune response, but is often a viral protein that exhibits sequence diversity in naturally occurring variants. In some embodiments, the viral protein is a retrovirus protein, such as a lentiviral protein. In some embodiments, the viral protein is a retroviral Gag or Env protein, such as an HIV Gag or HIV Env protein.

The invention is additionally based, in part, on the discovery that administration of one or more polypeptides comprising conserved elements, separated by linkers and collinearly arranged, of HIV Env conserved element proteins as described herein can provide a robust immune response compared to administration of a full-length Env protein to a subject. In some aspects, the disclosure thus provides HIV Env conserved element polypeptides, nucleic acids encoding HIV Env conserved element polypeptides, and methods of using such polypeptide and nucleic acids to induce an immune response.

HIV Env Conserved Element Immunogenic Compositions.

In one aspect, the disclosure provides HIV Env conserved element compositions. In some embodiments, an HIV Env conserved element composition is administered in the form of a nucleic acid construct that encodes an HIV Env conserved element immunogenic polypeptide. Alternatively, the HIV Env conserved element immunogenic composition may may be administered in polypeptide from. Accordingly, the invention provide immunogenic HIV Env conserved element polypeptides and nucleic acid constructs that encode these polypeptides.

A nucleic acid construct encoding an HIV Env conserved element polypeptide in accordance with the invention typically encodes a polypeptide that comprises at least six of the conserved elements set forth in SEQ ID NOS:1-23 and 70-85. In some embodiments, the nucleic acid construct encodes a polypeptide that comprises at least 8, typically, at least 9, 10, 11, 12, 14, 15, 16, 17, 18, 19, 20, 25, 30, 35, or more consecutive amino acids from the conserved elements of SEQ ID NOS:1-23 and 70-85.

In some embodiments, a nucleic acid construct encoding an HIV Env conserved element polypeptide encodes a polypeptide that comprises at least one, two, three, four, five, six, seven, eight, nine, ten, or eleven, or all twelve of the conserved elements set forth in SEQ ID NOs. 1, 2, 4, 6, 8, 10, 12, 14, 16, 18, 20, or 22. In some embodiments, a nucleic acid construct encoding an HIV Env conserved element polypeptide encodes a polypeptide that comprises at least one, two, three, four, five, six, seven, eight, nine, ten, or eleven, or all twelve of the conserved elements set forth in SEQ ID NOs. 1, 3, 5, 7, 9, 11, 13, 15, 17, 19, 21, or 23. In some embodiments, a conserved element sequence has at least 8, typically, at least 9, 10, or 11 consecutive amino acids from CE6 (SEQ ID NO:1). In some embodiments, a conserved element sequence has at least 10, typically at least 11, 12, 13, or 14 consecutive amino acids from CE1 (SEQ ID NO:2 or SEQ ID NO:3). In some embodiments, a conserved element sequence has at least 15, typically at least 16, 17, 18, 19, 20, or 21 consecutive amino acids from CE7 (SEQ ID NO:4 or SEQ ID NO:5). In some embodiments, a conserved element sequence has at least 10, typically at least 11, 12, 13, 14, or 15 consecutive amino acids from CE8 (SEQ ID NO:6 or SEQ ID NO:7). In some embodiments, a conserved element sequence has at least 15, typically at least 16, 17, 18, 19, 20, 21, 22, or 23 consecutive amino acids from CE9 (SEQ ID NO:8 or SEQ ID NO:9). In some embodiments, a conserved element sequence has at least 15, typically at least 16, 17, 18, 19, 20, or 21 consecutive amino acids from CE10 (SEQ ID NO:10 or SEQ ID NO:11). In some embodiments, a conserved element sequence has at least 8, typically, at least 9, 10, 11, 12, or 13 consecutive amino acids from CE11 (SEQ ID NO:12 or SEQ ID NO:13). In some embodiments, a conserved element sequence has at least 8, typically, at least 9, 10, 11, or 12 consecutive amino acids from CE12 (SEQ ID NO:14 or SEQ ID NO:15). In some embodiments, a conserved element sequence has at least 9, typically, at least 10, 11, 12, 13, or 14 consecutive amino acids from CE13 (SEQ ID NO:16 or SEQ ID NO:17). In some embodiments, a conserved element sequence has at least 20, and typically at least 21, 22, 23, 24, 25, 26, 26, 27, 29, 30, 31, 32, 33, 34, 35, 36, 37, 38, 39, 40, 41, 42, or 43 consecutive amino acids from CE4 (SEQ ID NO:18 or SEQ ID NO:19). In some embodiments, a conserved element sequence has at least 15, typically at least 16, 17, 18, 19, or 20 consecutive amino acids from CE15 (SEQ ID NO:20 or SEQ ID NO:21). In some embodiments, a conserved element sequence has at least 8, typically, at least 9, 10, 11, 12, or 13 consecutive amino acids from CE16 (SEQ ID NO:22 or SEQ ID NO:23).

In some embodiments, an HIV Env CE polypeptide may comprise a CE set forth in any one of SEQ ID NOS:70-85. In some embodiments, a conserved element sequence has at least 10, typically, at least 11, 12, 13, 14, 15, or 16 consecutive amino acids of EnvCE17 (SEQ ID NO:70 or SEQ ID NO:71). In some embodiments, a conserved element sequence has at least 20, 21, 22, 23, 24, 25, or 26 consecutive amino acids of CE18 (SEQ ID NO:72 or SEQ ID NO:73). In some embodiments, a conserved element sequence has at least 15, typically at least 16, 17, 18, or 19 consecutive amino acids from CE19 (SEQ ID NO:74 or SEQ ID NO:75). In some embodiments, a conserved element sequence has at least 8, 9, or consecutive amino acids of CE20 (SEQ ID NO:76 or SEQ ID NO:77). In some embodiments, a conserved element sequence has at least 14, typically at least 15, 16, or 17 consecutive amino acids of CE21 (SEQ ID NO:78 or SEQ ID NO:79). In some embodiments, a conserved element sequence has at least 25, typically at least 26, 27, 28, 29, 30, 31, 32, 33, 34, 35, 36, 37, 38, 39, 40, 41, 42, 43, 44, or 45 consecutive amino acids of CE22 (SEQ ID NO:80 or SEQ ID NO:81. In some embodiments, a conserved element sequence has at least 12, typically at least 13, 14, or 15 consecutive amino acids of CE23 (SEQ ID NO:82 or SEQ ID NO:83). In some embodiments, a conserved element sequence has at least 15, typically at least 16, 17, 19, or 19 consecutive amino acids of CE24 (SEQ ID NO:84 or SEQ ID NO:85).

In some embodiments, an HIV Env CE polypeptide comprises the twelve HIV Env conserved element sequences CE6, CE1, CE7, CE8, CE9, CE10, CE11, CE12, CD13, CE14, CE15 and CE16, in this order or in any other order. In some embodiments, an HIV Env CE polypeptide may further comprise HIV Env conserved element sequence CE20 and/or CE23. In some embodiments, an HIV Env CE polypeptide conserved element polypeptide comprises CE17, CE18, CE19, CE21, CE22, and/or CE24 in replace of CE8, CE9, CE10, CE11, CE14, and/or CE15, respectively.

In some embodiments, an HIV Env CE polypeptide of the invention comprises Env conserved elements CE6, CE1, CE7, CE17, CE18, CE19, CE20, CE21, CE12, CE13, CE22, CE23, CE24, and CE16.

In some embodiments, an HIV Env CE polypeptide in accordance with the invention has at least 90%, or at least 91%, 92%, 93%, 94%, 95%, 96%, 97%, 98%, or 99% identity to SEQ ID NO:24 or SEQ ID NO:25. In some embodiments, the HIV Env CE polypeptide has at least 90%, or at least 91%, 92%, 93%, 94%, 95%, 96%, 97%, 98%, or 99% identity to the Env-CE1-V1V2 Bal polypeptide sequence shown in FIG. 25 (SEQ ID NO:69).

In the present disclosure, the HIV Env conserved elements contained within conserved element polypeptides of the invention are not contiguous in the native Env protein sequence. Further, the conserved elements present in an HIV Env conserved element polypeptide are separated by polypeptide sequences that don't naturally occur in native protein sequences. The individual conserved elements are typically joined to one another in the nucleic acid construct by a peptide linker, such as an alanine-containing linker.peptide linker sequences contain Ala and may also include other amino acids such as Gly, Val, Glu, Asp, Lys, or Phe. The linker sequence may range in length, e.g., from 1 to 5 amino acids, or even longer, in length, but is typically no longer than 6, 7, or 8 amino acids in length. In some embodiments, the linker sequence is 3 amino acids in length. In some embodiments, the linker sequence is AAV, AAE, GAK, AAD, AAK, GAV, VAV, or AAF.

The conserved elements may be present in any order in the construct, they need not occur in the order of the naturally occurring sequence. For example, a conserved element that occurs toward the N-terminus of a protein may be encoded at the C-terminal end of the construct.

In some embodiments, a nucleic acid encoding an HIV Env conserved element polypeptide in accordance with the invention encodes a polypeptide that comprises at least five or more, or at least six, seven, eight, nine, ten, or eleven, of the conserved elements set forth in SEQ ID NOS:1, 2, 4, 6, 8, 10, 12, 14, 16, 18, 20, or 22. In some embodiments, a nucleic acid encoding an HIV Env conserved element polypeptide in accordance with the invention encodes a polypeptide that comprises the twelve conserved elements set forth in SEQ ID NOS:1, 2, 4, 6, 8, 10, 12, 14, 16, 18, 20, and 22. In some embodiments, such a nucleic acid construct encodes a polypeptide comprising the amino acid sequence of SEQ ID NO:24. In some embodiments, a nucleic acid encoding an HIV Env conserved element polypeptide in accordance with the invention encodes a polypeptide comprising at least five or more, or at least six, seven, eight, nine, ten, or eleven, of the conserved elements set forth in SEQ ID NOS:1, 3, 5, 7, 9, 11, 13, 15, 17, 19, 21, or 23. In some embodiments, a nucleic acid encoding an HIV Env conserved element polypeptide in accordance with the invention encodes a polypeptide that comprises the twelve conserved elements set forth in SEQ ID NOS:1, 3, 5, 7, 9, 11, 13, 15, 17, 19, 21, and 23. In some embodiments, such a nucleic acid construct encodes a polypeptide that comprises the amino acid sequence of SEQ ID NO:25. In some embodiments, a nucleic acid construct encoding a polypeptide comprising SEQ ID NO:24 is administered in conjunction with a nucleic acid construct encoding a polypeptide comprising SEQ ID NO:25.

In some embodiments, an HIV Env CE polypeptide comprising Env conserved elements SEQ ID NO:1, SEQ ID NO:2, SEQ ID NO:4, SEQ ID NO:70, SEQ ID NO:72, SEQ ID NO:74, SEQ ID NO:76, SEQ ID NO:78, SEQ ID NO:14, SEQ ID NO:16, SEQ ID NO:80, SEQ ID NO:82, SEQ ID NO:84, and SEQ ID NO:22 is administered in conjunction with an HIV Env CE polypeptide comprising SEQ ID NO:1, SEQ ID NO:3, SEQ ID NO:5, SEQ ID NO:71, SEQ ID NO:73, SEQ ID NO:75, SEQ ID NO:77, SEQ ID NO:79, SEQ ID NO:15, SEQ ID NO:17, SEQ ID NO:81, SEQ ID NO:83, SEQ ID NO:85, and SEQ ID NO:23.

In some embodiments, a nucleic acid encoding an HIV Env conserved element polypeptide in accordance with the invention encodes a polypeptide that differs from SEQ ID NO:24 by no more than 1, 2, 3, 4, 5, 6, 7, 8, 9, 10, 11, 12, 13, 14, 15, 16, 17, 18, 19, 20, 21, 22, 23, 24, or 25 amino acids. In some embodiments, a nucleic acid encoding an HIV Env conserved element polypeptide in accordance with the invention encodes a polypeptide that differs from SEQ ID NO:25 by no more than 1, 2, 3, 4, 5, 6, 7, 8, 9, 10, 11, 12, 13, 14, 15, 16, 17, 18, 19, 20, 21, 22, 23, 24, or 25 amino acids.

In some embodiments, an HIV Env conserved element polypeptide further comprises one or more sequences from an HIV Env variable region, e.g., the V1V2 region. The variable region sequences are well known in the art and are bounded by cysteine residues.

In the present disclosure, an HIV Env conserved element nucleic acid construct as described herein is typically employed in a vaccination regimen that also employs a nucleic acid encoding full-length Env protein, or substantially full-length Env protein, from which the conserved elements are obtained. In the context of the present invention, "substantially full-length" refers to the region of the Env protein that includes all of the conserved elements, i.e., a sufficient length of a naturally occurring Env protein is provided that includes all of the conserved elements that are used in the conserved element construct.

Administrative Regimens

In a further aspect, the disclosure provides an enhanced administration regimen for conserved element immunogenic compositions that provides a robust immune response. Thus, the invention additionally provides a method of inducing an immune response, where the method comprises administering one or more nucleic acid constructs encoding a conserved element polypeptide, followed by administering a nucleic acid construct encoding a full-length or substantially full-length polypeptide, where the nucleic acid construct encoding a full-length or substantially full-length polypeptide is administered in conjunction with the nucleic acid construct encoding the conserved element polypeptide.

In some embodiments, the immunogenic compositions employed in the enhanced administration regimens as described in this section relate to a viral protein, e.g., a retrovirus protein such as Gag. Illustrative conserved elements of Gag are described herein. See, also e.g., U.S. Patent Application Publication No. 20110269937; Rolland et al., PLoS Pathog 3: e157, 2007; Mothe et al., PLoS One 7: e29717, 2012; and US20150056237.

Each conserved element included in a CE polypeptide in accordance with the enhanced methods of generating an immune response of the disclosure is generally 50 amino acids or fewer in length, but is at least 8 amino acids in length. In some embodiments, the conserved element is at least 8 amino acids in length and 45, 40, 35, 30, 25, 20, or 15 amino acids, or fewer, in length. In some embodiments, the conserved element is 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 amino acids in length.

In preferred embodiments, more than one nucleic acid construct encoding the conserved elements of interest are used where one construct encodes a first set of conserved elements, e.g., from HIV Gag or HIV Env, and the second construct encodes a second set of conserved elements where one or more elements, often most or all of the conserved elements, of the second set of conserved elements differ from the first set by 5 or fewer amino acids. That is, one conserved element present in the two sets contains a limited number of substitutions (e.g., 1, 2, 3, 4, or 5) relative to the corresponding conserved element. The residues where the sequences differ, however, are at sites of naturally occurring variation in the naturally occurring protein sequences, so that each of the conserved elements in the first and second sets corresponds to a naturally occurring protein sequence. In some embodiments, each element of the second set is at least 80% or at least 90% identical to the corresponding element in the first set of conserved sequences. The nucleic acid construct encoding the first set of conserved elements and the nucleic acid construct encoding the second set of conserved elements may be present in the same vector or different vectors.

As explained above regarding HIV Env conserved element constructs, in the enhanced methods of generating an immune response as described herein, the conserved elements contained within conserved element polypeptides are not contiguous in the naturally occurring protein sequence. Further, the conserved elements present in a conserved element polypeptide generated in accordance with the invention are separated by polypeptide sequences that do not naturally occur in the protein sequence. The individual conserved elements are typically joined to one another in the nucleic acid construct by a peptide linker, such as an alanine-containing linker. Linker sequences are well known in the art. Typical peptide linker sequences contain Ala and may also include other amino acids such as Gly, Val, Glu, Asp, Lys, or Phe. The linker sequence may range in length, e.g., from 1 to 5 amino acids, or even longer, in length, but is typically no longer than 6, 7, or 8 amino acids in length. In some embodiments, the linker sequence is 3, 4, or 5 amino acids in length. In some embodiments, the linker sequence is AAV, AAE, GAK, AAD, AAK, GAV, VAV, or AAF. In some embodiments, the linker is AA, AAAE, AAAA, AAK, AG, AA, LAK, AAK, AAAAL, and the like.

The conserved elements may be present in any order in the construct, they need not occur in the order of the naturally occurring sequence. For example, a conserved element that occurs toward the N-terminus of a protein may be encoded at the C-terminal end of the construct.

In some embodiments, the protein of interest is HIV Gag. A nucleic acid construct encoding a conserved element polypeptide for use in the invention encodes a polypeptide that comprises at least one, two, three, four, five, six, or seven conserved elements set forth in Table 2. In some embodiments, the nucleic acid construct encodes a polypeptide that comprises at least 8, typically, at least 9, 10, 11, 12, 14, 15, 16, 17, 18, 19, 20, or more consecutive amino acids from a conserved element set forth in Table 2. See also, e.g. US20150056237, incorporated by reference, which teaches HIV Gag conserved elements. In some embodiments, a Gag CE polypeptide used in accordance with the methods of the invention comprises a p24Gag CE polypeptide having the sequence of the p24GagCE1 polypeptide of Table 2:

(SEQ ID NO: 40)
VIPMFSALSEGATPQDLNAAVGGHQAAMQMLKDTINEEAAEWDRAAAEP
RGSDIAGTTSTLQEQIGWAAAKRWIILGLNKIVRMYSPTSIAAKYVDRF
YKTLRAEQAAGLEEMMTACQGVGGPGHKAAISPRTLNAWVKV.

In some embodiments, a Gag CE polypeptide used in accordance with the methods of the invention comprises a p24Gag CE polypeptide having the sequence of the p24GagCE2 polypeptide of Table 2:

(SEQ ID NO: 41)
VIPMFTALSEGATPQDLNAAVGGHQAAMQMLKETINEEAAEWDRAAAEP
RGSDIAGTTSTLQEQIAWAAAKRWIILGLNKIVRMYSPVSIAAKYVDRF
FKTLRAEQAAGLEEMMTACQGVGGPSHKAALSPRTLNAWVKV.

In some embodiments, a nucleic acid encoding an HIV Gag conserved element polypeptide for use in the invention encodes a polypeptide that comprises the conserved elements set forth in Table 2 SEQ ID NOS:26-32. In some embodiments, such a nucleic acid construct encodes a polypeptide comprising the amino acid sequence of p24 Gag CE1 as shown in Table 2. In some embodiments, a nucleic acid encoding a conserved element encodes a polypeptide comprising the conserved elements set forth in SEQ ID NOS:33-39. In some embodiments, such a nucleic acid construct encodes a polypeptide that comprises the p24 Gag CE2 amino acid sequence as shown in Table 2. In some embodiments, a nucleic acid construct encoding a polypeptide comprising the p24 Gag CE1 sequences SEQ ID NOs 26-32 set forth in Table 2 is administered with a nucleic acid construct encoding a polypeptide comprising the p24 Gag CE2 sequences SEQ ID NOS:33-39 set forth in Table 2. In some embodiments, the nucleic acid sequence encoding p24gag CE1 is present in the same vector as the nucleic acid sequence encoding p24gag CE2.

In some embodiments, a nucleic acid encoding p24GagCE1 as set forth in Table 2 is co-administered with a nucleic acid encoding p24GagCE2 as set forth in Table 2 where each of the p24GagCE1 and p24GagCE2 polypeptides is expressed as a fusion protein having a human GM-CSF signal peptide at the N-terminus.

In some embodiments, a nucleic acid encoding a Gag conserved element polypeptide encodes at least one conserved element set forth in the alternative CE sequences shown in Table 2.

In some embodiments, an immunogen of interest is HIV Env. In some embodiments, a nucleic acid construct encoding an HIV Env conserved element polypeptide employed in accordance with the invention typically encodes a polypeptide that comprises a conserved element as described herein. Thus, in some embodiments, the nucleic acid construct encodes a polypeptide that comprises at least 8, typically, at least 9, 10, 11, 12, 13, 14, 15, 16, 17, 18, 19, 20, 25, 30, 35, or more consecutive amino acids from the Env conserved elements shown in Table 1. In some embodiments, an Env CE polypeptide used in accordance with the methods of the invention comprises an Env CE1 polypeptide comprising 12 conserved element: CE6, CE1-1, CE7-1, CE8-1, CE9-1, CE10-1, CE11-1, CE12-1, CE13-1, CE14-1, CE15-1, and CE16-1 as shown in Table 1. In some embodiments, the Env CE1 polypeptide comprises the Env CE1 polypeptide sequence of Table 1 (linkers are underlined):

```
WVTVYYGVPVWAAVHNVWATHACVPTDPAAEISLWDQSLKPCVKLTPLC
VTLGAKFEPIPIHYCTPAGFAGAKVQCTHGIRPVVSTQLLLNGSLAEAA
DSGGDPEIVMHSFNCGGEFFYCGAKDNWRSELYKYKVVAAKARRRVVQR
EKRAGAVGFLGTAGSTMGAASVAVLTVQARLLLSGIVQQQNNLLRAIEA
QQHLLQLTVWGIKQLQARAADWLWYIKIFIMIVGGLVGLRIAAFRVRKG
YSPLSLQT.
```

In some embodiments, an Env CE polypeptide used in accordance with the methods of the invention comprises an Env CE2 polypeptide comprising 12 conserved element: CE6, CE1-2, CE7-2, CE8-2, CE9-2, CE10-2, CE11-2, CE12-2, CE13-2, CE14-2, CE15-2, and CE16-2 as shown in Table 1. In some embodiments, the Env CE2 polypeptide comprises the sequence of the Env CE2 polypeptide of Table 1 (linkers are underlined):

```
WVTVYYGVPVWAAVHNIWATHACVPTDPAAEISLWDESLKPCVKLTPLC
VTLGAKFDPIPIHYCAPAGYAGAKVQCTHGIKPVVSTQLLLNGSLAEAA
```

-continued

```
DAGGDLEITTHSFNCRGEFFYCGAKNNWRSELYKYKVVAAKAKRRVVER
EKRAGAVGFLGAAGSTMGAASVAVLTVQARQLLSGIVQQQSNLLKAIEA
QQHMLQLTVWGIKQLQTRAADWLWYIRIFIMIVGGLIGLRIAAFRVRQG
YSPLSFQT.
```

In some embodiments, a nucleic acid encoding an HIV Env conserved element polypeptide for use in accordance with the disclosure encodes a polypeptide that comprises at the twelve conserved elements set forth in SEQ ID NOS:1, 2, 4, 6, 8, 10, 12, 14, 16, 18, 20, and 22. In some embodiments, a nucleic acid encoding an HIV Env conserved element polypeptide in accordance with the disclosure encodes a polypeptide comprising the twelve conserved elements set forth in SEQ ID NOS:1, 3, 5, 7, 9, 11, 13, 15, 17, 19, 21, and 23.

In some embodiments, an HIV Env CE polypeptide comprising Env conserved elements SEQ ID NO:1, SEQ ID NO:2, SEQ ID NO:4, SEQ ID NO:39, SEQ ID NO:41, SEQ ID NO:43, SEQ ID NO:45, SEQ ID NO:47, SEQ ID NO:14, SEQ ID NO:16, SEQ ID NO:49, SEQ ID NO:51, SEQ ID NO:53, and SEQ ID NO:22 is administered in conjunction with an HIV Env CE polypeptide comprising SEQ ID NO:1, SEQ ID NO:3, SEQ ID NO:5, SEQ ID NO:40, SEQ ID NO:42, SEQ ID NO:44, SEQ ID NO:46, SEQ ID NO:48, SEQ ID NO:15, SEQ ID NO:17, SEQ ID NO:50, SEQ ID NO:52, SEQ ID NO:54, and SEQ ID NO:23.

In some embodiments, a nucleic acid encoding an HIV Env conserved element polypeptide in accordance with the invention encodes a polypeptide that differs from SEQ ID NO:24 by no more than 1, 2, 3, 4, 5, 6, 7, 8, 9, 10, 11, 12, 13, 14, 15, 16, 17, 18, 19, 20, 21, 22, 23, 24, or 25 amino acids. In some embodiments, a nucleic acid encoding an HIV Env conserved element polypeptide in accordance with the invention encodes a polypeptide that differs from SEQ ID NO:25 by no more than 1, 2, 3, 4, 5, 6, 7, 8, 9, 10, 11, 12, 13, 14, 15, 16, 17, 18, 19, 20, 21, 22, 23, 24, or 25 amino acids.

An HIV Env conserved element construct can be administered in conjunction with immunogenic constructs to induce immune response to additional regions of HIV, e.g., Gag or a non-structural protein such as Nef. In typical embodiments, the additional immunogenic compositions encode conserved element polypeptides to the HIV protein of interest, e.g., Gag.

In some aspects, the disclosure further provides Gag conserved elements in addition to those described above for use in a CE immunogenic compositions. In some embodiments, an HIV Gag CE polypeptide comprises a CE as set forth below:

```
p24CE8-1
                                   (SEQ ID NO: 57)
QPISPRTLNAWVKV

p24CE8-2
                                   (SEQ ID NO: 58)
QALSPRTLNAWVKV

p24CE9-1
                                   (SEQ ID NO: 59)
EEKAFSPEVIPMFSALSEGATPQDLNTMLN
```

-continued p24CE9-2

(SEQ ID NO: 60)

EEKGFNPEVIPMFTALSEGATPQDLNMMLN p24CE10-1

(SEQ ID NO: 61)

PRGSDIAGTTSTLQEQIGWMT p24CE10-2

(SEQ ID NO: 62)

PRGSDIAGTTSTLQEQIAWMT p24CE11-1

(SEQ ID NO: 63)

SILDIRQGPKEPFRDYVDRF p24CE11-2

(SEQ ID NO: 64)

SILDIKQGPKEPFRDYVDRF p24CE12-1

(SEQ ID NO: 65)

QNSNPDCKTILKALG p24CE12-2

(SEQ ID NO: 66)

QNANPDCKTILKALG p24CE13-1

(SEQ ID NO: 67)

LEEMMTACQGVGGPGHKARILAEAM p24CE13-2

(SEQ ID NO: 68)

LEEMMTACQGVGGPSHKARVLAEAM.

Thus, in one aspect the disclosure provides an HIV Gag CE polypeptide that comprises one or more, or two, or three, or four, or five, or all of, the CEs of SEQ ID NOs:57, 59, 61, 63, 65, or 67; or one or more, or two, or three, or four, or five, or all of, the CEs of SEQ ID NOs:58, 60, 62, 64, 66, or 68.

These alternative CE elements are typically employed with Gag CE elements from U.S. Patent Application Publication No. 20150056237, the sequences of which are shown in FIG. 23.

In some embodiments, the invention provides Gag CE polypeptides that include the following CE:

P24CE8-1, p24CE9-1, p24CE3-1, p24CE10-1, p24CE5-1, p24CE11-1, p24CE6-1, p24CE12-1, p24CE13-1; or a Gag CE polypeptide that comprises P24CE8-2, p24CE9-2, p24CE3-2, p24CE10-2, p24CE5-2, p24CE11-2, p24CE6-2, p24CE12-2, p24CE13-2. The two polypeptides are typically used in conjunction with one another to cover almost all of the diversity observed in those conserved elements in naturally occurring HIV Gag sequences. Each of the two Gag CE polypeptides include CE elements that correspond to one another, but that different at a small number of amino acid positions (see, FIG. 23). In some embodiments, the CE of a Gag CE polypeptide may be presented in an order that differs from the order shown for the illustrative Gag CE polypeptides above.

In some embodiments, an HIV Gag CE polypeptide may comprise p24CE8 instead of p24CE1; p24CE9 instead of p24CE2; and/or p24CE13 instead of p24CE7 as shown in FIG. 23. In some embodiments, an HIV Gag CE polypeptide may additionally comprise CE12, and CE6. In some embodiments, an HIV Gag CE polypeptide may additionally comprise CE11.

In the present disclosure, a conserved element nucleic acid construct is employed in an immunization regimen that also employs a nucleic acid encoding full-length protein, or substantially full-length protein, from which the conserved elements are obtained. In the context of the present disclosure, "substantially full-length" refers to the region of the protein that includes all of the conserved elements, i.e., a sufficient length of a naturally occurring protein is provided that includes all of the conserved elements that are used in the conserved element construct. In the present disclosure, administration of a nucleic acid construct encoding a full-length protein excludes administration of a viral genome, e.g., an HIV genome, that comprises a nucleic acid sequence that encodes the protein. In some embodiments, a nucleic acid construct used in accordance with a treatment protocol of the present disclosure that encodes a full-length Gag or Env protein may also encode additional viral proteins, but does not encode a full complement of viral proteins. For example, such a nucleic acid construct may exclude sequences that encode one or more regulatory polypeptides such as Tat.

A nucleic acid construct encoding a full-length protein, or substantially full-length protein, is administered following administration of the one or more constructs encoding the CE polypeptide(s), such that the CE polypeptide(s) acts as a prime and the full-length polypeptide, or substantially full-length polypeptide, is a boost. In the present disclosure, the boost preferably comprises co-administering the one or more nucleic acid constructs encoding CE polypeptide(s) with the nucleic acid construct encoding the full-length polypeptide, or substantially full-length polypeptides. The boost is typically administered anywhere from about one, about two, about three, or about four months; or even about one year, or longer, following administration of the initial priming vaccines. Multiple boost vaccinations may be used, and different full-length proteins may be used in a sequence of boosts. A priming vaccination can itself be one or multiple, e.g., 2, 3, 4, or 5, administrations of the CE polypeptide(s). CE polypeptides and a full-length polypeptide, or substantially full-length polypeptide, are preferably administered to the host by way of administration of expression constructs that encode the polypeptides, although in some embodiments, the polypeptides are administered in a protein form. Protein forms may be employed in either the priming or boosting administrations.

In the present disclosure, nucleic acid constructs encoding the CE polypeptides that are administered in the priming component of the vaccine regimen are administered first, i.e., the subject has not been administered a nucleic acid that encodes the full-length, or substantially full-length, polypeptide either prior to or concurrently with administration of the CE constructs. Thus, for example, a method of the invention for inducing an immune response in the subject can comprise administering one or more nucleic acid constructs encoding a Gag CE polypeptide construct as the priming immunization followed by administration of a full-length, or substantially full-length Gag polypeptide as a boosting step, where the boosting step also comprises co-administration of the CE constructs again.

The initial priming administration of the CE constructs may also comprise administering CE constructs for another polypeptide for which it is desired to elicit an immune response. Thus, one or more Gag CE constructs may be administered sequentially or concurrently with one or more Env CE constructs in the initial priming phase of the vaccination regimen. As noted above, the priming administration occurs before administration of either full-length, or substantially full-length, form of either antigen.

Nucleic acids encoding multiple CE polypeptides, typically two CE polypeptides, i.e., a conserved element polypeptide pair, are administered in combination. In the context of the current invention, nucleic acid constructs encoding CE polypeptides "administered in combination", also referred to herein as "co-administration", may be administered together or separately. For example, a nucleic acid construct encoding a second CE polypeptide may be administered after (e.g., anywhere from 1 minutes to 60 minutes, 1 hour, 2 hours, 4 hours, 6 hours, 12 hours, 24 hours, 48 hours, or up to 2 weeks) administration of a first nucleic acid construct encoding a CE polypeptide, but is typically administered at the same time as the first nucleic acid construct. In some embodiments, the nucleic acid construct encoding the second CE polypeptide is administered within 24 hours of administration of the nucleic acid construct encoding the first CE polypeptide.

Similarly, for co-administration of one or more CE polypeptides with the full-length, or substantially full-length polypeptide, administered as the boost, the co-administration may be formed by administering the constructs together, or they may be administered separately. For example, one or more nucleic acid constructs encoding a CE polypeptide(s) may be administered shortly before (e.g., anywhere from 1 minutes to 60 minutes, 1 hour, 2 hours, 4 hours, 6 hours, 12 hours, usually within 24 hours) or after, a nucleic acid construct encoding the full-length polypeptide, or the substantially full-length polypeptide.

In some embodiments, in a boosting administration, the one or more CE nucleic acid constructs are co-delivered with a nucleic acid construct encoding a full-length, or substantially full-length, protein. In the context of this disclosure, "co-delivery" refers to administering the nucleic acid constructions together at the same site, e.g., administering them in the same mixture.

In some embodiments, a nucleic acid immunization regimen in accordance with the disclosure comprises performing at least two priming administrations with one or more CE nucleic acids constructs, which encode a conserved element pair, either on separate vectors or the same vector, followed by performing at least two boosting administrations of the CE nucleic acid construct(s) co-delivered with the construct encoding the full-length polypeptide or substantially full-length polypeptide. In some embodiments, priming vaccinations can be performed at least about two weeks apart. In some embodiments, priming vaccinations are performed at least about one month apart or separated by several months. Boost vaccinations are typically administered at least about one month, often at least about 2, 3, 4, 5, 6, 7, 8, 9, 10, or 11 months; or 1 or more years after the priming vaccinations.

In the methods of the disclosure, a nucleic acid construct encoding a CE polypeptide is directly introduced into the cells of the individual receiving the immunogenic composition, i.e., the CE polypeptide is administered to the host via expression in the host cells of the nucleic acid construct encoding the polypeptide. This approach is described, for instance, in Wolff et. al., *Science* 247:1465 (1990) as well as U.S. Pat. Nos. 5,580,859; 5,589,466; 5,804,566; 5,739,118; 5,736,524; 5,679,647; and WO 98/04720. Examples of DNA-based delivery technologies include, "naked DNA", facilitated (bupivicaine, polymers, peptide-mediated) delivery, and cationic lipid complexes or liposomes. In some embodiments, nucleic acids are administered using ballistic delivery as described, for instance, in U.S. Pat. No. 5,204,253 or pressure (see, e.g., U.S. Pat. No. 5,922,687).

In some embodiments, the immunogenic compositions of the disclosure are administered by injection or electroporation, or a combination of injection and electroporation. For example, the nucleic acid can be administered using intramuscular or intradermal injection and may include in vivo electroporation to enhance DNA uptake.

In some embodiments, e.g., where a nucleic acid construct of the invention is encoded by a viral vector, the nucleic acid construct can be delivered by infecting the cells with the virus containing the vector. This can be performed using well-known delivery For embodiments that employ administration of a polypeptide as a protein form, rather than expressing the protein in the host cell using a nucleic acid construct, the proteins are typically produced in an in vitro cell expression system and isolated for administration to the subject. Such cellular expression systems are well known in the art.

Nucleic acid constructs may be employed as plasmid expression vectors or may be administered as a virus. In some embodiments, the nucleic acid constructs encoding the conserved elements and/or full-length HIV polypeptides are one or more purified nucleic acid molecules, for example, one or more DNA plasmid-based vectors ("naked" DNA).

In some embodiments, a nucleic acid construct encoding a CE immunogenic polypeptide is contained within a viral vector and administered as a virus. Viral delivery systems include adenovirus vectors, adeno-associated viral vectors, herpes simplex viral vectors, retroviral vectors, pox viral vectors, lentiviral vectors, alphavirus vectors, poliovirus vectors, and other positive and negative stranded RNA viruses, viroids, and virusoids, or portions thereof. Methods of constructing and using such vectors are well known in the art.

For example, recombinant viruses in the pox family of viruses can be used for delivering the nucleic acid molecules. These include vaccinia viruses and avian poxviruses, such as the fowlpox and canarypox viruses. Methods for producing recombinant pox viruses are known in the art and employ genetic recombination. See, e.g., WO 91/12882; WO 89/03429; and WO 92/03545. A detailed review of this technology is found in U.S. Pat. No. 5,863,542. Representative examples of recombinant pox viruses include ALVAC, TROVAC, and NYVAC.

A number of adenovirus vectors, including Ad2, Ad5, and Ad7 have also been described that can be used to deliver one or more of the nucleic acid constructs as described herein (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell. Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Retroviruses also provide a platform for gene delivery systems. A number of retroviral systems have been described (U.S. Pat. No. 5,219,740; Miller and Rosman, BioTechniques (1989) 7:980-990; Miller, A. D., Human Gene Therapy (1990) 1:5-14; Scarpa et al., Virology (1991)

180:849-852; Burns et al., Proc. Natl. Acad. Sci. USA (1993) 90:8033-8037; and Boris-Lawrie and Temin, Cur. Opin. Genet. Develop. (1993) 3:102-109. Additional gene delivery systems include lentiviral vectors that employ lentiviral vector backbones.

Members of the Alphavirus genus, such as, but not limited to, vectors derived from the Sindbis, Semliki Forest, and Venezuelan Equine Encephalitis viruses, can also be used as viral vectors to deliver one or more nucleic acid constructs of the disclosure. For a description of Sindbis-virus derived vectors useful for the practice of the instant methods, see, Dubensky et al., J. Virol. (1996) 70:508-519; and International Publication Nos. WO 95/07995 and WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998).

Expression Constructs Encoding Fusion Polypeptides Comprising a Degradation Signal or Signal Peptide Sequence In some embodiments, a nucleic acid encoding a conserved element polypeptide encodes a form in which the conserved element is fused to a sequence to enhance the immune response, such as a signal peptide sequence or a sequence that targets the protein for lysosomal degradation. Such embodiments typically results in enhanced immune responses in comparison to embodiments where the conserved element vaccine is not fused to a signal peptide or degradation signal.

Lysosomal Targeting Sequence

In some embodiments, signals that target proteins to the lysosome may be employed. For example, the lysosome associated membrane proteins 1 and 2 (LAMP-1 and LAMP-2) include a region that targets proteins to the lysosome. Examples of lysosome targeting sequences are provided, e.g., in U.S. Pat. Nos. 5,633,234; 6,248,565; and 6,294,378.

Destabilizing sequences present in particular proteins are well known in the art. Exemplary destabilization sequences include c-myc aa 2-120; cyclin A aa 13-91; Cyclin B aa 13-91; IkBα aa 20-45; β-Catenin aa 19-44; β-Catenin aa 18-47, c-Jun aa1-67; and c-Mos aa1-35; and fragments and variants, of those segments that mediate destabilization. Such fragments can be identified using any method. For example, polypeptide half-life can be determined by a pulse-chase assay that detects the amount of polypeptide that is present over a time course using an antibody to the polypeptide, or to a tag linked to the polypeptide. Exemplary assays are described, e.g., in WO02/36806, which is incorporated by reference.

Variants of such sequences, e.g., that have at least 90% identity, usually at least 91%, 92%, 93%, 94%, 95%, 96%, 97%, 98%, 99%, or greater, identity to the sequences noted above, e.g., a LAMP degradation sequence, can be employed in this invention.

Additional degradation signals that can be used to modify retroviral antigens, e.g., HIV antigens in accordance with the invention include the F-box degradation signal, such as the F-BOX signal 47aa (182-228) from protein beta-TrCP (Liu, et al., *Biochem Biophys Res Comm.* 313:1023-1029, 2004). Accordingly, in some embodiments, an expression vector for use in the invention may encode a fusion protein where an F-box degradation signal is attached to an HIV polypeptide, e.g., an HIV Env CE polypeptide as described herein.

Targeting to the Proteasome and Other Degradation Signals

Many polypeptide sequences that target a protein for degradation are known in the art. One example of destabilizing sequences are so-called PEST sequences, which are abundant in the amino acids Pro, Asp, Glu, Ser, Thr (they need not be in a particular order), and can occur in internal positions in a protein sequence. A number of proteins reported to have PEST sequence elements are rapidly targeted to the 26S proteasome. A PEST sequence typically correlates with a) predicted surface exposed loops or turns and b) serine phosphorylation sites, e.g., the motif S/TP is the target site for cyclin dependent kinases.

Additional destabilization sequences relate to sequences present in the N-terminal region. In particular the rate of ubiquitination, which targets proteins for degradation by the 26S proteasome can be influenced by the identity of the N-terminal residue of the protein. Thus, destabilization sequences can also comprise such N-terminal residues, "N-end rule" targeting (see, e.g., Tobery et al., *J. Exp. Med.* 185:909-920).

Other targeting signals include the destruction box sequence that is present, e.g., in cyclins. Such a destruction box has a motif of 9 amino acids, R1(A/T)2(A)3L4(G)5X6 (I/V)7(G/T)8(N)9, in which the only invariable residues are R and L in positions 1 and 4, respectively. The residues shown in parenthesis occur in most destruction sequences. (see, e.g., Hershko & Ciechanover, *Annu. Rev. Biochem.* 67:425-79, 1998). In other instances, destabilization sequences lead to phosphorylation of a protein at a serine residue (e.g., Ma).

In some embodiments, a conserved element polypeptide of the invention is fused to a LAMP degradation sequence. For example, the methods of the invention may employ a polypeptide in which SEQ ID NO:24 or SEQ ID NO:25, or SEQ ID NO:40 or 41, is fused to a LAMP degradation sequence.

Expression Constructs that Encode Secreted Fusion Proteins

A secretory polypeptide in the context of this invention is a polypeptide signal sequence that results in secretion of the protein to which it is attached. In some embodiments, the secretory polypeptide is a chemokine, cytokine, or lymphokine, or a fragment of the chemokine, cytokine, or lymphokine that retains immunostimulatory activity. Examples of chemokine secretory polypeptides include MCP-3 and IP-10. In other embodiments, the secretory polypeptide is a polypeptide signal sequence from a secreted protein such as tissue plasminogen activator (tPA) protein, growth hormone, GM-CSF, a cytokine, or an immunoglobulin protein. Constructs encoding secretory fusion proteins are disclosed, e.g., in WO02/36806.

In some embodiments, the signal peptide is a GM-CSF sequence, e.g., a mammalian GM-CSF sequence such as a human GM-CSF signal peptide sequence.

In some embodiments, a secretory signal for use in the invention is MCP-3 amino acids 33-109, e.g., linked to an IP-10 secretory peptide.

In some embodiments, a conserved element polypeptide may SEQ ID NO:24 fused to a signal peptide; or may comprise SEQ ID NO:25 fused to a signal peptide. The signal peptide may be a native HIV Env signal peptide or a heterologous signal peptide. In some embodiments, a conserved element polypeptide may SEQ ID NO:40 fused to a signal peptide; or may comprise SEQ ID NO:41 fused to a signal peptide. The signal peptide may be a native HIV signal peptide or a heterologous signal peptide.

Similarly, an expression construct encoding a full-length polypeptide, or substantially full-length polypeptide, may also be modified with a secretory sequence, e.g., a heterologous signal peptide or degradation peptide sequence. Moreover, more than one construct encoding the full-length polypeptide, or substantially full-length polypeptides may be administered. For example, a construct in which Gag (or Env) is fused to a signal polypeptide may be used in conjunction with a construct in which Gag (or ENv) is fused to a degradation sequence.

Additional Properties of Expression Constructs

Within each expression cassette, sequences encoding an antigen for use in the nucleic acid vaccines of the invention will be operably linked to expression regulating sequences. "Operably linked" sequences include both expression control sequences that are contiguous with the nucleic acid of interest and expression control sequences that act in trans or at a distance to control the gene of interest. Expression control sequences include appropriate transcription initiation, termination, promoter and enhancer sequences; efficient RNA processing signals such as splicing and polyadenylation signals; sequences that stabilize cytoplasmic mRNA; sequences that promote RNA export (e.g., a constitutive transport element (CTE), a RNA transport element (RTE), or combinations thereof; sequences that enhance translation efficiency (e.g., Kozak consensus sequence); sequences that enhance protein stability; and when desired, sequences that enhance protein secretion.

Any of the conventional vectors used for expression in eukaryotic cells may be used for directly introducing nucleic acids into tissue. Expression vectors containing regulatory elements from eukaryotic viruses are often used in eukaryotic expression vectors. Such regulatory elements include, e.g., human CMV, simian CMV, viral LTRs, and the like. Typical vectors may comprise, e.g., those with a human CMV promoter, bovine growth hormone polyA site and an antibiotic resistance gene for selective growth in bacteria.

Other expression vector components are well known in the art, including, but not limited to, the following: transcription enhancer elements, transcription termination signals, polyadenylation sequences, splice sites, sequences for optimization of initiation of translation, and translation termination sequences.

In some embodiments, the nucleic acid component may comprise one or more RNA molecules, such as viral RNA molecules or mRNA molecules that encode the antigen of interest.

In typical embodiments, the nucleic acid constructs are codon-optimized for expression in a human.

As noted here, in the present disclosure, a "nucleic acid" molecule can include cDNA and genomic DNA sequences, RNA, and synthetic nucleic acid sequences. Thus, "nucleic acid" also encompasses embodiments in which analogs of DNA and RNA are employed.

An immunogenic composition of the invention can be administered as one or more constructs. For example, where two sets of conserved elements are employed, e.g., HIV Env conserved element polypeptides of SEQ ID NOS:24 and 25, or HIV Gag conserved element polypeptides of SEQ ID NOS: 40 and 41, nucleic acid construct can encode both sets, or each set may be encoded by a separate expression vector. Thus, the expression constructs administered in accordance with the invention may be administered as multiple expression vectors, or as one or more expression vectors encoding multiple expression units, e.g., a discistronic, or otherwise multicistronic, expression vectors. For example, an expression vector may be employed that encodes both SEQ ID NO:24 and SEQ ID NO:25 or multiple expression vectors may be employed where SEQ ID NO:24 is encoded by one vector and SEQ ID NO:25 is encoded by another vector. Similarly, an expression vector may be employed that encodes both SEQ ID NO:40 and SEQ ID NO:41 or multiple expression vectors may be employed where SEQ ID NO:40 is encoded by one vector and SEQ ID NO:41 is encoded by another vector.

In some embodiments, multiple nucleic acid constructs that encode an HIV Gag or Env CE polypeptide may be employed. For example, a nucleic acid construct that encodes an HIV-Env CE polypeptide fused to a signal peptide may be used in combination with a nucleic acid construct that encodes the HIV-Env CE polypeptide fused to a degradation signal; and/or a nucleic acid construct that encodes an HIV-Gag CE polypeptide fused to a signal peptide may be used in combination with a nucleic acid construct that encodes the HIV-Gag CE polypeptide fused to a degradation signal. Thus, multiple constructs that encode a desired HIV CE polypeptide may be used in a vaccine.

Administration of Immunogenic Compositions as Peptides

In some embodiments, CE polypeptides, e.g., HIV Gag or Env CE polypeptides as of the present disclosure, are administered to a subject in the form of a protein. Thus, in some embodiments, a subject is administered multiple, typically two, HIV CE polypeptides. As explained in the context of the administration of a nucleic acid construct, CE polypeptides "administered in combination" may be administered together or separately. For example, a first CE polypeptide may be administered prior to (e.g., anywhere from 1 minutes to 60 minutes, 1 hour, 2 hours, 4 hours, 6 hours, 12 hours, 24 hours, 48 hours, 72 hours, 96 hours, or 1 week, or more) administration of a second CE polypeptide.

A full-length protein or substantially full-length protein may also be administered in the form of a protein. In one embodiment, a full-length polypeptide or substantially full-length polypeptide is administered following administration of a CE polypeptide, such that the CE polypeptide acts as a prime and the full-length polypeptide, or substantially full-length polypeptide is a boost. In preferred embodiments, the full-length or substantially full-length polypeptide is administered in a boosting step that also comprises administration of the CE polypeptide(s). The boost is typically administered anywhere from two weeks to one, two, three, or four months, or longer, following administration of the initial priming vaccines. A priming vaccination can itself be one or multiple administrations of the CE polypeptide. In some embodiments, a boost of a full-length, or substantially full-length, polypeptide is administered in combination with a further administration of the CE polypeptide (s), such that the CE polypeptide is not only administered as a priming step, but as part of the boosting step that comprises administering full-length, or substantially full-length polypeptide.

In some embodiments, both nucleic acids CE polypeptides in accordance with the disclosure and protein forms of the CE polypeptides may be administered to a subject at various times in a vaccination regimen. Similarly, nucleic acid constructs encoding a full-length protein, or substantially full-length protein, may be used in vaccine regimens that also employ protein forms of the full-length protein, or substantially full-length protein. In some embodiments, a full-length protein may be administered in the form of a viral particle.

Assessment of Immunogenic Response

To assess a patient's immune system during and after treatment and to further evaluate the treatment regimen, various parameters can be measured. Measurements to evaluate immunogenic responses include: antibody measurements in the plasma, serum, or other body fluids; analysis of in vitro cell proliferation in response to a specific antigen, indicating the function of CD4+ cells, and analysis of CD8+ responses. Such assays are well known in the art.

For example, for measuring CD4+ T cells, many laboratories measure absolute CD4+ T-cell levels in whole blood by a multi-platform, three-stage process. Systems for measuring CD4+ cells are commercially available. For example commercially available FAC systems are available that automatically measure absolutes CD4+, CD8+, and CD3+ T lymphocytes.

Other measurements of immune response include assessing CD8+ responses. These techniques are well known. CD8+ T-cell responses can be measured, for example, by using tetramer staining of fresh or cultured PBMC (see, e.g., Altman, et al., *Proc. Natl. Acad. Sci. USA* 90:10330, 1993; Altman, et al., *Science* 274:94, 1996), or 7-interferon release assays such as ELISPOT assays (see, e.g., Lalvani, et al., *J. Exp. Med.* 186:859, 1997; Dunbar, et al., *Curr. Biol.* 8:413, 1998; Murali-Krishna, et al., *Immunity* 8:177, 1998), or by using functional cytotoxicity assays.

Viral Titer

Viremia is measured by assessing viral titer in a patient. There are a variety of methods of perform this. For example, plasma HIV RNA concentrations can be quantified by either target amplification methods (e.g., quantitative RT polymerase chain reaction [RT-PCR], Amplicor HIV Monitor assay, Roche Molecular Systems; or nucleic acid sequence-based amplification, [NASBA®], NucliSens™ HIV-1 QT assay, Organon Teknika) or signal amplification methods (e.g., branched DNA [bDNA], Quantiplex™ HIV RNA bDNA assay, Chiron Diagnostics). The bDNA signal amplification method amplifies the signal obtained from a captured HIV RNA target by using sequential oligonucleotide hybridization steps, whereas the RT-PCR and NASBA® assays use enzymatic methods to amplify the target HIV RNA into measurable amounts of nucleic acid product. Target HIV RNA sequences are quantitated by comparison with internal or external reference standards, depending upon the assay used.

Administration of Nucleic Acid Constructs

Nucleic acids for administration to a subject are formulated for pharmaceutical administration. While any suitable carrier known to those of ordinary skill in the art may be employed in the pharmaceutical compositions of this invention, the type of carrier will vary depending on the mode of administration. For parenteral administration, including intranasal, intradermal, subcutaneous or intramuscular injection or electroporation, the carrier preferably comprises water, saline, and optionally an alcohol, a fat, a polymer, a wax, one or more stabilizing amino acids or a buffer. General formulation technologies are known to those of skill in the art (see, for example, Remington: The Science and Practice of Pharmacy ($22^{nd}$ edition), Allan, ed; 2012, Lippincott Williams & Wilkins; Injectable Dispersed Systems: Formulation, Processing And Performance, Burgess, ed., 2005, CRC Press; and Pharmaceutical Formulation Development of Peptides and Proteins, 2000, Taylor & Francis).

DNA immunogenic compositions can be administered once or multiple times. DNA vaccination is performed more than once, for example, 2, 3, 4, 5, 6, 7, 8, 10, 15, 20 or more times as needed to induce the desired response (e.g., specific antigenic response or proliferation of immune cells). Multiple administrations can be administered, for example, bi-weekly, weekly, bi-monthly, monthly, or more or less often, as needed, for a time period sufficient to achieve the desired response.

The nucleic acid constructs in accordance with the invention are administered to a mammalian host. The mammalian host usually is a human or a primate. In some embodiments, the mammalian host can be a domestic animal, for example, canine, feline, lagomorpha, rodentia, rattus, hamster, murine. In other embodiment, the mammalian host is an agricultural animal, for example, bovine, ovine, porcine, equine, etc.

Immunogenic compositions containing the DNA expression constructs can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular patient, and the route of administration.

In therapeutic applications, the vaccines are administered to a patient in an amount sufficient to elicit a therapeutic effect, e.g., a $CD8^+$, $CD4^+$, and/or antibody response to the HIV-1 antigens encoded by the vaccines that at least partially arrests or slows symptoms, or and/or complications of HIV infection. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

Nucleic acid vaccines are administered by methods well known in the art as described in Donnelly et al. (*Ann. Rev. Immunol.* 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), each of which is incorporated herein by reference. One skilled in the art would know that the choice of a pharmaceutically acceptable carrier, including a physiologically acceptable compound, depends, for example, on the route of administration of the expression vector.

As noted above, immunogenic DNA compositions can be delivered via a variety of routes. Typical delivery routes include parenteral administration, e.g., intradermal, intramuscular or subcutaneous routes. Administration of expression vectors of the invention to muscle and by electroporation can be a particularly effective method of administration, including intradermal and subcutaneous injections and transdermal administration. Transdermal administration, such as by iontophoresis, is also an effective method to deliver expression vectors of the invention to muscle. Epidermal administration of expression vectors of the invention can also be employed. Epidermal administration involves mechanically or chemically irritating the outermost layer of epidermis to stimulate an immune response to the irritant (Carson et al., U.S. Pat. No. 5,679,647).

Nucleic acids can be administered in solution (e.g., a phosphate-buffered saline solution) by injection, usually by an intravenous, subcutaneous or intramuscular route. In embodiments that employ a naked nucleic acid composition, the dose of a naked nucleic acid composition is from about 1.0 ng to about 10 mg for a typical 70 kilogram patient. Subcutaneous or intramuscular doses for naked nucleic acid (typically DNA) may range from 0.1 ug to 100 ug for a 70 kg patient in generally good health. For example, an HIV DNA vaccine, e.g., naked DNA or polynucleotide in an aqueous carrier, can be injected into tissue, e.g., intramuscularly or intradermally, in amounts of from 10 µl per site to about 1 ml per site. The concentration of polynucleotide in the formulation is usually from about 0.1 mg/ml to about 4 mg/ml. In some embodiments, the DNA may be administered in ng amounts, for example at a level of 1 to 100 ng.

In embodiments in which one or more of the components of a vaccine regimen is administered in the form of a protein, the protein is typically administered at a concentration that is determined by known techniques taking into account medical considerations regarding the subject. Dosages for administration of a polypeptide composition included milligram or microgram amounts per kilogram. Illustrative doses are about 0.1 ug/kg to about 500 mg/kg. For example, doses may range from about 1 ug/kg to about 100 ug/kg or from about 0.1 ug/kg to about 50 ug/kg. I some embodiments, the dosage is about 0.5 ug/kg or more, 1 ug/kg or more, 2 ug/kg or more, 5 ug/kg or more, 10 ug/kg or more 25 ug/kg or more or 50 ug/kg or more.

As understood by one in the art, dosages may vary depending on the route of administration.

The protein is formulated using well-known techniques for administration employing various routes, e.g., intravenous, subcutaneous, intramuscular, intranasal, transdermal, or intraperitoneal administration.

The vaccine may be delivered in a physiologically compatible solution such as sterile PBS. The vaccines may also be lyophilized prior to delivery. As well known to those in the art, the dose may be proportional to weight.

The compositions included in the regimen descried herein for inducing an immune response can be administered alone, or can be co-administered or sequentially administered with other immunological, antigenic, vaccine, or therapeutic compositions.

Compositions that may also be administered with the vaccines include other agents to potentiate or broaden the immune response, e.g., IL-15, IL-12, IL-2 or CD40 ligand, which can be administered at specified intervals of time, or continuously administered.

The vaccines can additionally be complexed with other components such as peptides, polypeptides and carbohydrates for delivery. For example, expression vectors, i.e., nucleic acid vectors that are not contained within a viral particle, can be complexed to particles or beads that can be administered to an individual, for example, using a vaccine gun.

The immunogenic compositions can also be formulated for administration via the nasal passages. Formulations suitable for nasal administration, wherein the carrier is a solid, include a coarse powder having a particle size, for example, in the range of about 10 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient. For further discussions of nasal administration of AIDS-related vaccines, references are made to the following patents, U.S. Pat. Nos. 5,846,978, 5,663,169, 5,578,597, 5,502,060, 5,476,874, 5,413,999, 5,308,854, 5,192,668, and 5,187,074.

The vaccines can be incorporated, if desired, into liposomes, microspheres or other polymer matrices (see, e.g., Felgner et al., U.S. Pat. No. 5,703,055; Gregoriadis, *Liposome Technology*, Vols. I to III (2nd ed. 1993). Liposomes, for example, which consist of phospholipids or other lipids, are nontoxic, physiologically acceptable and metabolizable carriers that are relatively simple to make and administer. Liposomes include emulsions, foams, micelles, insoluble monolayers, liquid crystals, phospholipid dispersions, lamellar layers and the like.

EXAMPLES ILLUSTRATING THE INVENTION

Example 1. Illustration of Enhanced Immune Responses Obtained with CE Construct Prime Followed by CE and Full-Length Polypeptides as Boost This example evaluated prime-boost combination vaccines to increase breadth of immunity. In addition to the CE prime-full length molecule boost, it was found that using a boost involving co-delivery of CE and full-length molecule resulted in significantly further improved breadth of the responses. This boost further elicited higher levels of cytotoxic T cells focusing the immune responses to the highly conserved epitopes.

Method: this study was performed using a simian immunodeficiency virus (SIV) derived conserved element pDNA vaccine that was designed from the SIV $p27^{gag}$ capsid protein by analogy to an HIV CE vaccine. The SIV $p27^{gag}$ is the proteolytic processing product derived from the full length SIV p57gag protein. Seven highly conserved elements were identified within the $p27^{gag}$ capsid protein by (i) analogy to HIV CE sequences and (ii) sequence conservation among available SIV sequences (FIG. 1). Two sets of sequences, p27CE1 and p27CE2, differing in six 'toggle' AA, were generated. DNA vectors expressing the SIV p27CE1 and p27CE2 proteins were tested in macaques.

Macaques (N=14) received vaccinations with a mixture of SIV p27CE1 pDNA and p27CE2 pDNA, referred to SIV p27 pDNA (FIG. 2). The CE-specific cellular immune responses were compared in blood. PBMC were stimulated with a SIV CE-specific peptide pool and showed the induction of robust CE-specific responses ranging from 0.03-0.8% of total T lymphocytes. The CE-specific T cells showed both central ($CD28^+$, $CD95^+$) and effector memory phenotype (EM, $CD28^-$, $CD95^+$) with a significant fraction of cytotoxic T cells (IFN-$\gamma^+$, granzyme $B^+$, $CD107a^+$). In contrast, only ~60% of the macaques (18 of 31 vaccinated animals) vaccinated with a plasmid expressing the full length SIV Gag developed responses recognizing any CE, albeit they developed robust cellular immune responses to variable regions of gag. These data are similar to results found in HIV gag DNA vaccinated animals (Kulkarni et al *PLoS One;* 9:e86254. 2014).

Figure 3:
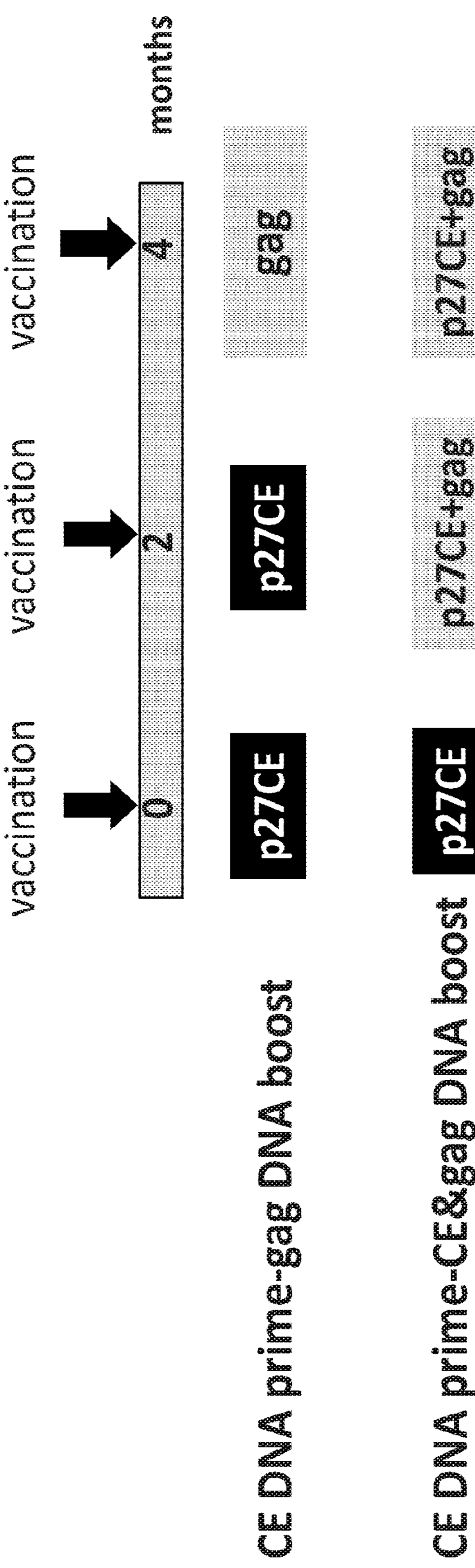
FIG. 3: Evaluation of two Prime-boost Regimens in Macaques. All animals received priming vaccination with conserved element (CE) DNA vaccine. The animals were boosted by DNA expressing the full-length gag DNA or by co-delivery of CE and gag DNA.

To further expand the potency of booster vaccination, two different regimens were compared using the SIV CE pDNA primed macaques (FIG. 3): (i) As prime, the animals (N=6) received p27CE pDNA vaccinations, and as boost (1×) gag DNA as described above (by analogy to HIV boosting regimen). (ii) Another group of animals (N=6) received a single p27CE pDNA vaccine as prime, and as boost co-delivery (2×) of CE and gag DNA. The CE-specific immune responses were measured in blood and the responses were mapped using peptide pools specific for each of the individual SIV CE.

Figure 4:
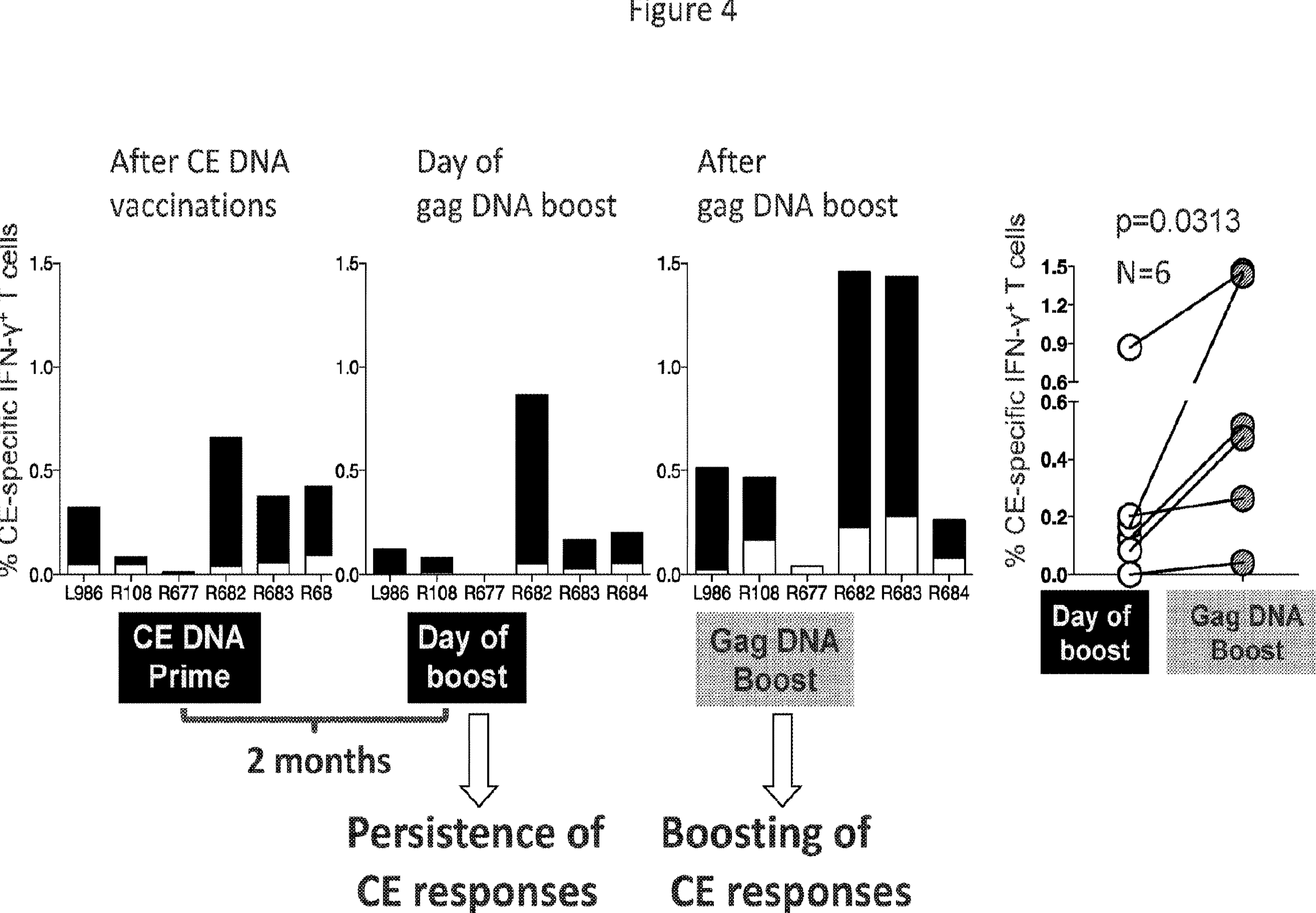
FIG. 4: CE DNA primed T cell Responses Are Boosted by a Single p57gag DNA Vaccination. After receiving the priming vaccination with p27CE pDNA, the animals received a heterologous booster vaccination with the full-length p57gag pDNA. The CE-specific T cell responses were measured by intracellular flow cytometry in blood at 2 weeks after the priming, 2 months later (day of booster vaccination) and 2 weeks later. PBMC were stimulated with a pool of peptides spanning the CE (15-mer overlapping by 11 AA and 10-mer overlapping by 9 AA). The increase of total CE-specific IFN-γ+ T cells upon boost is shown.

The SIV p27CE pDNA primed animals (N=6) received a booster vaccination with a plasmid expressing the full length SIV p57gag pDNA (FIG. 4). This resulted in a significant increase in CE-specific responses, corroborating the observation from the HIV p24CE prime-gag DNA boost studies. Thus, both the SIV p27CE pDNA and the HIV p24CE pDNA vaccine share the unique feature of effectively inducing immune responses to subdominant Gag epitopes, which is only inefficiently achieved by DNA vaccination expressing full length Gag. It was also demonstrated that for both CE vaccines, a gag pDNA boost significantly increased the magnitude of these responses.

The other group of CE primed macaques (N=6) received a booster vaccination by co-delivery of the CE DNA and a plasmid expressing the full length SIV p57gag pDNA (FIG. 5). Comparison of the magnitude of the immune responses obtained after the $1^{st}$ and $2^{nd}$ booster vaccination showed a significant increase (p=0.0022) of the magnitude of CE-specific T cell responses upon the 2nd boost (FIG. 5) reaching responses up to ~2% of total circulating T cells. These data show that the inclusion of two booster vaccinations is advantageous to increase the magnitude of the CE-specific responses.

Figure 6:
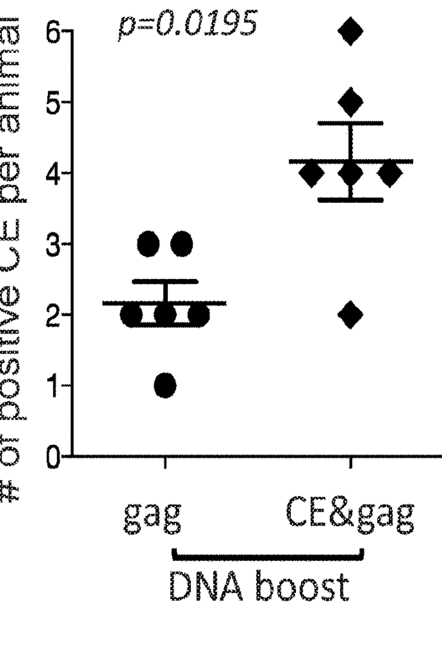
FIG. 6: CE DNA Prime and Co-delivery of CE&gag DNA as Boost Induces Broadest Responses. The total CE-specific responses was de-convoluted using peptide pools specific sub-pools (mixture of 15- and 10-mer peptides) to each individual CE using PBMC from animals vaccinated with CE DNA (N=14), animals that received a gag DNA boost (N=6) and animals that received co-delivery of CE and gag DNA as boost.

While both booster regimens led to marked increase in magnitude of the CE responses, reaching similar levels, a fundamental difference in the breadth of the responses was found (FIG. 6). Mapping of responses to individual CE in the CE-primed macaques (N-14) showed a response rate of 1-4 CE per animals (FIG. 6). Mapping the responses elicited by the gag DNA only boost revealed recognition of 1-3 CE per animal (FIG. 6). Thus, no change in breadth was found upon inclusion of additional gag DNA booster vaccination (both SIV and HIV model systems). In contrast, boosting of CE primed animals by co-delivery of CE and gag DNA resulted in increased breadth of the responses recognizing of 2-6 CE per animal with all 7 CE being immunogenic (FIG. 6). Comparison of the response rate (number of positive CE per animal) showed a significant (p=0.0195, Mann Whitney test) increase in breadth using co-delivery of CE and gag pDNA as boost.

The induced CE-specific immune responses were further examined for cytotoxicity markers (FIG. 7). Analysis of the CD4 and CD8 T cell subsets showed significant increase of CE-specific cells harboring granzyme B and being able to degranulate ($CD107a^+$) in the animals that received the CE and gag DNA co-delivery boost. The cytotoxic CE-specific responses within the total T cell population are plotted. Thus, SIV gag&CE DNA co-delivery as boosts not only broadened the Gag T cell responses, it also induced more robust cytotoxic CE-specific T cell responses.

The data obtained with the SIV p27CE DNA vaccine therefore demonstrate that a booster vaccination including the co-delivery of CE and gag pDNA provided a significant increase in breadth of the CE-specific responses compared to a regimen using only the gag pDNA boost. The co-delivery of CE pDNA and pDNA expressing the full length protein as boost is proposed to maximize the induction of T cell responses to subdominant HIV Gag epitopes and this strategy is currently tested.

Together, these data corroborate the original observation demonstrating that priming with CE as vaccine (DNA, viral vector, protein) is important to allow development of immune responses to subdominant epitopes. Fine-tuning the booster vaccination by including the co-delivery CE and the intact full-length molecule offers an additional advantage to optimize breadth and quality of the immune responses. This regimen is more effective than the CE DNA prime-gag DNA boost even when additional gag DNA boosts were given.

Figure 8A:
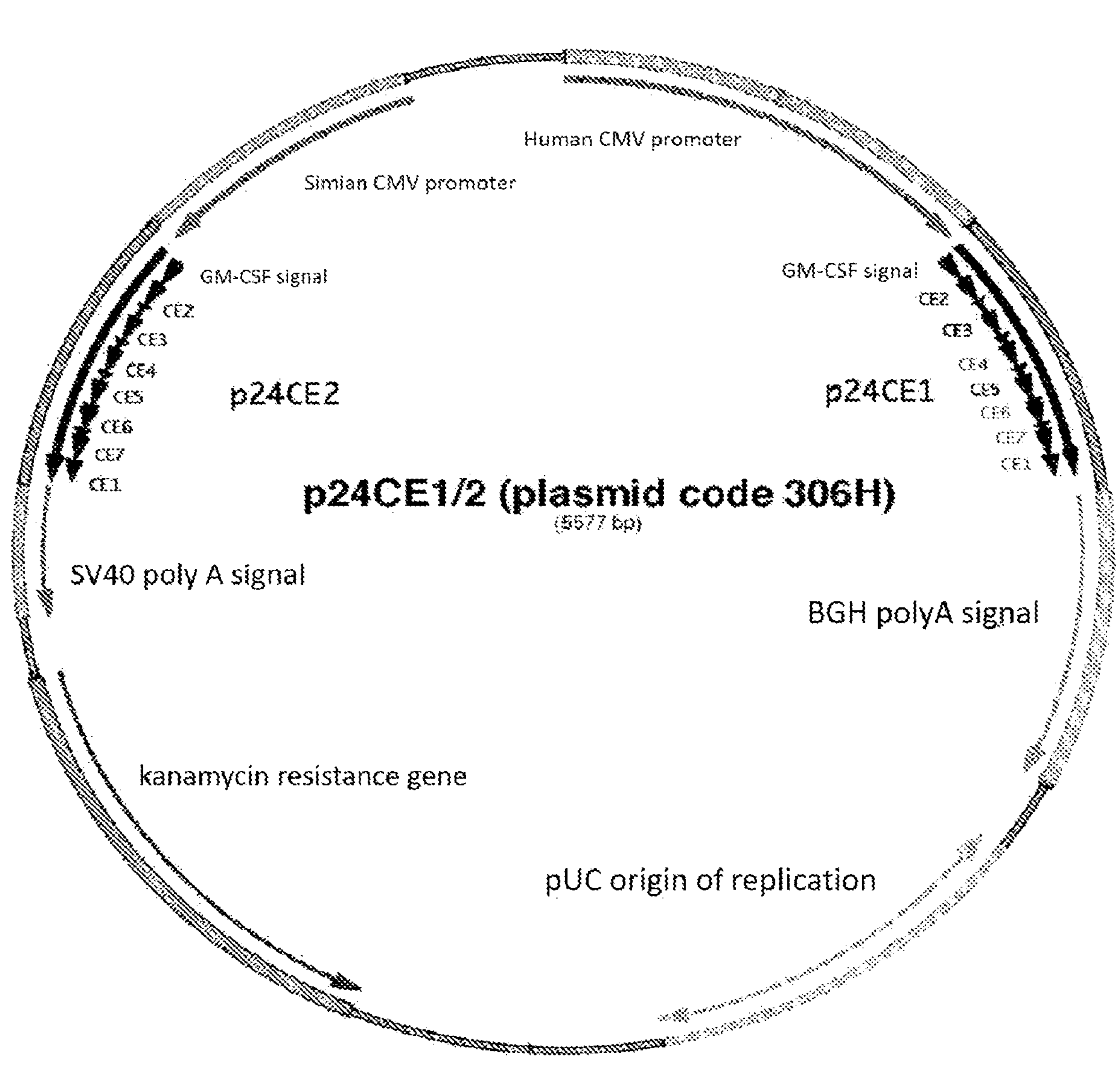
FIGS. 8A-8B: 8A. Schematic of p24GagCE plasmid. 8B. Schematic of p55gag plasmid.

In humans, immunogenic responses will be evaluated in a trial that includes priming with the HIV p24CE DNA (0, month 2), followed by 2 booster vaccinations using codelivery of p24CE DNA and p55gag DNA (Month 4 and 6). In macaques, there were no significant differences identified between 2 and 3 CE DNA vaccinations, thus, two priming vaccinations are planned to strengthen the priming step. Two booster vaccinations will be given because in the macaque model, 2 co-delivery boosts provided improved results. This trial employs ae dual-promoter p24CE1/2 pDNA (plasmid code 306H, FIG. 8A) that spans 5577 base pairs (bp) and encodes the two expression-optimized p24CE genes from a single eukaryotic expression vector pDP.CMVkan, a derivative of pVR1012 (Hartikka et al., 1996). The p24CE1 gene is expressed from the human cytomegalovirus (hCMV) promoter and is terminated by the bovine growth hormone (BGH) polyadenylation (polyA) signal. The p24CE2 gene is expressed from the simian CMV (sCMV) promoter and is terminated by the simian vaculating virus 40 (SV40) polyA signal. P24CE1 and p24CE2 proteins contain the 17-amino acid GM-CSF signal peptide (GenBank: AAA98768.1), which favorably affects localization and stability of p24CE1 and p24CE2 proteins as well as the nature of elicited immune responses (Kulkarni et al., 2013, supra). The sequences of both genes are optimized to enhance expression in human cells.

Figure 8B:
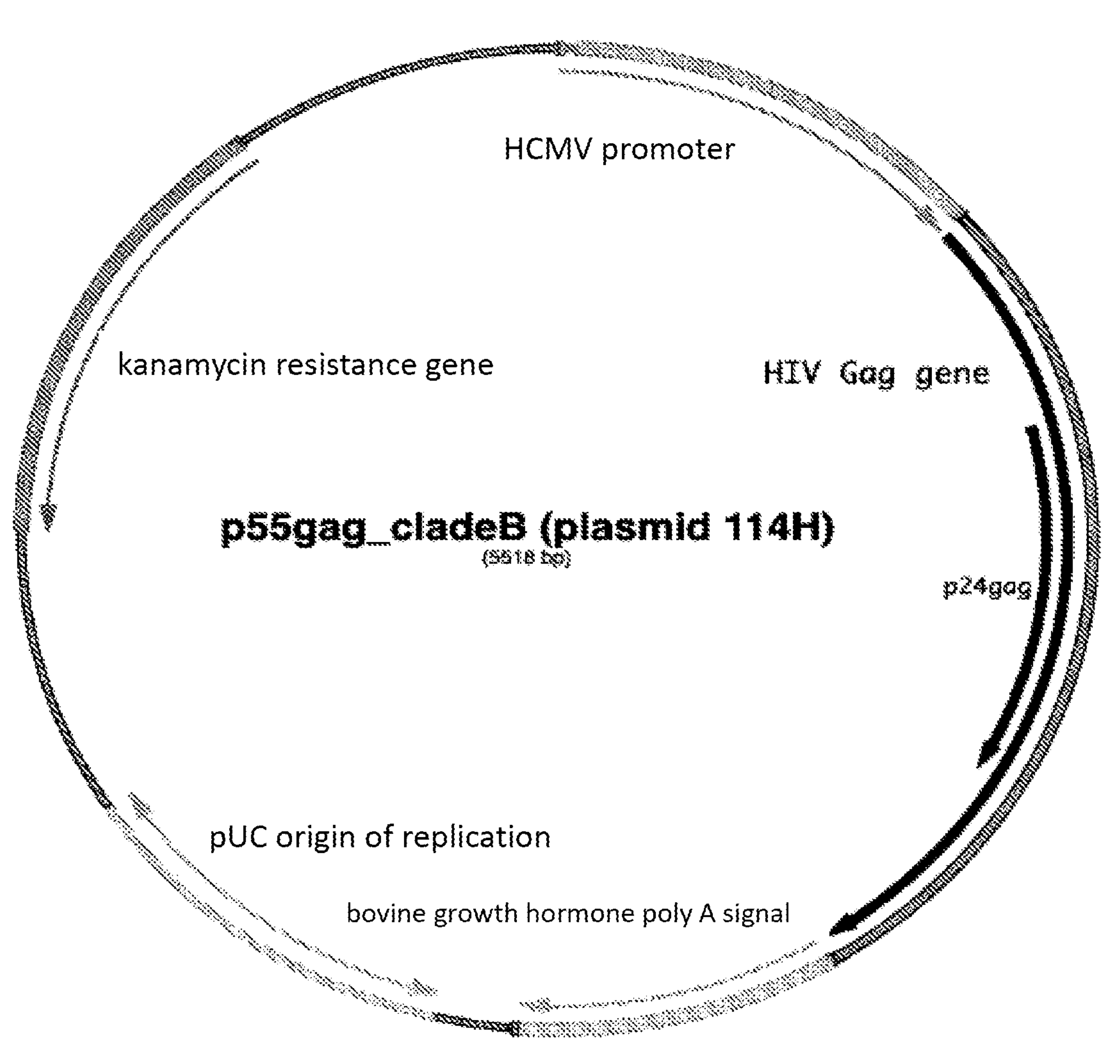

A plasmid encoding p55gag is used in the boost along with the p24CE plasmid. The p55gag pDNA (plasmid code 114H, FIG. 8B) spans 5518 bp and encodes the full-length p55gag protein of HIV-1 (clade B; GenBank NP_057850.1). The p55gag protein is 500 amino acids in length and contains the proteolytic processing product, p24gag, located between AA 133-363. The expression-optimized p55gag gene was chemically synthesized and inserted into the eukaryotic expression plasmid pCMVkan under the control of the hCMV immediate early enhancer/promoter and terminated by the BGH polyA signal. The pCMVkan plasmid backbone is derived from pVR1012 (Hartikka et al., 1996). pCMVkan shares the backbone with pDP.CMVkan, but lacks the simian CMV promoter and the SV40 polyadenylation signal.

Application of this method is not limited to HIV but can modulated to address the induction of immune responses to any subdominant epitopes (cellular and or humoral) to increase breadth, magnitude and quality of the immune responses.

Figure 9:
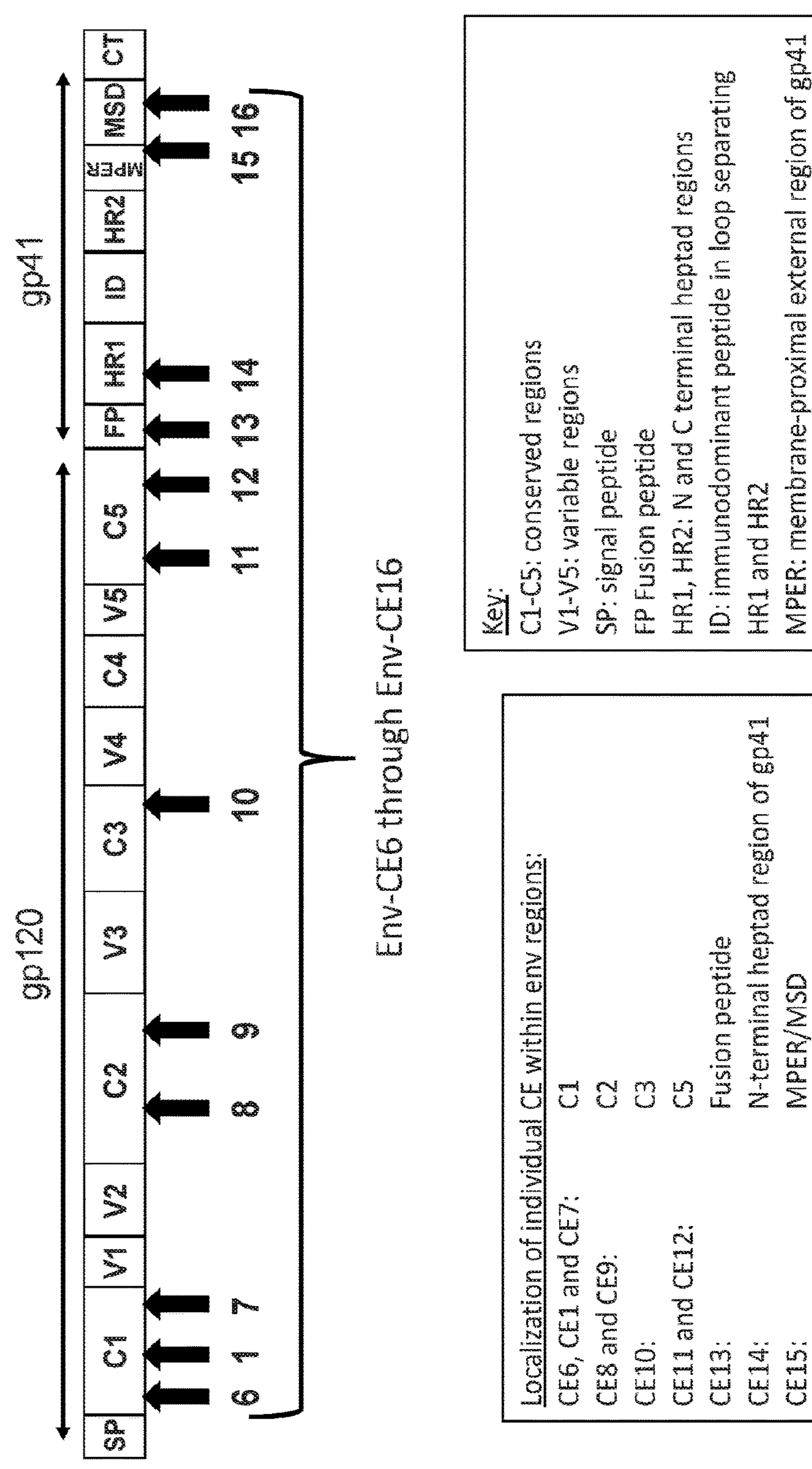
FIG. 9 provides a schematic of the localization of conserved regions within HIV Env and the distribution of conserved elements of the invention within the conserved regions.
Figure 10:
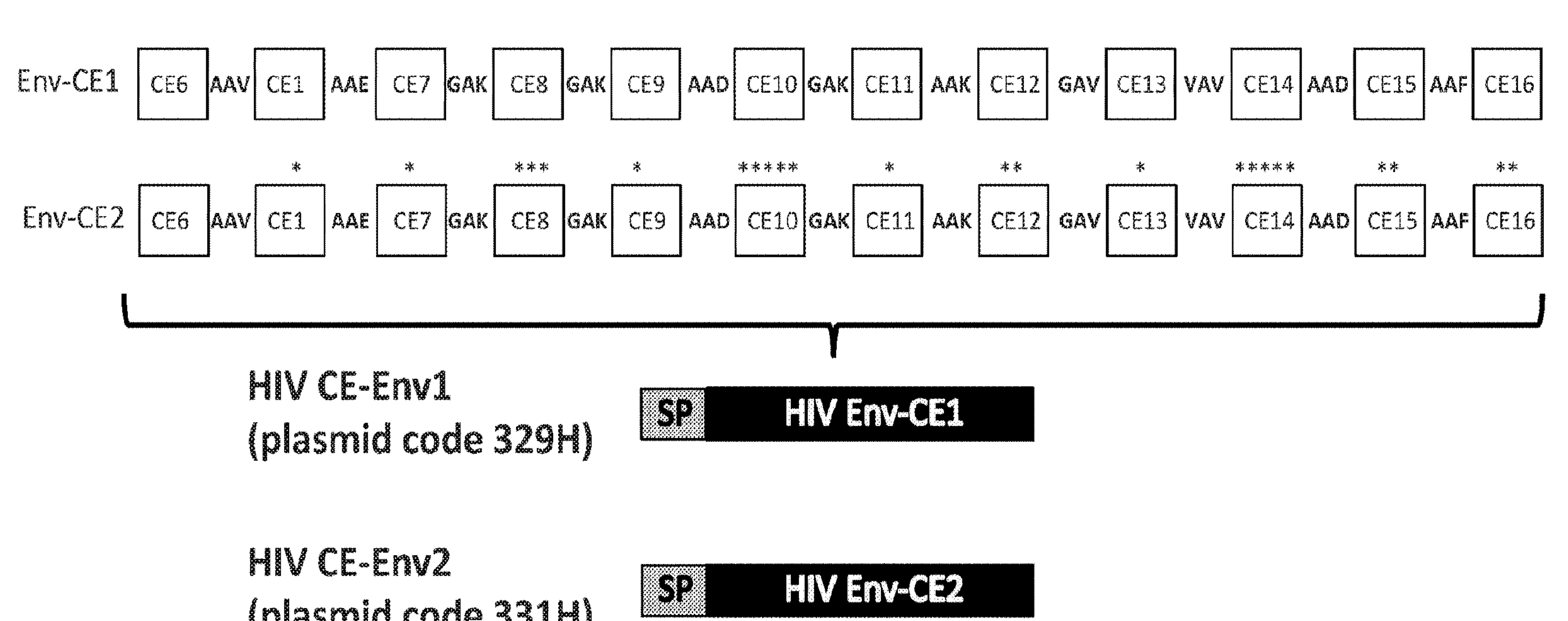
FIG. 10 depicts two Env CE Env immunogenic polypeptides, Env-CE1 and Env-CE2 in accordance with the invention. Env-CE1 and Env CE2 span 220 amino acids. They are highly related, differing by 24 amino acids. The Env-CE1 and Env-CE2 sequence are each 282 amino acids in length, including linkers that are each three amino acids in length and a 29-amino acid signal peptide.

Example 2. Env DNA Vaccination Induces Cross-Clade Specific Cellular Immune Responses in Mice Results Conserved Element DNA Vaccines A set of conserved elements (CE) was identified in the HIV Env protein (FIG. 9). This example describes the identification of 12 conserved elements in HIV Env of 11, 14, 21, 15, 23, 21, 13, 12, 14, 43, 20, and 13 AA in length (FIG. 10). Each CE segment is separated by linkers 3 amino acids in length, composed of alanine and some of which also contain a valine, glutamic acid, lysine, aspartic acid, phenylalanine or glycine, designed to facilitate processing of the protein. Expression-optimized synthetic Env-CE1 and Env-CE2 genes were inserted into an eukaryotic expression vector pCMVkan between the human CMV promoter and bovine growth hormone poly A signal. pCMVkan is optimized for optimal growth in bacteria (kanR) and expression of the insert in mammalian cells.

Regions for inclusion/exclusion from the vaccine were selected based on whether immune responses to such regions were associated with virologic control or lack of control. We designed and synthesized two versions of these synthetic proteins (Env-CE1 and Env-CE2), each of which is composed of 12 conserved elements that differ by 0-5 amino acid per conserved element (CE) to maximize the inclusion of commonly detected variants (See Table 1). These CE were collinearly arranged and separated by short amino acid linkers (e.g., 3 amino acids) designed to facilitate processing of the protein and avoidance of neo-antigens. The coding sequences were RNA/codon-optimized according to Pavlakis and Felber's RNA optimization method (U.S. Pat. Nos. 5,972,596; 5,965,726; 6,174,666; 6,291,664; 6,414,132; 6,794,498) and designed to use alternative codons to maximize expression in human cells. Expression-optimized sequences were placed into a eukaryotic DNA plasmid vector.

Figure 12:
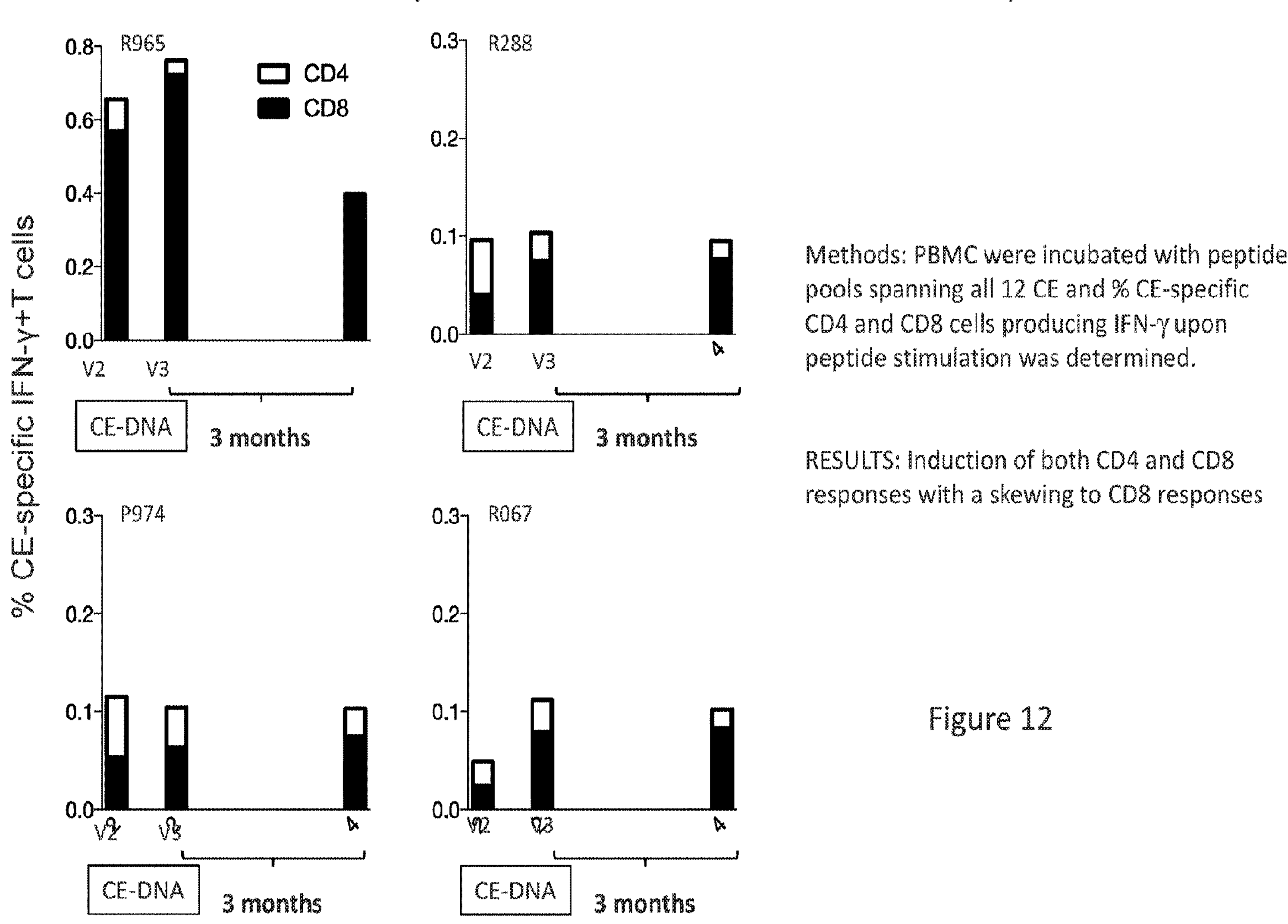
FIG. 12 provides illustrative data showing T cell responses of DNA-vaccinated macaques. Peripheral blood mononuclear cells (PBMCs) were incubated with a peptide pool spanning all 12 conserved elements. The percent of CE-specific CD4 and CD8 cells producing IFN-γ upon peptide stimulation was determined. The results show the induction of both CD4 and CD8 responses, with a skewing to CD8 responses.
Figure 13:
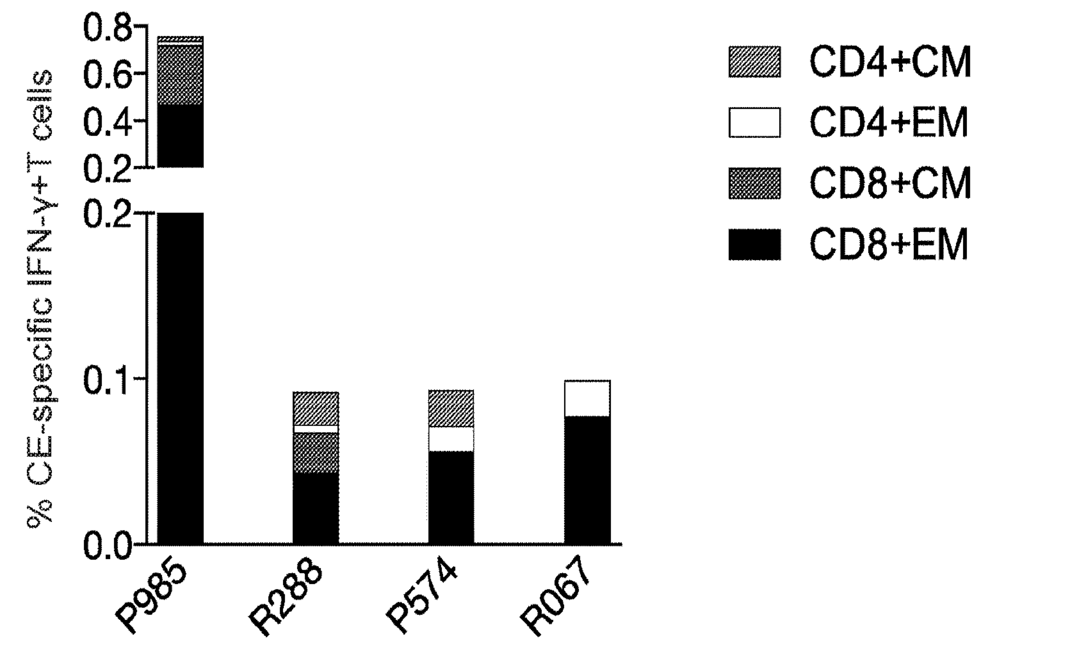
FIG. 13 provides data illustrative that vaccination with Env-CE vaccines induces memory T cell responses. PBMC were incubated with a peptide pool spanning all 12 conserved elements and the % CE-specific IFN-γ-producing CD4 and CD8 central memory (CM; $CD28^{+}CD95^{+}$) and effector memory (EM; $CD28^{-}CD95^{+}$) T cells was determined following peptide stimulation.
Figure 14:
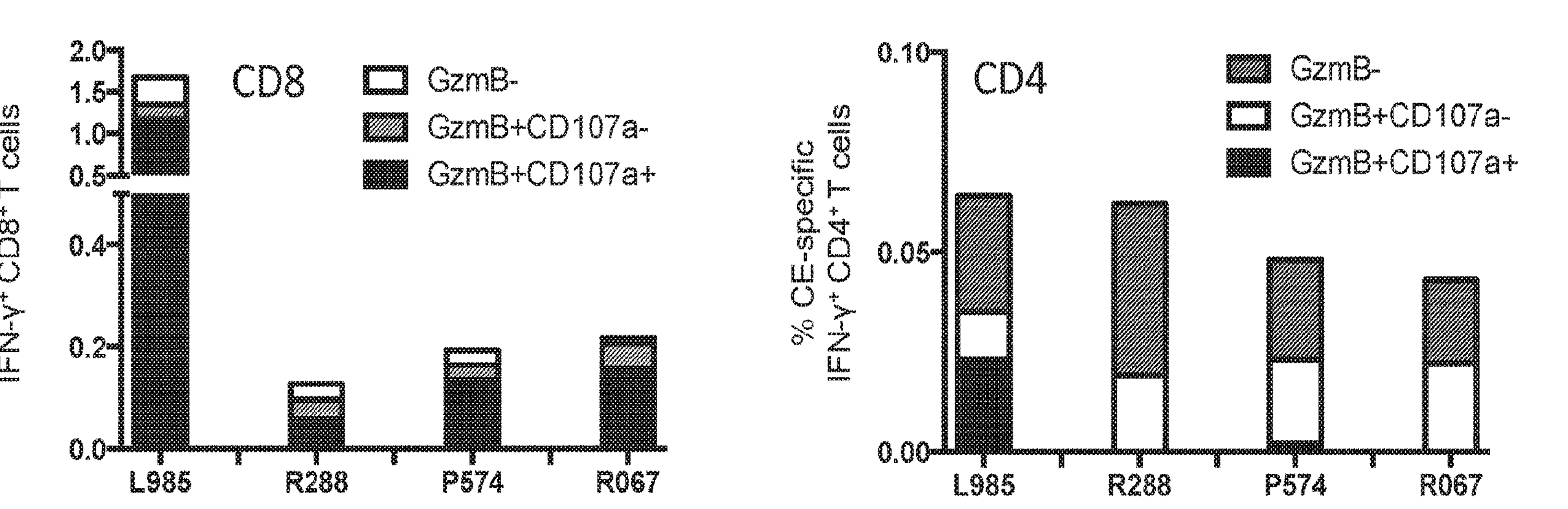
FIG. 14 provides data illustrating that Env-CE DNA vaccination induces CE-specific responses with a significant fraction of multifunctional $CD8^{+}$ T cells. PBMC were incubated with a peptide pool spanning all 12 CE and the % of IFN-γ-producing CE-specific CD4 and CD8 T cells harboring Granzyme B and expressing CD107a was determined following peptide stimulation.
Figure 20:
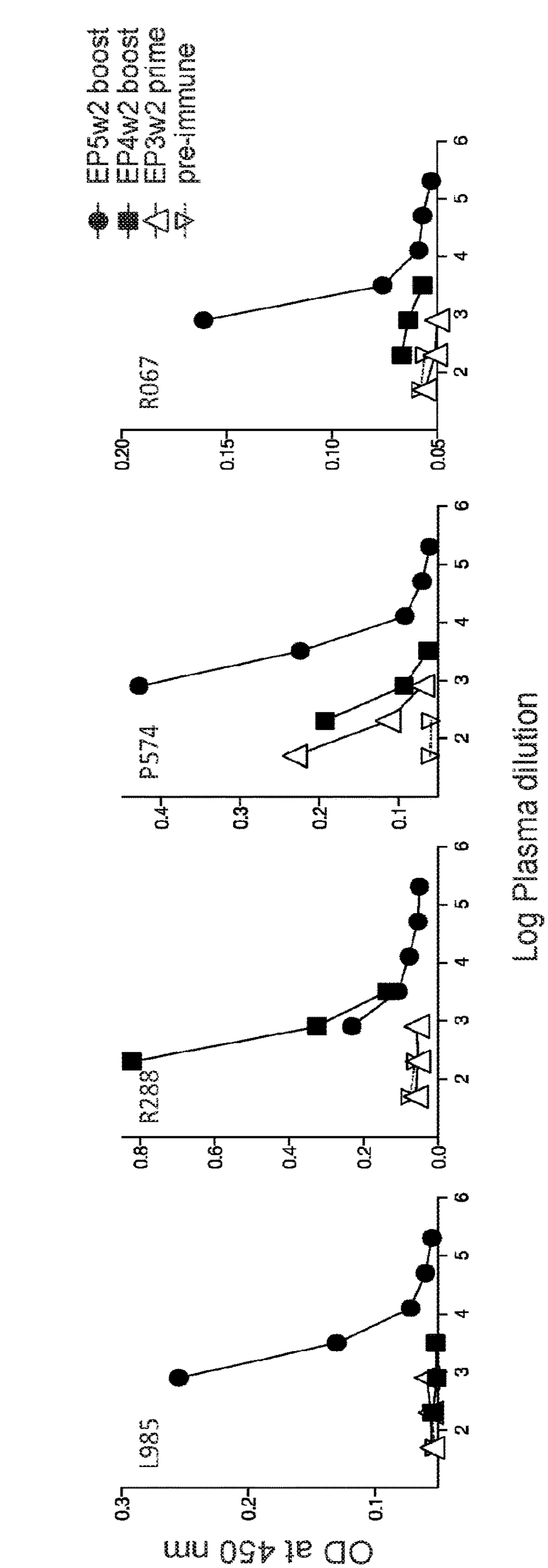
FIG. 20 shows data illustrating that an env-CE DNA vaccine induced antibodies that can recognize gp120 Env by ELISA (HIV-1 IIIB). In this experiment, serial dilutions of plasma from vaccinated animals were tested using an HIV-1 IIIB ELISA assay. The results show that one of the animals (P574) developed an antibody binding response to gp120 after CE prime vaccination (22 weeks after 3rd vaccination V3wk2). The responses were boosted by each of the full-length env DNA vaccination 4th and 5th vaccination (4th and 5th vaccination V4wk2, V5wk2). Animals L985, R288, and RO67 developed ELISA antibody responses only after booster vaccination ($4^{th}$ and $5^{th}$ vaccination).
Figure 21:
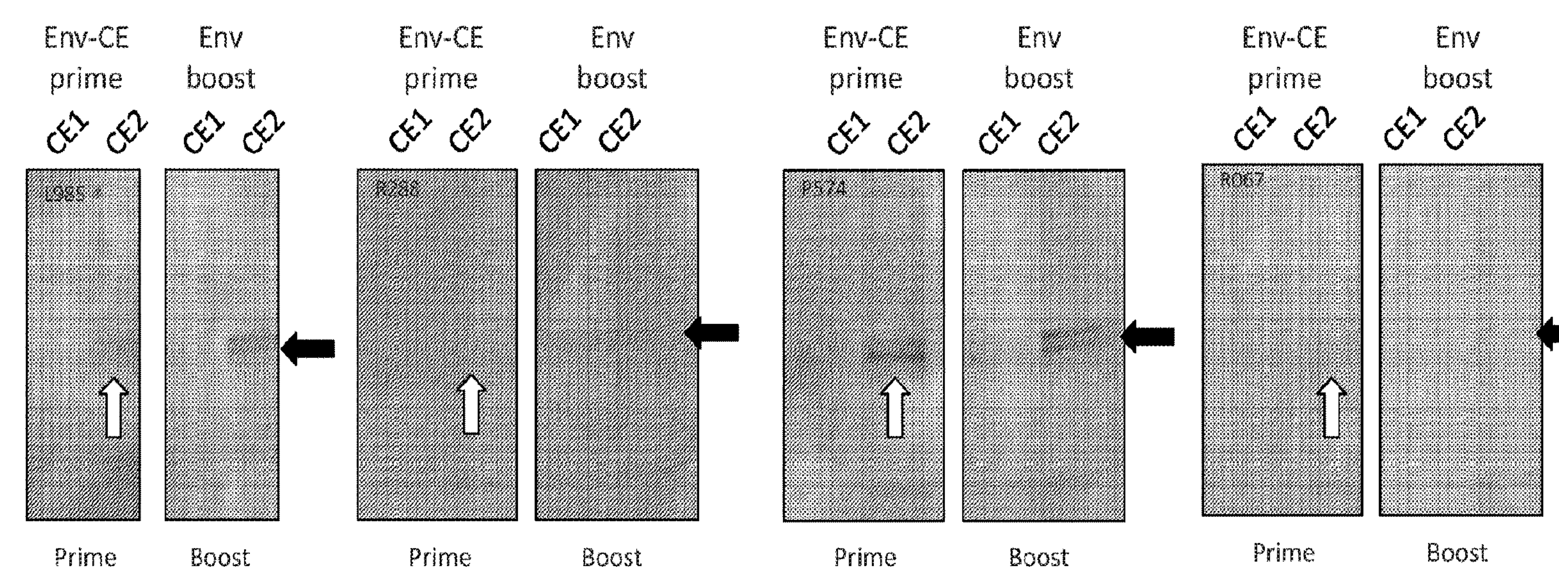
Figure 22:
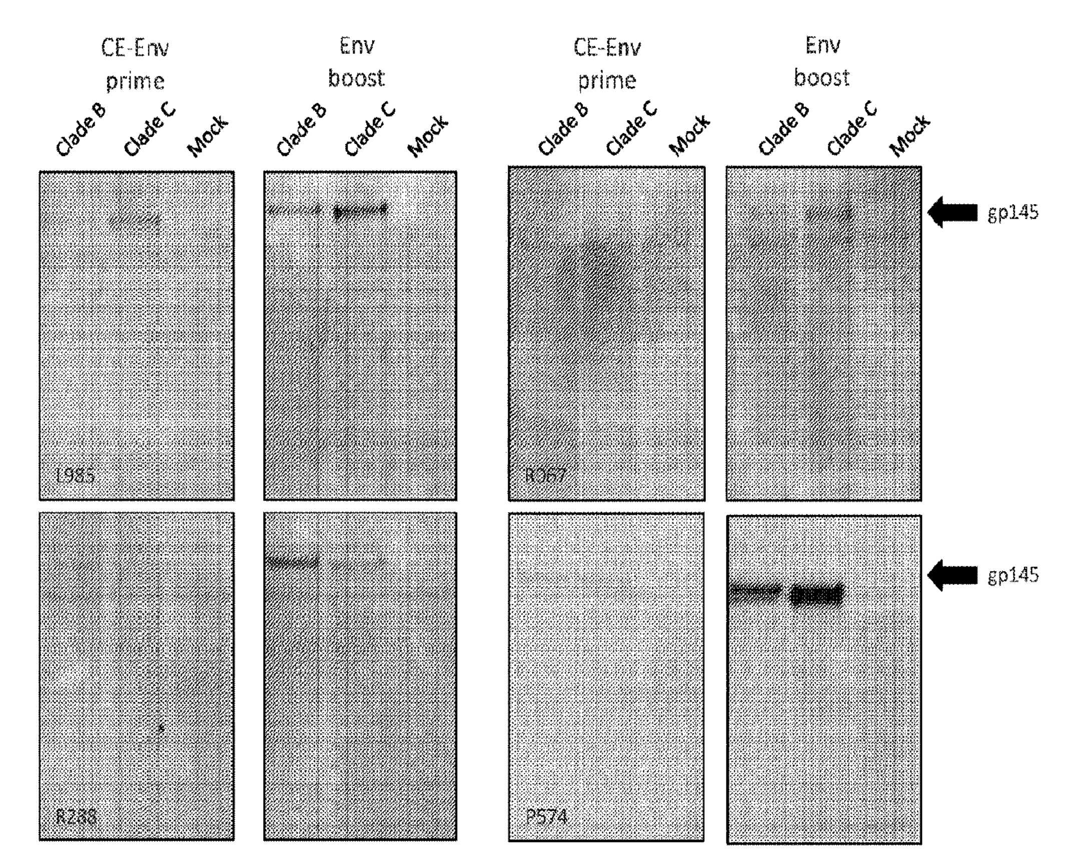
FIG. 22 provides data illustrating that antibodies induced by the HIV Env-CE vaccine recognized intact HIV Env proteins from both clade B and clade C. gp145 protein from transfected cells was separated on denaturing gels and transferred onto membranes. The membranes were incubated with plasma from macaques primed using env-CE DNA and boosted with intact env DNA. Proteins from mock-transfected cells served as a negative control.

In an illustrative embodiment, a combination of the two plasmids was used to vaccinate 4 macaques (FIG. 11). This study showed induction of robust cellular CE-specific immune responses (0.1-0.8% of T cells), mediated primarily by CD8+ T cells. (FIG. 12). Fine mapping showed that 6 of the 12 CE were immunogenic (FIG. 15). The vaccine induced both CD8 and CD4 memory T cell responses of the central and effector type (FIG. 13). This vaccine also induced CE-specific responses with a significant fraction of CD8+ T cells with cytotoxic phenotype (Granzyme B+ and CD107a+) (FIG. 14). Thus, the Env-CE DNA vaccine induced cellular immune responses with the desired features for an effective T cell vaccine. In addition to the cellular immunity, the Env-CE DNA vaccine also induced humoral immune responses. The antibodies could detect the immunogen as well as clade B and clade C Env by Western blotting (FIG. 22). The antibody could also detect HIV gp120 by ELISA (FIG. 20).

Figure 16:
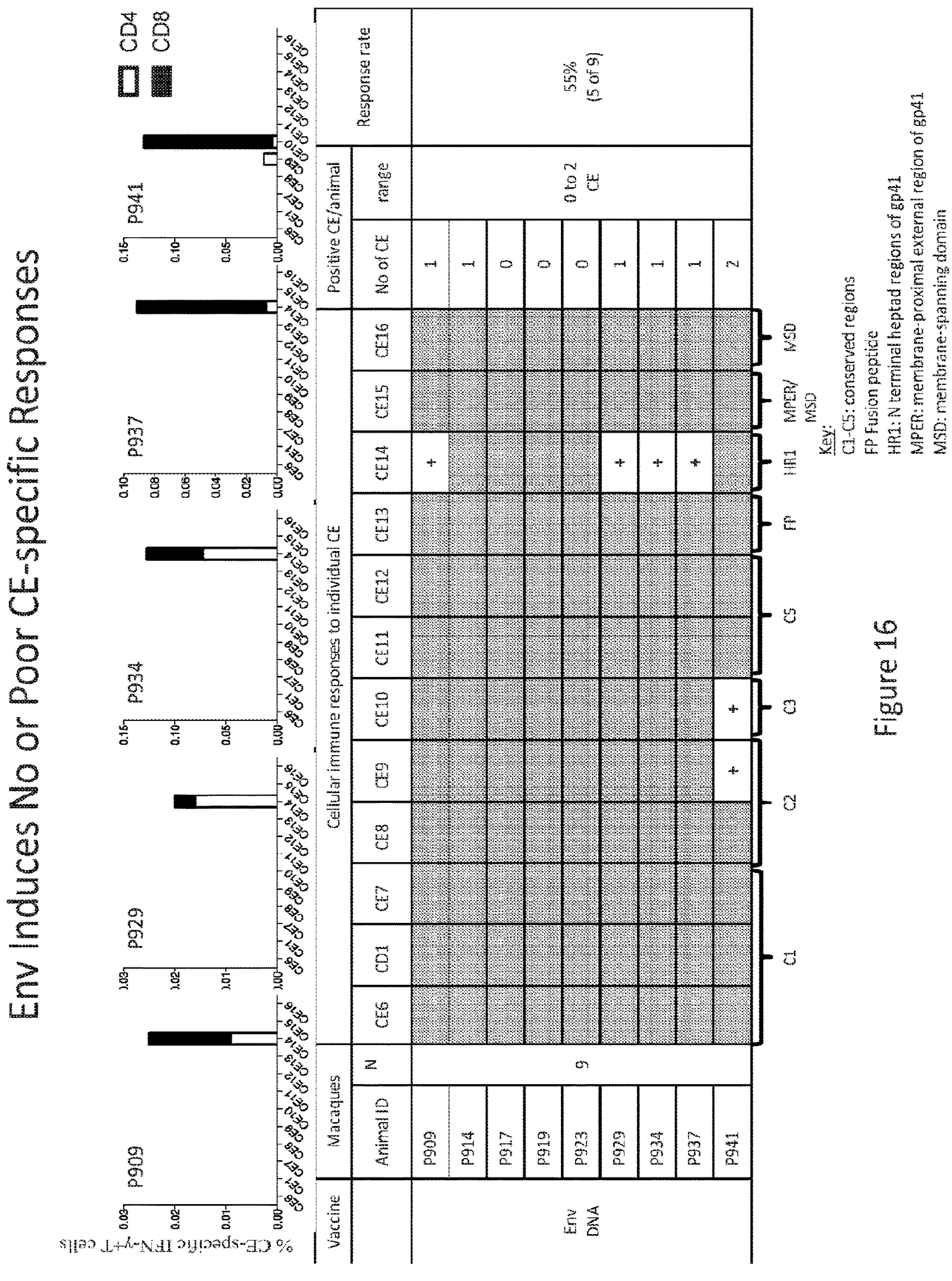
FIG. 16 provides data illustrating that vaccination of 9 macaques with DNA-expressing full-length Env induces no, or poor, CE-specific responses. Env-specific responses were observed in all animals (using a peptide pool of HIV Env clade B strain BaL spanning gp120) and CE-specific responses are found in about 55% of vaccinees. The CE-specific responses exhibited narrow breadth (0-2 CE/animal) compared to the HIV Env-CE vaccine (2-4CE/animal; 100% response rate).

In contrast, vaccination of macaques (N=9) with complete Env DNA failed to develop CE-specific linear peptide responses in 50% of the macaques or induced poor responses to only 1 or 2 CE (FIG. 16) and could not detect the immunogen on Western blots. This indicates that the 12 Env CE are not immunogenic when present within with the complete Env protein, likely due to immunological interference with other epitopes and thus, unable to induce de novo responses.

Figure 17:
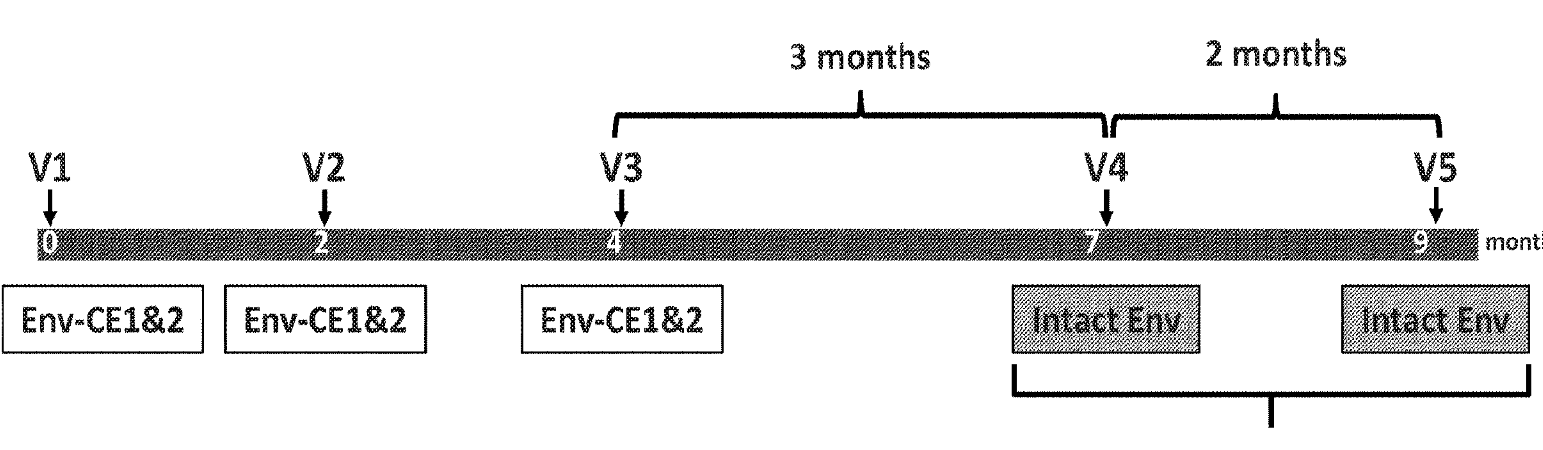
FIG. 17 illustrates a prime boost vaccination protocol using HIV env-CE DNA as prime and env DNA as boost. The boost was a mixture of env DNA composed of clade B Bal and 6101 and clade C 1086 env DNA covering all of the 24 CE sequences present in HIV Env CE1 and CE2 proteins. The intact Env molecule produced (gp145) lacks the immunodominant loop in the extracellular portion of gp41. Macaque IL-12 DNA was included in the vaccine mixture. DNA was delivered by intramuscular injection followed by in vivo electroporation.
Figure 18:
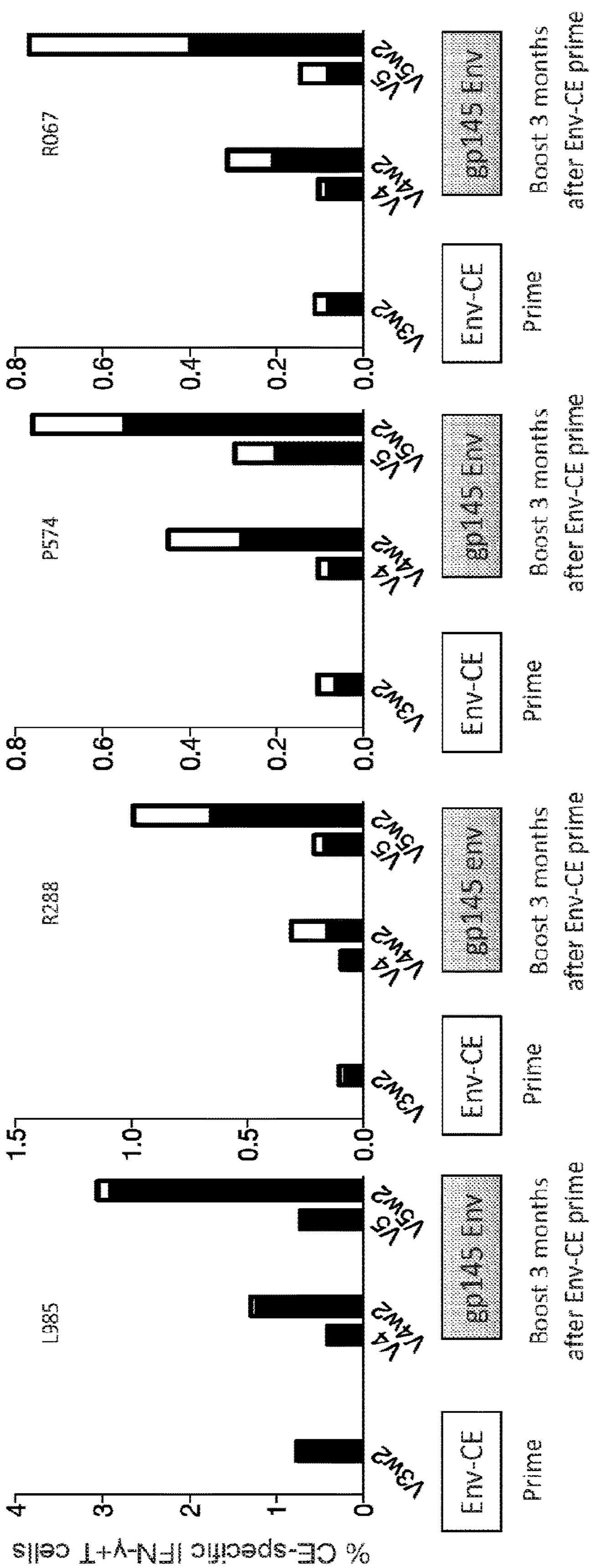
FIG. 18 provides data illustrating that env-CE DNA (CE1 and CE2) primed responses are boosted upon vaccination with intact Env. The results show that CE-specific responses were significantly increased upon a first boost with gp145 env DNA and were further augmented with a $2^{nd}$ boost. In contrast, env DNA vaccination only induced poor, or no, CE-specific responses. Priming with env-CE DNA followed by boosting with DNA encoding intact Env is an effective regimen to increase the breadth and magnitude of Env-specific responses, including memory and cytotoxic T cell responses.

Implementation of a prime-boost regimen using the Env-CE DNA prime followed by the intact Env boost (FIGS. 17, 18, and 19), demonstrated great increase of both cellular (including cytotoxic) responses as well as humoral responses. In particular, we found a great augmentation of linear peptide response to the CE, which is not found in Env DNA vaccinated macaques. Although inefficient in generating de novo responses to the CE, boosting with the intact Env DNA potently augmented pre-existing immunity. This vaccine regimen thus achieved an effective alteration in the immunological hierarchy.

These data thus indicate that HIV Env-CE1 and Env-CE2 are effective immunogens in inducing cellular and humoural responses and fulfill the basic criteria of inducing responses to highly conserved region of Env that are not seen by the immune system as part of the intact Env (altered immuno-hierachy) and the responses are cross-clade reactive (improved cross-clade breadth).

As shown in the illustrative data provided herein, the use of full-length Env fails or only poorly induces responses to the conserved regions of the protein. This led to the hypothesis that CE epitopes within the Env protein are not immunogenic due to either suboptimal processing and presentation or immunodominance hierarchy focusing the responses to variable epitopes. To address this experimentally, Env-CE DNA primed macaques received an Env DNA booster vaccine with the expectation of either no boost of CE responses (if no processing and presentation of CE-containing peptides from Env) or a boost of the CE responses (if immunodominance hierarchy can be altered by CE priming). Indeed, robust increase in immunity was found in CE-primed macaques given a boost with DNA expressing intact Env.

Therefore, priming with Env-CE DNA and boosting with plasmid expressing intact Env may solve a major obstacle in HIV vaccine development, demonstrating alteration of the hierarchy of epitope recognition and development of immune responses to potentially protective subdominant highly conserved epitopes. Boosting with Env DNA vaccine increases magnitude, breadth and polyfunctionality of the cellular responses as well as the breadth of humoral immunity against Env, targeting epitopes within the highly conserved elements as well as outside Env-CE.

Identification of Conserved Element Regions

The success of a conserved elements vaccine approach (1) depends on the ability to identify important features of viral proteins. Recent studies have shown that mutations at highly conserved sites showed varying degrees of fitness impact, from deleterious to negligible (2-5) to increasing (6).

Furthermore, mutations at sites that remain conserved through time have been shown to have greater fitness cost than mutations of amino acids that became dominant (and hence calculated to be conserved) later in the pandemic (2). Indeed, HIV strains are continuously being imprinted by the human HLA types encountered in different human populations (7,8). Thus, sequence conservation may change as the virus continues to evolve and adapt to host immunity, and contemporary sequence conservation may not be sufficient for pinpointing sites with crucial functional or structural roles. We therefore use sequence conservation as well as other features to identify the conserved elements to be used in our vaccines. The degree of conservation required for inclusion as an Env CE was at least 90% across the entire HIV-1 M group, and usually at least 98%. However, this requirement could be relaxed if data was available in the literature that associated a CTL or antibody epitope, within the CE, with virologic control (as evidenced by low viral load). If an epitope was associated with lack of virologic control (high viral load), its sequence was excluded from inclusion in a CE. Criteria for assigning virologic control or lack of control vary in the literature. For example, Mothe (9) and Matthews (10) used viral load <2,000 HIV RNA molecules per milliliter of blood plasma to indicate control.

Toggle sites were used to create two versions of most CE. A toggle site represents an amino acid site at which conservation may be low but at which two amino acids combined account for the vast majority of sequences of all HIV-1 M group sequences known, usually 98-100%. HIV-1 M group subtypes B, primarily found in the Americas and Western Europe, and subtype C primarily found in South Africa and India, represent most of the available sequence data, and together they represent >60% of all HIV-1 infections. Toggle sites often represent AA that are highly conserved in either subtype B or C, and the CE1 and CE2 sequences correspond to the AA most associated with subtypes B and C, respectively, if the consensus or second most common variant residues differed. Another means of coordinating toggle sites is to associate covarying amino acids (11, 12).

Other features that resulted in a relaxation of the 90% requirement was an association with known function or CTL escape resulting in a loss in viral fitness, or to substantially extend the length of a CE. For example, the CD4 binding loop region of the HIV Env protein corresponds to a region that binds to broadly neutralizing antibodies and this region is included as CE10 and CE19. To include this region, seven toggle sites in were employed and one residue was included in CE10 without a toggle that had a conservation level of only 79%. In another example, a very long CE (CE14; 43 AA) was included by allowing five toggle sites and one residue was conserved only at a level of 84% across the HIV-1 M group. However, this site was conserved at 97% and 99% in HIV-1 M group subtypes B and C and no obvious toggle site was evident. Alternate CE were generated in some cases by relaxing the criteria further to extend a first generation CE in an attempt to increase its immunogenicity.

Next, we tested the ability of structure-based computational models to assign sites of mutations that would destabilize the protein structure as a means of identifying vulnerable targets for inclusion in CE vaccines. This approach was first applied to the HIV capsid protein for which more comprehensive three-dimensional structural data is available. Predicted destabilizing mutations were rarely found in a database of 5811 HIV-1 capsid protein coding sequences, with none being present at a frequency greater than 2%. However, 90% of variants with high instability scores from a set of 184 capsid variants whose replication fitness or infectivity has been studied in vitro had aberrant capsid structures and reduced viral infectivity. Based on these instability scores, we identified 45 sites in the capsid protein prone to destabilizing mutations. Applying this method to capsid protein sequences, 9 additional sites were included in a second generation of CE. More than half of these sites are targets of one or more known inhibitors of capsid function (Table 3). The capsid regions enriched with these sites also overlap with peptides shown to induce cellular immune responses associated with lower viral loads in infected individuals.

A joint scoring metric was also developed that takes into account both sequence conservation and protein structure stability. This performed better at identifying deleterious mutations than sequence conservation or structure stability information alone (Table 2). The computational sequence-structure stability approach thus provides an additional method of identifying conserved elements suitable for use in an immunogenic composition employing conserved elements as described herein for HIV polypeptides. Twenty-one sites in Env were also identified as prone to destabilizing mutations, 11 of which are included in HIV CE.

A joint scoring metric was also developed that takes into account both sequence conservation and protein structure stability. This performed better at identifying deleterious mutations than sequence conservation or structure stability information alone (Table 2). The computational sequence-structure stability approach provides an additional method of identifying conserved elements suitable for use in an immunogenic composition employing conserved elements as described herein for HIV polypeptides.

Detailed Methods for Structural Stability Prediction.

Starting 3-dimensional structures. The capsid hexamer, PDB ID 3H4E (13), and the dimer form of the carboxy-terminal domain of the capsid, PDB ID 1A43 (14), were used as template structures for mutations in the amino-terminal domain (NTD; residue 1 to 147) and the carboxy-terminal domain (CTD; residue 148 to 219, including the linker region), respectively. While the known capsid hexamer structure also includes CTD, it does not contain the CTD dimerization interface, shown to be crucial for mature capsid structure and function (15-17). Hence, the CTD dimer (14) was also used. The last 13 residues were missing from the C-terminus of the template structures and, hence, excluded from analysis.

A high-resolution crystal structure of a trimeric pre-fusion Env with the antibodies removed was used as template. As no high-resolution structure of the HIV-1 Env protein with all of the variable loop sequences identified has yet been elucidated, these predictions may not cover all mutations that affect protein function.

In silico mutagenesis. All 19 possible amino acid changes were introduced in silico at each position in the HIV-1 capsid and Env proteins, one at a time. Reference structures in which the starting amino acid was re-introduced into the structure were also generated and used as a control set.

Two in silico mutation modeling approaches were applied: Fixed-backbone models explore the best-fit side-chain conformation while the main chain atoms of the mutated residue are kept unchanged from the original position in the template structure. The side-chain atoms of the mutated residue were replaced with those of the new amino acid. The best-fit side chain conformation was selected using the SCWRL program version 4.0 (18). The model was then run through 200 steps of energy minimization to remove atomic clashes or internal constraints generated by side-chain replacement using the CHARMM force field, as implemented in the program NAMD version 2.8 (19). Flexible-backbone models allow the main chain atoms to move along with the side chains and the best-fit combination is selected. These were generated in the FOLDX program suite (20) using the BUILDMODEL function with default parameters. This method allows the neighboring side-chains to be moved in order to explore alternative backbone conformations.

Proteins stability scores. Two types of protein-scoring functions were used to assess mutant models: The atomic distance-dependent statistical based scoring function referred to as Discrete Optimized Protein Energy (DOPE) (21) and the empirical based force field energy function called FOLD-X energy function (FOLDEF) (22). DOPE is part of the protein-modeling package MODELLER (23). FOLDEF is part of the FOLDX program suite (20). Both programs were run using default parameters.

Sequence dataset and amino acid database frequencies. Full-length HIV-1 subtype B Gag and Env coding sequences were downloaded from the HIV database. Any sequences with hypermutations (24) early stop codons, frame-shift mutations or ambiguous amino acids were excluded. A multiple sequence alignment was prepared using MUSCLE (25) and then manually edited using Mesquite (26). The database frequency of each amino acid at each site in the final alignment was then calculated using a perl script.

To identify candidate regions for CTL vaccine immunogens design, we searched the Env and capsid sequences in sliding windows of 15 amino acids, one amino acid at a time, and counted the number of sites prone to destabilizing mutations within each window. The window of size 15 was selected to cover the length of known CD4 and CD8 epitopes (27). If less than 70% of the possible AA substitutions were predicted to result in a stable structure, then the site was considered to be structurally vulnerable. As possible, given our other criteria, structurally vulnerable sites were included in CE.

Composite sequence-structure stability score. A composite score was derived from the mutation database frequency and FOLDEF score of the mutant flexible backbone model. First, all mutations were ranked by database frequency in ascending order. Mutations with the lowest database frequency, i.e., 0%, were given the lowest frequency rank. Next, all mutations were ranked by FOLDEF score in descending order, i.e., mutant models with the highest stability score were given the lowest stability rank. For each mutation, the two ranks were added to get a composite score.

The combined sequence-structure approach described here has the potential to serve as a target-screening tool for HIV drug and vaccine development. One limitation of this work is that only single amino acid changes were studied, whereas compensatory mutations can arise during viral infection that can restore protein stability and function (Chang, 2011; Gong, 2013; Liu, 2014). Also, all sequence, structure and experimental data used in our analyses were obtained using HIV-1 subtype B viruses. Studies of the effect of more complicated mutational patterns on protein stability in multiple genetic background will provide further insight for identifying desirable targets for HIV vaccines and therapies. Lastly, amino acid conservation can also be evaluated by weighting specific amino acid substitutions by the similarity in physico-chemical properties to the initial amino acid.

REFERENCES CITED IN EXAMPLES SECTION BY NUMBER

1 Rolland, M., Nickle, D. C., and Mullins, J. I., Hiv-1 Group M Conserved Elements Vaccine, PLoS Pathogens 3 (11), e157 (2007)

2 Rolland, M., Manocheewa, S., Swain, J. V., Lanxon-Cookson, E. C., Kim, M., Westfall, D. H., Larsen, B. B., Gilbert, P. B., and Mullins, J. I., Hiv-1 Conserved-Element Vaccines: Relationship between Sequence Conservation and Replicative Capacity, J Virol 87 (10), 5461-7 (2013) PMC3648173

3 Manocheewa, S., Swain, J. V., Lanxon-Cookson, E., Rolland, M., and Mullins, J. I., Fitness Costs of Mutations at the Hiv-1 Capsid Hexamerization Interface, PLoS One 8 (6), e66065 (2013) PMC3681919

4 Rihn, S. J., Wilson, S. J., Loman, N. J., Alim, M., Bakker, S. E., Bhella, D., Gifford, R. J., Rixon, F. J., and Bieniasz, P. D., Extreme Genetic Fragility of the Hiv-1 Capsid, PLoS Pathog 9 (6), e1003461 (2013)

5 Tieu, H.-V., Rolland, M., Hammer, S. M., and Sobieszczyk, M. E., Translational Research Insights from Completed Hiv Vaccine Efficacy Trials, J Acquir Immune Defic Syndr 63, S150-S4 (2013)

6 Troyer, R. M., Mcnevin, J., Liu, Y., Zhang, S. C., Krizan, R. W., Abraha, A., Tebit, D. M., Zhao, H., Avila, S., Lobritz, M. A., Mcelrath, M. J., Le Gall, S., Mullins, J. I., and Arts, E. J., Variable Fitness Impact of Hiv-1 Escape Mutations to Cytotoxic T Lymphocyte (Ctl) Response, PLoS Pathog 5 (4), e1000365 (2009) PMC2659432

7 Kawashima, Y., Pfafferott, K., Frater, J., Matthews, P., Payne, R., Addo, M., Gatanaga, H., Fujiwara, M., Hachiya, A., Koizumi, H., Kuse, N., Oka, S., Duda, A., Prendergast, A., Crawford, H., Leslie, A., Brumme, Z., Brumme, C., Allen, T., Brander, C., Kaslow, R., Tang, J., Hunter, E., Allen, S., Mulenga, J., Branch, S., Roach, T., John, M., Mallal, S., Ogwu, A., Shapiro, R., Prado, J. G., Fidler, S., Weber, J., Pybus, O. G., Klenerman, P., Ndung'u, T., Phillips, R., Heckerman, D., Harrigan, P. R., Walker, B. D., Takiguchi, M., and Goulder, P., Adaptation of Hiv-1 to Human Leukocyte Antigen Class I, Nature 458 (7238), 641-5 (2009) PMC3148020

8 Rousseau, C. M., Lockhart, D. W., Listgarten, J., Maley, S. N., Kadie, C., Learn, G. H., Nickle, D. C., Heckerman, D. E., Deng, W., Brander, C., Ndung'u, T., Coovadia, H., Goulder, P. J., Korber, B. T., Walker, B. D., and Mullins, J. I., Rare Hla Drive Additional Hiv Evolution Compared to More Frequent Alleles, AIDS Res Hum Retroviruses 25 (3), 297-303 (2009) PMC2693345

9 Mothe, B., Llano, A., Ibarrondo, J., Zamarreno, J., Schiaulini, M., Miranda, C., Ruiz-Riol, M., Berger, C. T., Herrero, M. J., Palou, E., Plana, M., Rolland, M., Khatri, A., Heckerman, D., Pereyra, F., Walker, B. D., Weiner, D., Paredes, R., Clotet, B., Felber, B. K., Pavlakis, G. N., Mullins, J. I., and Brander, C., Ctl Responses of High Functional Avidity and Broad Variant Cross-Reactivity Are Associated with Hiv Control, PLoS ONE 7 (1), e29717 (2012) PMC3251596

10 Matthews, P. C., Listgarten, J., Carlson, J. M., Payne, R., Huang, K. H., Frater, J., Goedhals, D., Steyn, D., Van Vuuren, C., Paioni, P., Jooste, P., Ogwu, A., Shapiro, R., Mncube, Z., Ndung'u, T., Walker, B. D., Heckerman, D., and Goulder, P. J., Co-Operative Additive Effects between Hla Alleles in Control of Hiv-1, PLoS One 7 (10), e47799 (2012) PMC3477121

11 Carlson, J. M., Brumme, Z. L., Rousseau, C. M., Brumme, C. J., Matthews, P., Kadie, C., Mullins, J. I., Walker, B. D., Harrigan, P. R., Goulder, P. J., and Heckerman, D., Phylogenetic Dependency Networks: Inferring Patterns of Ctl Escape and Codon Covariation in Hiv-1 Gag, PLoS Comput Biol 4 (11), e1000225 (2008) PMC2579584

12 Rolland, M., Carlson, J. M., Manocheewa, S., Swain, J. V., Lanxon-Cookson, E., Deng, W., Rousseau, C. M., Raugi, D. N., Learn, G. H., Maust, B. S., Coovadia, H., Ndung'u, T., Goulder, P. J., Walker, B. D., Brander, C., Heckerman, D. E., and Mullins, J. I., Amino-Acid Co-Variation in Hiv-1 Gag Subtype C: Hla-Mediated Selection Pressure and Compensatory Dynamics, PLoS One 5 (9), e12463 (2010) PMC2931691

13 Pornillos, O., Ganser-Pornillos, B. K., Kelly, B. N., Hua, Y., Whitby, F. G., Stout, C. D., Sundquist, W. I., Hill, C. P., and Yeager, M., X-Ray Structures of the Hexameric Building Block of the Hiv Capsid, Cell 137 (7), 1282-92 (2009) PMC2840706

14 Worthylake, D. K., Wang, H., Yoo, S., Sundquist, W. I., and Hill, C. P., Structures of the Hiv-1 Capsid Protein Dimerization Domain at 2.6 a Resolution, Acta Crystallogr D Biol Crystallogr 55 (Pt 1), 85-92 (1999)

15 Von Schwedler, U. K., Stray, K. M., Garrus, J. E., and Sundquist, W. I., Functional Surfaces of the Human Immunodeficiency Virus Type 1 Capsid Protein, J Virol 77 (9), 5439-50 (2003)

16 Ganser-Pornillos, B. K., Von Schwedler, U. K., Stray, K. M., Aiken, C., and Sundquist, W. I., Assembly Properties of the Human Immunodeficiency Virus Type 1 Ca Protein, J Virol 78 (5), 2545-52 (2004) PMC369201

17 Zhao, G., Perilla, J. R., Yufenyuy, E. L., Meng, X., Chen, B., Ning, J., Ahn, J., Gronenborn, A. M., Schulten, K., Aiken, C., and Zhang, P., Mature Hiv-1 Capsid Structure by Cryo-Electron Microscopy and All-Atom Molecular Dynamics, Nature 497 (7451), 643-6 (2013) PMC3729984

18 Krivov, G. G., Shapovalov, M. V., and Dunbrack, R. L., Jr., Improved Prediction of Protein Side-Chain Conformations with Scwr14, Proteins 77 (4), 778-95 (2009) PMC2885146

19 Phillips, J. C., Braun, R., Wang, W., Gumbart, J., Tajkhorshid, E., Villa, E., Chipot, C., Skeel, R. D., Kale, L., and Schulten, K., Scalable Molecular Dynamics with Namd, Journal of computational chemistry 26 (16), 1781-802 (2005) PMC2486339

20 Schymkowitz, J., Borg, J., Stricher, F., Nys, R., Rousseau, F., and Serrano, L., The Foldx Web Server: An Online Force Field, Nucleic Acids Res 33 (Web Server issue), W382-8 (2005) PMC1160148

21 Shen, M. Y. and Sali, A., Statistical Potential for Assessment and Prediction of Protein Structures, Protein Sci 15 (11), 2507-24 (2006) PMC2242414

22 Guerois, R., Nielsen, J. E., and Serrano, L., Predicting Changes in the Stability of Proteins and Protein Complexes: A Study of More Than 1000 Mutations, J Mol Biol 320 (2), 369-87 (2002)

23 Eswar, N., Webb, B., Marti-Renom, M. A., Madhusudhan, M. S., Eramian, D., Shen, M. Y., Pieper, U., and Sali, A., Comparative Protein Structure Modeling Using Modeller, Current protocols in bioinformatics/editoral board, Andreas D. Baxevanis . . . [et al.] Chapter 5, Unit 5 6 (2006)

24 Rose, P. P. and Korber, B. T., Detecting Hypermutations in Viral Sequences with an Emphasis on G→a Hypermutation, Bioinformatics 16 (4), 400-1 (2000)

25 Edgar, R. C., Muscle: A Multiple Sequence Alignment Method with Reduced Time and Space Complexity, BMC Bioinformatics 5, 113 (2004)

26 Maddison, W. P. and Maddison, D. R., Mesquite: A Modular System for Evolutionary Analysis (2011).

27 Llano, A., Williams, A., Overa, A., Silva-Arrieta, S., and Brander, C. eds., Best-Characterized Hiv-1 Ctl Epitopes: The 2013 Update, 2013 ed. (Theoretical Biology and Biophysics Group, Los Alamos National Laboratory, Los Alamos, NM. LA-UR 13-27758, Los Alamos, 2013).

All publications, accession numbers, patents, and patent applications cited in this specification are herein incorporated by reference as if each was specifically and individually indicated to be incorporated by reference.

TABLE 1

Illustrative HIV Env Conserved Element Sequences
The amino acid residues that differ between the two alternative conserved element sequences in each set are underlined.

| | |
|---|---|
| EnvCE6 | WVTVYYGVPVW (SEQ ID NO: 1) |
| EnvCE1-1 | HNVWATHACVPTDP (SEQ ID NO: 2) |
| EnvCE1-2 | HNIWATHACVPTDP (SEQ ID NO: 3) |
| EnvCE7-1 | ISLWDQSLKPCVKLTPLCVTL (SEQ ID NO: 4) |
| EnvCE7-2 | ISLWDESLKPCVKLTPLCVTL (SEQ ID NO: 5) |
| EnvCE8-1 | FEPIPIHYCTPAGFA (SEQ ID NO: 6) |
| EnvCE8-2 | FDPIPIHYCAPAGYA (SEQ ID NO: 7) |
| EnvCE9-1 | VQCTHGIRPVVSTQLLLNGSLAE (SEQ ID NO: 8) |
| EnvCE9-2 | VQCTHGIKPVVSTQLLLNGSLAE (SEQ ID NO: 9) |
| EnvCE10-1 | SGGDPEIVMHSFNCGGEFFYC (SEQ ID NO: 10) |
| EnvCE10-2 | AGGDLEITTHSFNCRGEFFYC (SEQ ID NO: 11) |
| EnvCE11-1 | DNWRSELYKYKVV (SEQ ID NO: 12) |
| EnvCE11-2 | NNWRSELYKYKVV (SEQ ID NO: 13) |
| EnvCE12-1 | ARRRVVQREKRA (SEQ ID NO: 14) |
| EnvCE12-2 | AKRRVVEREKRA (SEQ ID NO: 15) |
| EnvCE13-1 | GFLGTAGSTMGAAS (SEQ ID NO: 16) |
| EnvCE13-2 | GFLGAAGSTMGAAS (SEQ ID NO: 17) |
| EnvCE14-1 | LTVQARLLLSGIVQQQNNLLRAIEAQQHLLQLTVWGIKQLQAR (SEQ ID NO: 18) |
| EnvCE14-2 | LTVQARQLLSGIVQQQSNLLKAIEAQQHMLQLTVWGIKQLQTR (SEQ ID NO: 19) |
| EnvCE15-1 | WLWYIKIFIMIVGGLVGLRI (SEQ ID NO: 20) |
| EnvCE15-2 | WLWYIRIFIMIVGGLIGLRI (SEQ ID NO: 21) |
| EnvCE16-1 | RVRKGYSPLSLQT (SEQ ID NO: 22) |
| EnvCE16-2 | RVRQGYSPLSFQT (SEQ ID NO: 23) |
| Alternative EnvCE: | |
| EnvCE17-1 | PIPIHYCAPAGFAILKC (SEQ ID NO: 70) |
| EnvCE17-2 | PIPIHYCTPAGYAILKC (SEQ ID NO: 71) |
| EnvCE18-1 | NVSTVQCTHGIRPVVSTQLLLNGSLAE (SEQ ID NO: 72) |

TABLE 1-continued

| Illustrative HIV Env Conserved Element Sequences The amino acid residues that differ between the two alternative conserved element sequences in each set are underlined. | |
|---|---|
| envCE18-2 | NVSSVQCTHGIKPVVSTQLLLNGSLAE (SEQ ID NO: 73) |
| EnvCE19-1 | GGDPEIVMHTFNCGGEFFYC (SEQ ID NO: 74) |
| envCE19-2 | GGDLEITTHSFNCRGEFFYC (SEQ ID NO: 75) |
| EnvCE20-1 | CRIKQIINMWQ (SEQ ID NO: 76) |
| EnvCE20-2 | CKIRQIVNRWQ (SEQ ID NO: 77) |
| EnvCE21-1 | GGDMRDNWRSELYKYKVV (SEQ ID NO: 78) |
| EnvCE21-2 | GGNMKDNWRSELYKYKVV (SEQ ID NO: 79) |
| envCE22-1 | LTVQARLLLSGIVQQQNNLLRAIEAQQHLLQLTVWGIKQLQARVLA (SEQ ID NO: 80) |
| envCE22-2 | LTVQARQLLSGIVQQQSNLLKAIEAQQHMLQLTVWGIKQLQTRVLA (SEQ ID NO: 81) |
| EnvCE23-1 | DQQLLGIWGCSGKLIC (SEQ ID NO: 82) |
| EnvCE23-2 | DQQLLGLWGCSGKLIC (SEQ ID NO: 83) |
| EnvCE24-1 | WLWYIKIFIMIVGGLVGLRI (SEQ ID NO: 84) |
| EnvCE24-2 | WLWYIRIFIMIVGGLIGLRI (SEQ ID NO: 85) |
| SEQ ID NO: 24. Env conserved element 1 immunogenic polypeptide sequence comprising 12 conserved element: CE6, CE1-1, CE7-1, CE8-1, CE9-1, CE10-1, CE11-1, CE12-1, CE13-1, CE14-1, CE15-1, and CE16-1. The linker amino acids between the individual conserved elements are underlined. WVTVYYGVPVWAAVHNVWATHACVPTDPAAEISLWDQSLKPCVKLTPLCVTLGAKFEPIPIH YCTPAGFAGAKVQCTHGIRPVVSTQLLLNGSLAEAADSGGDPEIVMHSFNCGGEFFYCGAKD NWRSELYKYKVVAAKARRRVVQREKRAGAVGFLGTAGSTMGAASVAVLTVQARLLLSGIVQQ QNNLLRAIEAQQHLLQLTVWGIKQLQARAADWLWYIKIFIMIVGGLVGLRIAAFRVRKGYSP LSLQT | |
| SEQ ID NO: 25. Env conserved element 2 immunogenic polypeptide sequence comprising 12 conserved element: CE6, CE1-2, CE7-2, CE8-2, CE9-2, CE10-2, CE11-2, CE12-2, CE13-2, CE14-2, CE15-2, and CE16-2. The linker amino acids between the individual conserved elements are underlined. | |

WVTVYYGVPVWAAVHNIWATHACVPTDPAAEISLWDESLKPCVKLTPLCVTLGAKFDPIPIH

YCAPAGYAGAKVQCTHGIKPVVSTQLLLNGSLAEAADAGGDLEITTHSFNCRGEFFYCGAKN

NWRSELYKYKVVAAKAKRRVVEREKRAGAVGFLGAAGSTMGAASVAVLTVQARQLLSGIVQQ

QSNLLKAIEAQQHMLQLTVWGIKQLQTRAADWLWYIRIFIMIVGGLIGLRIAAFRVRQGYSP

LSFQT

Figure 25:
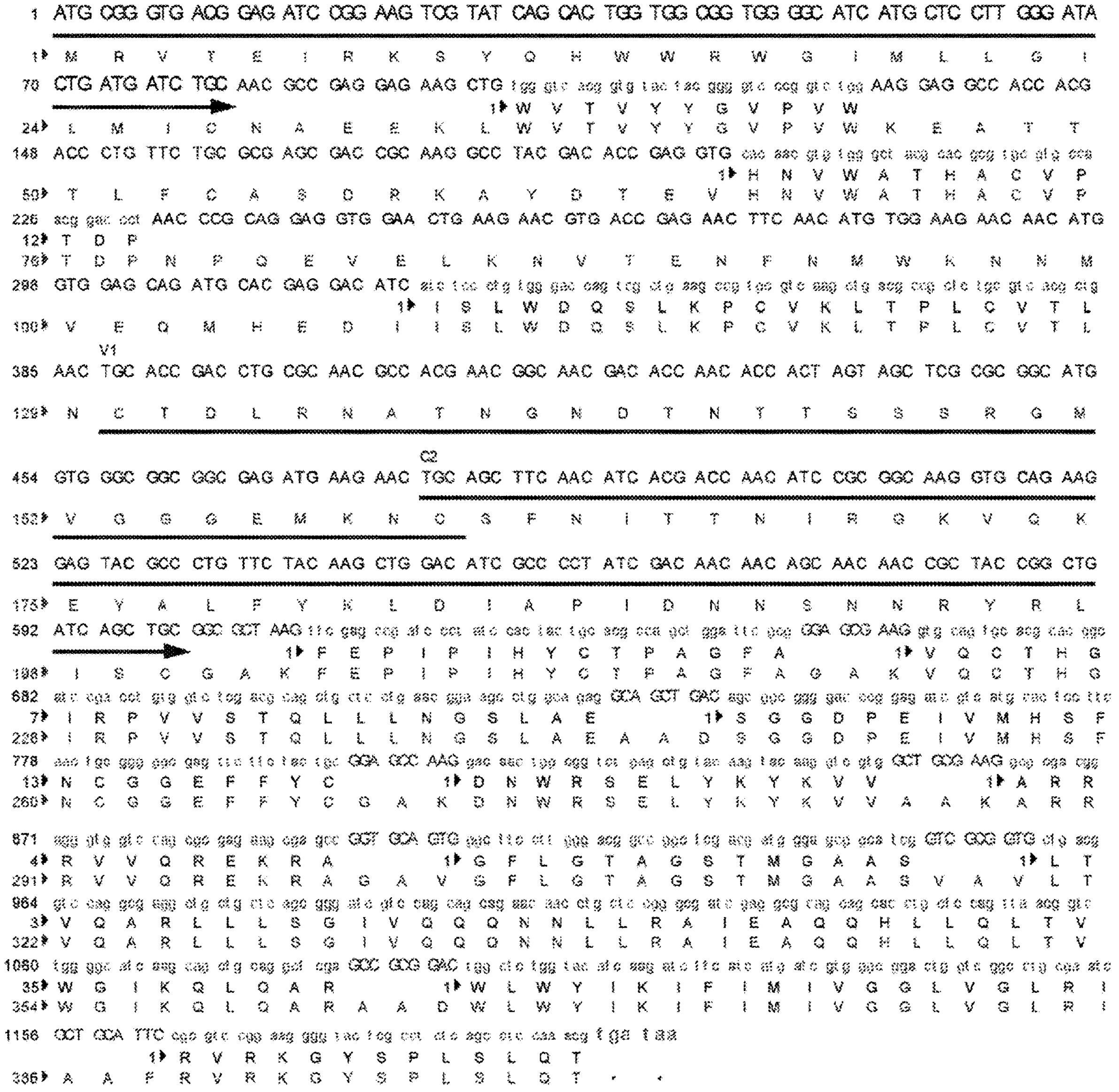
FIG. 25 shows and illustrates the HIV Env CE polypeptide (Env-CE1_v1V2 BaL; SEQ ID NO:69) and nucleic acid sequence (SEQ ID NO:89) comprising a V1V2 sequence.

FIG. 25 Env-CE1_V1V2-containing CE construct amino acid sequence

SEQ ID NO: 69

MRVTEIRKSYQHWWRWGIMLLGILMICNAEEKLWVTVYYGVPVWKEATTTLFCAS

DRKAYDTEVHNVWATHACVPTDPNPQEVELKNVTENFNMWKNNMVEQMHEDIISL

WDQSLKPCVKLTPLCVTLNCTDLRNATNGNDTNTTSSSRGMVGGGEMKNCSFNITT

NIRGKVQKEYALFYKLDIAPIDNNSNNRYRLISCGAKFEPIPIHYCTPAGFAGAKVQC

THGIRPVVSTQLLLNGSLAEAADSGGDPEIVMHSFNCGGEFFYCGAKDNWRSELYK

-continued

YKVVAAKARRRVVQREKRAGAVGFLGTAGSTMGAASVAVLTVQARLLLSGIVQQQ

NNLLRAIEAQQHLLQLTVWGIKQLQARAADWLWYIKIFIMIVGGLVGLRIAAFRVRK

GYSPLSLQT

Alternative EnvCE Arrangements (Env CE Order):

EnvCE6, EnvCE1-1, EnvCE7-1, EnvCE17-1, EnvCE18-1, EnvCE19-1, EnvCE20-1, EnvCE21-1, EnvCE12-1, EnvCE13-1, EnvCE22-1, EnvCE23-1, EnvCE24-1, EnvCE16-1 and EnvCE6, EnvCE1-2, EnvCE7-2, EnvCE17-2, EnvCE18-2, EnvCE19-2, EnvCE20-2, EnvCE21-2, EnvCE12-2, EnvCE13-2, EnvCE22-2, EnvCE23-2, EnvCE24-2, EnvCE16-2

TABLE 2

| Illustrative HIV Gag conserved element sequences: |
|---|
| p24 Gag conserved elements for p24CE1 vaccine ("also referred to as "p24 CE1"):<br>SEQ ID NO: 26 conserved element 1 (CE1)<br>ISPRTLNAWVKV |
| SEQ ID NO: 27 conserved element 2 (CE2)<br>VIPMFSALSEGATPQDLN |
| SEQ ID NO: 28 conserved element 3 (CE3)<br>VGGHQAAMQMLKDTINEEAAEWDR |
| SEQ ID NO: 29 conserved element 4 (CE4)<br>PRGSDIAGTTSTLQEQIGW |
| SEQ ID NO: 30 conserved element 5 (CE5)<br>KRWIILGLNKIVRMYSPTSI |
| SEQ ID NO: 31 conserved element 6 (CE6)<br>YVDRFYKTLRAEQA |
| SEQ ID NO: 32 conserved element 7 (CE7)<br>LEEMMTACQGVGGPGHK |
| p24 Gag conserved elements for p24CE2 vaccine ("also referred to as p24 CE2"):<br>SEQ ID NO: 33 conserved element 1 (CE1)<br>LSPRTLNAWVKV |
| SEQ ID NO: 34 conserved element 2 (CE2)<br>VIPMFTALSEGATPQDLN |
| SEQ ID NO: 35 conserved element 3 (CE3)<br>VGGHQAAMQMLKETINEEAAEWDR |
| SEQ ID NO: 36 conserved element 4 (CE4)<br>PRGSDIAGTTSTLQEQIAW |
| SEQ ID NO: 37 conserved element 5 (CE5)<br>KRWIILGLNKIVRMYSPVSI |
| SEQ ID NO: 38 conserved element 6 (CE6)<br>YVDRFFKTLRAEQA |
| SEQ ID NO: 39 conserved element 7 (CE7)<br>LEEMMTACQGVGGPSHK |
| SEQ ID NO: 40 amino acid sequence of p24 Gag CE1 polypeptide:<br>VIPMFSALSEGATPQDLNAAVGGHQAAMQMLKDTINEEAAEWDRAAAEPRGSDIAG<br>TTSTLQEQIGWAAAKRWIILGLNKIVRMYSPTSIAAKYVDRFYKTLRAEQAAGLEEM<br>MTACQGVGGPGHKAAISPRTLNAWVKV |
| SEQ ID NO: 41 amino acid sequence of p24 Gag CE2 polypeptide:<br>VIPMFTALSEGATPQDLNAAVGGHQAAMQMLKETINEEAAEWDRAAAEPRGSDIAG<br>TTSTLQEQIAWAAAKRWIILGLNKIVRMYSPVSIAAKYVDRFFKTLRAEQAAGLEEM<br>MTACQGVGGPSHKAALSPRTLNAWVKV |

TABLE 2-continued

Illustrative HIV Gag conserved element sequences:

SEQ ID NO: 42 polypeptide sequence of p24CE1 including a GM-CSF signal peptide
MWLQSLLLLGTVACSISVIPMFSALSEGATPQDLNAAVGGHQAAMQMLKDTINEEA
AEWDRAAAEPRGSDIAGTTSTLQEQIGWAAAKRWIILGLNKIVRMYSPTSIAAKYVD
RFYKTLRAEQAAGLEEMMTACQGVGGPGHKAAISPRTLNAWVKV SEQ ID NO: 43 polypeptide sequence of p24CE2 including a GM-CSF signal peptide
MWLQSLLLLGTVACSISVIPMFTALSEGATPQDLNAAVGGHQAAMQMLKETINEEA
AEWDRAAAEPRGSDIAGTTSTLQEQIAWAAAKRWIILGLNKIVRMYSPVSIAAKYVD
RFFKTLRAEQAAGLEEMMTACQGVGGPSHKAALSPRTLNAWVKV SEQ ID NO: 44 LAMP-p24CE1 (p24CE1 underlined)
MAPRSARRPLLLLLLLLLLGLMHCASAAMFMVKNGNGTACIMANFSAAFSVNYDT
KSGPKNMTLDLPSDATVVLNRSSCGKENTSDPSLVIAFGRGHTLTLNFTRNATRYSV
QLMSFVYNLSDTHLFPNASSKEIKTVESITDIRADIDKKYRCVSGTQVHMNNVTVTL
HDATIQAYLSNSSFSRGETRCEQDRPSPTTAPPAPPSPSPSPVPKSPSVDKYNVSGTNG
TCLLASMGLQLNLTYERKDNTTVTRLLNINPNKTSASGSCGAHLVTLELHSEGTTVL
LFQFGMNASSSRFFLQGIQLNTILPDARDPAFKAANGSLRALQATVGNSYKCNAEEH
VRVTKAFSVNIFKVWVQAFKVEGGQFGSVEECLLDENSLEDIVIPMFSALSEGATPQ
DLNAAVGGHQAAMQMLKDTINEEAAEWDRAAAEPRGSDIAGTTSTLQEQIGWAAA
KRWIILGLNKIVRMYSPTSIAAKYVDRFYKTLRAEQAAGLEEMMTACQGVGGPGHK
AAISPRTLNAWVKVGSEFTLIPIAVGGALAGLVLIVLIAYLVGRKRSHAGYQTI SEQ ID NO: 45 LAMP-p24CE2 fusion (p24CE2 underlined)
MAPRSARRPLLLLLLLLLLGLMHCASAAMFMVKNGNGTACIMANFSAAFSVNYDT
KSGPKNMTLDLPSDATVVLNRSSCGKENTSDPSLVIAFGRGHTLTLNFTRNATRYSV
QLMSFVYNLSDTHLFPNASSKEIKTVESITDIRADIDKKYRCVSGTQVHMNNVTVTL
HDATIQAYLSNSSFSRGETRCEQDRPSPTTAPPAPPSPSPSPVPKSPSVDKYNVSGTNG
TCLLASMGLQLNLTYERKDNTTVTRLLNINPNKTSASGSCGAHLVTLELHSEGTTVL
LFQFGMNASSSRFFLQGIQLNTILPDARDPAFKAANGSLRALQATVGNSYKCNAEEH
VRVTKAFSVNIFKVWVQAFKVEGGQFGSVEECLLDENSLEDIVIPMFTALSEGATPQ
DLNAAVGGHQAAMQMLKETINEEAAEWDRAAAEPRGSDIAGTTSTLQEQIAWAAA
KRWIILGLNKIVRMYSPVSIAAKYVDRFFKTLRAEQAAGLEEMMTACQGVGGPSHK
AALSPRTLNAWVKVGSEFTLIPIAVGGALAGLVLIVLIAYLVGRKRSHAGYQTI SEQ ID NO: 46 SP-p24CE2 (p24CE1 underlined)
MWLQSLLLLGTVACSISVIPMFTALSEGATPQDLNAAVGGHQAAMQMLKETINEEA
AEWDRAAAEPRGSDIAGTTSTLQEQIAWAAAKRWIILGLNKIVRMYSPVSIAAKYVD
RFFKTLRAEQAAGLEEMMTACQGVGGPSHKAALSPRTLNAWVKV SEQ ID NO: 47 MCP3-p24CE1 (p24CE1 underlined)
MWKPMPSPSNMKASAALLCLLLTAAAFSPQGLAQPVGINTSTTCCYRFINKKIPKQR
LESYRRTTSSHCPREAVIFKTKLDKEICADPTQKWVQDFMKHLDKKTQTPKL
VIPMFSALSEGATPQDLNAAVGGHQAAMQMLKDTINEEAAEWDRAAAEPRGSDIAG
TTSTLQEQIGWAAAKRWIILGLNKIVRMYSPTSIAAKYVDRFYKTLRAEQAAGLEEM
MTACQGVGGPGHKAAISPRTLNAWVKV SEQ ID NO: 48 MCP3-p24CE2 (p24CE2 is underlined)
MWKPMPSPSNMKASAALLCLLLTAAAFSPQGLAQPVGINTSTTCCYRFINKKIPKQR
LESYRRTTSSHCPREAVIFKTKLDKEICADPTQKWVQDFMKHLDKKTQTPKL
VIPMFTALSEGATPQDLNAAVGGHQAAMQMLKETINEEAAEWDRAAAEPRGSDIAG
TTSTLQEQIAWAAAKRWIILGLNKIVRMYSPVSIAAKYVDRFFKTLRAEQAAGLEEM
MTACQGVGGPSHKAALSPRTLNAWVKV SEQ ID NO: 49 SP-p24CE1c (p24CE1c underlined) alternative CE polypeptide. Includes GM-CSF signal peptide, CE1 and CE2 replaced by CE8 and CE9, respectively (relative to p24 CE "Core1"); lacks CE7; arranged in the configuration of conserved elements: CE 8-9-3-4-5-6
MWLQSLLLLGTVACSISQGQMVHQAISPRTLNAWVKVLAKEEKAFSPEVIPMFSALS
EGATPQDLNAAKVGGHQAAMQMLKETINEEAAEWDRAAAEPRGSDIAGTTSTLQE
QIGWAAAKRWIILGLNKIVRMYSPTSIAAKYVDRFYKTLRAEQADYKDDDDKL SEQ ID NO: 50 Gag conserved element 8 (CE8)
QGQMVHQAISPRTLNAWVKV SEQ ID NO: 51 Gag conserved element 9 (CE9)
EEKAFSPEVIPMFSALSEGATPQDLN SEQ ID NO: 52 SP-p24CE2c-alternative CE polypeptide p24CE2c underlined
MWLQSLLLLGTVACSISQGQMVHQALSPRTLNAWVKVLAKEEKGFNPEVIPMFTAL
SEGATPQDLNAAKVGGHQAAMQMLKDTINEEAAEWDRAAAEPRGSDIAGTTSTLQ
EQIAWAAAKRWIILGLNKIVRMYSPVSIAAKYVDRFFKTLRAEQA TABLE 2-continued

| Illustrative HIV Gag conserved element sequences: |
| --- |
| SEQ ID NO: 53 SP-p24CE2d alternative CE polypeptide construct; in order CE9-3-4-5-6-8<br>MWLQSLLLLGTVACSISEEKGFNPEVIPMFTALSEGATPQDLNAAKVGGHQAAMQM<br>LKDTINEEAAEWDRAAAEPRGSDIAGTTSTLQEQIAWAAAKRWIILGLNKIVRMYSP<br>VSIAAKYVDRFFKTLRAEQAALQGQMVHQALSPRTLNAWVKV |
| SEQ ID NO: 54 SP-24CE1d-alternative CE polypeptide construction; in order CE9-3-4-5-6-8<br>MWLQSLLLLGTVACSISEEKAFSPEVIPMFSALSEGATPQDLNAAKVGGHQAAMQM<br>LKETINEEAAEWDRAAAEPRGSDIAGTTSTLQEQIGWAAAKRWIILGLNKIVRMYSP<br>TSIAAKYVDRFYKTLRAEQAALQGQMVHQAISPRTLNAWVKV |
| p24CE1d has 6 CE (is identical to p24CE1c except for the CE arrangement within the protein)<br>GM-CSF signal peptide<br>CE1 and C2 replaced by CE8 and CE9 respectively, lacks CE7 and has the CE arranged in the configuration CE9-3-4-5-6-8 |
| SEQ ID NO: 55 Gag conserved element 8 (CE8-variant for CE2 constructs)<br>QGQMVHQALSPRTLNAWVKV |
| SEQ ID NO: 56 Gag conserved element 9 (CE9)<br>EEKGFNPEVIPMFTALSEGATPQDLN |
| Differences between CE for p24 CE polypeptides and variant p24CE polypeptides is one amino acid per CE except CE9, which differs by 3 amino acids<br>Alternative Gag p24 conserved elements: |

| | |
| --- | --- |
| p24CE8-1 | QPISPRTLNAWVKV (SEQ ID NO: 57) |
| p24CE8-2 | QALSPRTLNAWVKV (SEQ ID NO: 58) |
| p24CE9-1 | EEKAFSPEVIPMFSALSEGATPQDLNTMLN (SEQ ID NO: 59) |
| p24CE9-2 | EEKGFNPEVIPMFTALSEGATPQDLNMMLN (SEQ ID NO: 60) |
| p24CE10-1 | PRGSDIAGTTSTLQEQIGWMT (SEQ ID NO: 61) |
| p24CE10-2 | PRGSDIAGTTSTLQEQIAWMT (SEQ ID NO: 62) |
| p24CE11-1 | SILDIRQGPKEPFRDYVDRF (SEQ ID NO: 63) |
| p24CE11-2 | SILDIKQGPKEPFRDYVDRF (SEQ ID NO: 64) |
| p24CE12-1 | QNSNPDCKTILKALG (SEQ ID NO: 65) |
| p24CE12-2 | QNANPDCKTILKALG (SEQ ID NO: 66) |
| p24CE13-1 | LEEMMTACQGVGGPGHKARILAEAM (SEQ ID NO: 67) |
| p24CE13-2 | LEEMMTACQGVGGPSHKARVLAEAM (SEQ ID NO: 68) |

Alternative p24CE arrangements:

P24CE8-1, p24CE9-1, p24CE3-1, p24CE10-1, p24CE5-1, p24CE11-1, p24CE6-1, p24CE12-1, p24CE13-1

P24CE8-2, p24CE9-2, p24CE3-2, p24CE10-2, p24CE5-2, p24CE11-2, p24CE6-2, p24CE12-2, p24CE13-2

TABLE 3

Accuracy of using mutation frequency or change in structural stability to predict viral infectivity in binary classification manner

| Predictor | Sensitivity[d] | Specificity[e] | Precision[f] | Accuracy[g] |
| --- | --- | --- | --- | --- |
| Mutation frequency[a] | 59.5% | 70.0% | 67.10% | 64.10% |
| Stability of reference models[b] | 72.34% | 77.78% | 77.30% | 75.00% |
| Composite Score[c] | 80.00% | 79.57% | 78.16% | 79.78% |

[a]Mutations with a database frequency of 0.2% or less are predicted to result in non-infectious virus

[b]Mutants with structural stability higher than the reference models are predicted to result in non-infectious virus

[c]Mutants with a composite score (sum of ranks of frequency and stability scores) higher than 175 are predicted to result in non-infectious virus

[d]Sensitivity = (True positive)/(True positive + False negative)

[e]Specificity = (True negative)/(True negative + False positive)

[f]Precision = (True positive)/(True positive + False positive)

[g]Accuracy = (True positive + True negative)/(True positive + True negative + False positive + False negative)

TABLE 4

Amino acid sites within HIV-1 CA prone to destabilizing mutations

| Site (HXB2) | Consensus AA | Frequency | Structural element and location in capsid hexamer and/or CTD dimer | Solvent accessibility surface area ($A^2$) | Binding site of CA inhibitors |
|---|---|---|---|---|---|
| 2 | ILE | 0.98 | β-hairpin | 10.22 | None |
| 8 | GLY | 0.99 | β-hairpin | 40.98 | None |
| 20 | LEU | 0.99 | Helix 1; capsid hexamerization (NTD-NTD) interface | 2.1 | None |
| 23 | TRP | 0.99 | Helix1 | 2.81 | CAP-1, BD3, BM4 Inhibitor3 |
| 32 | PHE | 0.99 | β turn in loop region between helix 1 and 2 | 5.97 | CAP-1; BD3, BM4; Inhibitor3 Benzodiazepine series 33 |
| 36 | VAL | 0.97 | Helix 2 | 0.65 | I-XW-053; BD3 Inhibitor3 |
| 37 | ILE | 0.97 | Helix 2 | 17.74 | Inhibitor3 |
| 40 | PHE | 0.99 | Helix 2 | 0 | Inhibitor3 |
| 43 | LEU | 0.98 | Helix 2; capsid hexamerization (NTD-NTD) interface | 13.74 | None |
| 49 | PRO | 0.99 | Helix 3 | 0 | None |
| 52 | LEU | 0.99 | Helix 3 | 0.02 | None |
| 55 | MET | 0.99 | Helix 3 | 0.69 | None |
| 56 | LEU | 0.99 | Helix 3 | 12.75 | Inhibitor3 {ref} |
| 65 | ALA | 0.99 | Helix 4 | 0 | CAP-1; Inhibitor3; Benzodiazepine series 33 |
| 66 | MET | 0.99 | Helix 4 | 13.09 | Inhibitor3; PF-3450074 |
| 69 | LEU | 0.99 | Helix 4 | 2.91 | Inhibitor3 |
| 73 | ILE | 0.99 | Helix 4 | 13.8 | PF-3450074; |
| 80 | TRP | 0.99 | Helix 4 | 40.65 | Inhibitor 4 |
| 99 | PRO | 0.99 | Loop between helix 4 and 5 | 8.6 | None |
| 101 | GLY | 0.99 | Helix 5 | 0.1 | None |
| 104 | ILE | 0.99 | Helix 5 | 0 | None |
| 106 | GLY | 0.99 | β turn in loop region between helix 5 and 6 | 18.65 | None |
| 109 | SER | 0.99 | β turn in loop region between helix 5 and 6 | 13.19 | None |
| 111 | LEU | 0.99 | Helix 6 | 53.08 | None |
| 117 | TRP | 0.99 | Helix 6 | 0.24 | Inhibitor 4; |
| 126 | VAL | 0.99 | Helix 7 | 0 | None |
| 133 | TRP | 0.99 | Helix 7 | 10.88 | None |
| 134 | ILE | 0.99 | Helix 7 | 0 | Inhibitor3 |
| 138 | LEU | 0.98 | Helix 7 | 0.66 | Inhibitor3 |
| 141 | ILE | 0.99 | Helix 7 | 0.22 | CAP-1; Inhibitor3 |
| 142 | VAL | 0.99 | Helix 7 | 0.84 | Inhibitor3 |
| 144 | MET | 0.99 | Helix 7 | 20.6 | None |
| 150 | ILE | 0.99 | Linker region between NTD and CTD; CTD dimerization interface | 23.25 | CAC1; CP4 peptide |
| 153 | ILE | 0.99 | Linker region between NTD and CTD; CTD dimerization interface | 11.75 | None |
| 161 | PHE | 0.99 | Helix 8; MHR | 6.88 | None |
| 165 | VAL | 0.99 | Helix 8; MHR; capsid hexamerization (NTD-CTD) interface | 0 | I-XW-053; CAI-compound series; H8; NYAD peptides |
| 168 | PHE | 0.99 | Helix 8; MHR | 0.12 | I-XW-053; NYAD peptides |
| 169 | TYR | 0.99 | Helix 8; MHR; capsid hexamerization (NTD-CTD) interface | 30.73 | I-XW-053; CAI peptide; CAI-compound series; NYAD peptides |
| 172 | LEU | 0.99 | Helix 8; MHR; CTD dimerization interface | 5.4 | I-XW-053; CAC1, H8; NYAD peptides |
| 189 | LEU | 0.99 | Helix 9; CTD dimerization interface | 24.94 | CAC1 |
| 198 | CYS | 0.99 | Helix 10 | 12.6 | CAC1 |
| 202 | LEU | 0.99 | Helix 10 | 7.67 | CAC1 |
| 205 | LEU | 0.98 | Helix 10 | 77.49 | None |
| 206 | GLY | 0.99 | β turn in loop region between helix 10 and 11 | 28.12 | None |

TABLE 4-continued

| Amino acid sites within HIV-1 CA prone to destabilizing mutations | | | | | |
|---|---|---|---|---|---|
| Site (HXB2) | Consensus AA | Frequency | Structural element and location in capsid hexamer and/or CTD dimer | Solvent accessibility surface area ($A^2$) | Binding site of CA inhibitors |
| 211 | LEU | 0.99 | Helix 11; capsid hexamerization (NTD-CTD) interface | 4.46 | CAI-compound series; CAC1; NYAD peptides; CP4 peptide |

The invention claimed is:

1. A method of inducing an immune response to HIV Gag in a subject, the method comprising:

priming an immune response to HIV Gag, wherein priming comprises administering to the subject a conserved element (CE)-encoding expression vector that comprises a nucleic acid sequence encoding $p24^{Gag}$CE1 of SEQ ID NO: 40 fused at the N-terminus to a human GM-CSF signal peptide and a nucleic acid sequence encoding $p24^{Gag}$CE2 of SEQ ID NO: 41 fused at the N-terminus to a human GM-CSF signal peptide, wherein the subject is not co-administered or has not previously been administered a recombinant nucleic acid construct encoding a full-length or substantially full-length HIV Gag polypeptide; and boosting an immune response to HIV Gag, wherein boosting comprises co-delivering the CE-encoding expression vector with an expression vector that encodes full-length HIV-1 $p55^{gag}$ or substantially full-length HIV-1 $p55^{gag}$.

2. The method of claim 1, wherein the boosting step is performed about two months after the priming step.

3. The method of claim 1, wherein the method comprises two or three priming steps, each separated by about two months; and two boost steps, each separated by about two months.

4. A nucleic acid encoding an immunogenic HIV Env conserved element polypeptide, wherein the HIV Env conserved element polypeptide comprises at least five conserved elements selected from SEQ ID NO: 1, SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, and SEQ ID NO:22; and the conserved elements are separated by linkers of 1 to 5 amino acids in length.

5. The nucleic acid of claim 4 wherein the HIV Env conserved element polypeptide further comprises a V1V2 variable region sequence.

6. The nucleic acid of claim 4, wherein the HIV Env conserved element polypeptide comprises SEQ ID NO:24.

7. A nucleic acid encoding an immunogenic HIV Env conserved element polypeptide, wherein the HIV Env conserved element polypeptide comprises at least five conserved elements selected from SEQ ID NO: 1, SEQ ID NO:3, SEQ ID NO:5, SEQ ID NO:7, SEQ ID NO:9, SEQ ID NO: 11, SEQ ID NO: 13, SEQ ID NO: 15, SEQ ID NO: 17, SEQ ID NO: 19, SEQ ID NO:21, and SEQ ID NO:23; and the conserved elements are separated by linkers of 1 to 5 amino acids in length.

8. The nucleic acid of claim 7, wherein the HIV Env conserved element polypeptide comprises at least six, seven, eight, nine, ten, or eleven conserved elements selected from SEQ ID NO: 1, SEQ ID NO:3, SEQ ID NO:5, SEQ ID NO:7, SEQ ID NO: 9, SEQ ID NO: 11, SEQ ID NO: 13, SEQ ID NO: 15, SEQ ID NO: 17, SEQ ID NO: 19, SEQ ID NO:21, and SEQ ID NO:23.

9. The nucleic acid of claim 7, wherein the HIV Env conserved element polypeptide comprises the conserved elements of SEQ ID NO: 1, SEQ ID NO:3, SEQ ID NO:5, SEQ ID NO:7, SEQ ID NO:9, SEQ ID NO: 11, SEQ ID NO: 13, SEQ ID NO: 15, SEQ ID NO: 17, SEQ ID NO: 19, SEQ ID NO:21, and SEQ ID NO:23.

10. The nucleic acid of claim 7, further comprising a V1V2 variable region sequence.

11. The nucleic acid of claim 6, wherein the HIV Env conserved element polypeptide comprises SEQ ID NO:25.

12. The nucleic acid of claim 4, wherein the HIV Env conserved element polypeptide comprises a signal peptide.

13. The nucleic acid of claim 12, wherein the signal peptide is the signal peptide of GM-CSF.

14. An immunogenic HIV Env conserved element polypeptide, comprising at least five conserved elements selected from SEQ ID NO: 1, SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, and SEQ ID NO:22, wherein the conserved elements are separated by linkers of 1 to 5 amino acids in length.

15. The immunogenic HIV Env conserved element polypeptide of claim 14, wherein the polypeptide comprises at least six, seven, eight, nine, ten, or eleven conserved elements selected from SEQ ID NO: 1, SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, and SEQ ID NO:22.

16. The immunogenic HIV Env conserved element polypeptide of claim 14, wherein the polypeptide comprises the conserved elements of SEQ ID NO: 1, SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, and SEQ ID NO:22.

17. The immunogenic HIV Env conserved element polypeptide of claim 14, 15, or 16, wherein the polypeptide further comprises a V1V2 variable region sequence.

18. The immunogenic HIV Env conserved element polypeptide of claim 14, wherein the polypeptide comprises SEQ ID NO:24.

19. A method of inducing an immune response to HIV Env, the method comprising administering a nucleic acid construct of claim 4 to a subject or an HIV Env conserved element polypeptide of claim 16 to the subject.

20. A method of inducing an immune response to HIV Env, the method comprising administering:

a first nucleic acid encoding a first immunogenic HIV Env conserved element polypeptide that comprises at least five conserved elements selected from SEQ ID NO: 1, SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, and SEQ ID NO:22, wherein the conserved elements are separated by linkers of 1 to 5 amino acids in length; and a second nucleic acid encoding a second immunogenic HIV Env conserved element polypeptide comprises at least five conserved elements selected from SEQ ID NO: 1, SEQ ID NO:3, SEQ ID NO:5, SEQ ID NO:7, SEQ ID NO:9, SEQ ID NO: 11, SEQ ID NO: 13, SEQ ID NO: 15, SEQ ID NO: 17, SEQ ID NO: 19, SEQ ID NO: 21, and SEQ ID NO:23, wherein the conserved elements are separated by linkers of 1 to 5 amino acids in length.

21. The method of claim 20, wherein:

the first immunogenic HIV Env conserved element polypeptide comprises at least six, seven, eight, nine, ten, or eleven conserved elements selected from SEQ ID NO: 1, SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, and SEQ ID NO:22; and the second immunogenic HIV Env conserved element polypeptide comprises at least six, seven, eight, nine, ten, or eleven conserved elements selected from SEQ ID NO: 1, SEQ ID NO:3, SEQ ID NO:5, SEQ ID NO:7, SEQ ID NO:9, SEQ ID NO: 11, SEQ ID NO: 13, SEQ ID NO: 15, SEQ ID NO: 17, SEQ ID NO: 19, SEQ ID NO: 21, and SEQ ID NO:23.

22. The method of claim 20, wherein:

the first immunogenic HIV Env conserved element polypeptide comprises the conserved elements of SEQ ID NO: 1, SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, and SEQ ID NO:22; and the second immunogenic HIV Env conserved element polypeptide comprises the conserved elements of SEQ ID NO: 1, SEQ ID NO:3, SEQ ID NO:5, SEQ ID NO:7, SEQ ID NO:9, SEQ ID NO: 11, SEQ ID NO: 13, SEQ ID NO: 15, SEQ ID NO: 17, SEQ ID NO: 19, SEQ ID NO:21, and SEQ ID NO:23.

23. The method of claim 20, wherein the first immunogenic HIV Env conserved element polypeptide or the second immunogenic HIV Env conserved element polypeptide; or both the first immunogenic HIV Env conserved element polypeptide and the second immunogenic HIV Env conserved element polypeptide further comprise a V1V2 variable region sequence.

24. The method of claim 20, wherein the first immunogenic HIV Env conserved element comprises the amino acid sequence of SEQ ID NO:24 and the second immunogenic HIV Env conserved element polypeptide comprises the amino acid sequence of SEQ ID NO:25.

25. The nucleic acid of claim 4, wherein the HIV Env conserved element polypeptide comprises at least six, seven, eight, nine, ten, or eleven conserved elements selected from SEQ ID NO: 1, SEQ ID NO:2, SEQ ID NO:4, SEQ ID NO: 6, SEQ ID NO:8, SEQ ID NO: 10, SEQ ID NO: 12, SEQ ID NO: 14, SEQ ID NO: 16, SEQ ID NO: 18, SEQ ID NO:20, and SEQ ID NO:22.

26. The nucleic acid of claim 4, wherein the HIV Env conserved element polypeptide comprises the conserved elements of SEQ ID NO: 1, SEQ ID NO: 2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, and SEQ ID NO:22.

27. The method of claim 22, wherein the first nucleic acid and second nucleic acid are contained in separate expression vectors.

28. The method of claim 22 wherein the first nucleic acid and second nucleic acid are contained in the same expression vector.

29. The method of claim 22, wherein the first and the second nucleic acids are administered sequentially.

30. The method of claim 22, wherein the first and second nucleic acids are administered concurrently.

31. The method of claim 22, wherein a nucleic acid encoding a full-length Env polypeptide, or substantially full-length Env polypeptide, is administered as a boost after the first and the second nucleic acid encoding the first and the second HIV conserved element polypeptides.

32. The method of claim 22, wherein the nucleic acid constructs are administered intramuscularly by in vivo electroporation.

33. A method of inducing an immune response to HIV Env, the method comprising administering:

a first immunogenic HIV Env conserved element polypeptide that comprises at least five conserved elements selected from SEQ ID NO: 1, SEQ ID NO:2, SEQ ID NO: 4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, and SEQ ID NO:22, wherein the conserved elements are separated by linkers of 1 to 5 amino acids in length; and a second immunogenic HIV Env conserved element polypeptide comprises at least five conserved elements selected from SEQ ID NO: 1, SEQ ID NO:3, SEQ ID NO: 5, SEQ ID NO:7, SEQ ID NO:9, SEQ ID NO: 11, SEQ ID NO: 13, SEQ ID NO: 15, SEQ ID NO: 17, SEQ ID NO: 19, SEQ ID NO:21, and SEQ ID NO:23, wherein the conserved elements are separated by linkers of 1 to 5 amino acids in length.

34. The method of claim 33, wherein:

the first immunogenic HIV Env conserved element polypeptide comprises at least six, seven, eight, nine, ten, or eleven conserved elements selected from SEQ ID NO: 1, SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, and SEQ ID NO:22; and the second immunogenic HIV Env conserved element polypeptide comprises at least six, seven, eight, nine, ten, or eleven conserved elements selected from SEQ ID NO: 1, SEQ ID NO:3, SEQ ID NO:5, SEQ ID NO:7, SEQ ID NO:9, SEQ ID NO: 11, SEQ ID NO: 13, SEQ ID NO: 15, SEQ ID NO: 17, SEQ ID NO: 19, SEQ ID NO: 21, and SEQ ID NO:23.

35. The method of claim 33, wherein:

the first immunogenic HIV Env conserved element polypeptide comprises the conserved elements of SEQ ID NO: 1, SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, and SEQ ID NO:22; and the second immunogenic HIV Env conserved element polypeptide comprises the conserved elements of SEQ ID NO: 1, SEQ ID NO:3, SEQ ID NO:5, SEQ ID NO:7, SEQ ID NO:9, SEQ ID NO: 11, SEQ ID NO: 13, SEQ ID NO: 15, SEQ ID NO: 17, SEQ ID NO: 19, SEQ ID NO:21, and SEQ ID NO:23.

36. The method of claim 33, wherein the first immunogenic HIV Env conserved element polypeptide or the second immunogenic HIV Env conserved element polypeptide; or both the first immunogenic HIV Env conserved element polypeptide and the second immunogenic HIV Env conserved element polypeptide further comprise a V1V2 variable region sequence.

37. The method of claim 33, wherein the first immunogenic HIV Env conserved element comprises the amino acid sequence of SEQ ID NO:24 and the second immunogenic HIV Env conserved element polypeptide comprises the amino acid sequence of SEQ ID NO:25.

38. The method of claim 33, wherein the first and the second immunogenic HIV Env conserved element polypeptides are administered sequentially.

39. The method of claim 33, wherein the first and the second immunogenic HIV Env conserved element polypeptides are administered concurrently.

40. The method of claim 33, wherein a full-length Env polypeptide, or substantially full-length Env polypeptide, is administered after the first and the second HIV conserved element polypeptides.

41. An HIV Gag CE polypeptide comprising:

(a) SEQ ID NO:29, SEQ ID NO:31, SEQ ID NO:33, SEQ ID NO: 35, and/or SEQ ID NO:37; or (b) SEQ ID NO:28, SEQ ID NO:30, SEQ ID NO:32, SEQ ID NO:34, SEQ ID NO: 36, and/or SEQ ID NO:38.

42. An HIV Gag CE polypeptide, comprising:

p24CE8-1 of SEQ ID NO: 57, p24CE9-1 of SEQ ID NO: 59, p24CE3-1 of SEQ ID NO: 28, p24CE10-1 of SEQ ID NO: 61, p24CE5-1 of SEQ ID NO: 30, p24CE11-1 of SEQ ID NO: 63, p24CE6-1 of SEQ ID NO: 31, p24CE12-1 of SEQ ID NO: 65, p24CE13-1 of SEQ ID NO: 67 as shown in FIG. 23; or p24CE8-1 of SEQ ID NO: 57, p24CE9-2 of SEQ ID NO: 60, p24CE3-2 of SEQ ID NO: 35, p24CE10-2 of SEQ ID NO: 62, p24CE5-2 of SEQ ID NO: 37, p24CE11-2 of SEQ ID NO: 64, p24CE6-2 of SEQ ID NO: 38, p24CE1 2-2 of SEQ ID NO: 66, p24CE13-2 of SEQ ID NO: 68.

43. The method of claim 21, further comprising administering an immunogenic composition to induce an immune response to HIV Gag, wherein the immunogenic composition is an HIV Gag CE polypeptide comprising p24 CE1 of SEQ ID NO: 26, CE2 of SEQ ID NO: 27, CE3 of SEQ ID NO: 28, CE4 of SEQ ID NO: 29, CE5 of SEQ ID NO: 30, CE6 of SEQ ID NO: 31, and CE7 of SEQ ID NO: 32; or an HIV Gag CE polypeptide of claim 41 or 42.

44. The method of claim 21, further comprising administering an immunogenic composition to induce an immune response to HIV Gag, wherein the method comprises administering an HIV Gag CE polypeptide comprising p24CE8-1 of SEQ ID NO: 57, p24CE9-1 of SEQ ID NO: 59, p24CE3-1 of SEQ ID NO: 28, p24CE10-1 of SEQ ID NO: 61, p24CE5-1 of SEQ ID NO: 30, p24CE11-1 of SEQ ID NO: 63, p24CE6-1 of SEQ ID NO: 31, p24CE12-1 of SEQ ID NO: 65, p24CE 13-1 of SEQ ID NO: 67 and P24CE8-1 of SEQ ID NO: 57, p24CE9-2 of SEQ ID NO: 60, p24CE3-2 of SEQ ID NO: 35, p24CE10-2 of SEQ ID NO: 62, p24CE5-2_of SEQ ID NO: 37, p24CE11-2 of SEQ ID NO: 64, p24CE6-2_of SEQ ID NO: 38, p24CE12-2 of SEQ ID NO: 66, p24CE13-2 of SEQ ID NO: 68.

45. A nucleic acid construct encoding an HIV Gag CE polypeptide of claim 42.

46. The method of claim 43, wherein the HIV Gag CE polypeptide is administered as a nucleic acid that encodes the HIV Gag CE polypeptide.

* * * * *